(12) United States Patent
Han

(10) Patent No.: US 11,047,011 B2
(45) Date of Patent: Jun. 29, 2021

(54) IMMUNOREPERTOIRE NORMALITY ASSESSMENT METHOD AND ITS USE

(71) Applicant: iRepertoire, Inc., Huntsville, AL (US)

(72) Inventor: Jian Han, Huntsville, AL (US)

(73) Assignee: iRepertoire, Inc., Huntsville, AL (US)

( * ) Notice: Subject to any disclaimer, the term of this patent is extended or adjusted under 35 U.S.C. 154(b) by 542 days.

(21) Appl. No.: 15/278,998

(22) Filed: Sep. 28, 2016

(65) Prior Publication Data

US 2017/0088895 A1   Mar. 30, 2017

Related U.S. Application Data

(60) Provisional application No. 62/234,424, filed on Sep. 29, 2015.

(51) Int. Cl.
  *C12Q 1/68*     (2018.01)
  *C12Q 1/6883*   (2018.01)

(52) U.S. Cl.
  CPC ..... *C12Q 1/6883* (2013.01); *C12Q 2600/158* (2013.01); *C12Q 2600/16* (2013.01)

(58) Field of Classification Search
  None
  See application file for complete search history.

(56) References Cited

U.S. PATENT DOCUMENTS

| | | | | |
|---|---|---|---|---|
| 9,234,240 B2 * | 1/2016 | Quake | ................ | G16B 30/00 |
| 2010/0021896 A1 * | 1/2010 | Han | ................ | C12Q 1/686 |
| | | | | 435/6.16 |
| 2012/0171725 A1 * | 7/2012 | Han | ................ | C12P 19/34 |
| | | | | 435/91.2 |
| 2014/0127699 A1 * | 5/2014 | Han | ................ | C12Q 1/686 |
| | | | | 435/6.12 |

FOREIGN PATENT DOCUMENTS

| WO | WO-2009137255 A2 * | 11/2009 | .......... C12Q 1/6881 |
|---|---|---|---|
| WO | 2012097374 A1 | 7/2012 | |
| WO | 2014124451 A1 | 8/2014 | |
| WO | 2014179202 A1 | 11/2014 | |

OTHER PUBLICATIONS

Han Y, Li H, Guan Y, Huang J. Immune repertoire: A potential biomarker and therapeutic for hepatocellular carcinoma. Cancer Lett. Sep. 1, 2016; 379(2):206-12. Epub Jul. 15, 2015. (Year: 2015).*
Wang et al. High throughput sequencing reveals a complex pattern of dynamic interrelationships among human T cell subsets. Proceedings of the National Academy of Sciences. Jan. 26, 2010; 107(4):1518-23. (Year: 2010).*
Madi, et al., "T-Cell receptor repertoires share a restricted set of public and abundant CDR3 sequences that are associated with self-related immunity," Genome Res., Jul. 14, 2014.
Mamedov, et al., "Preparing unbiased T-cell receptor and antibody cDNA libraries for the deep next generation sequencing profiling," Front Immunol., Dec. 23, 2013.

* cited by examiner

*Primary Examiner* — Teresa E Strzelecka
*Assistant Examiner* — Olayinka A Oyeyemi
(74) *Attorney, Agent, or Firm* — Maynard Cooper & Gale, P. C.; Matthew J. Parker

(57) ABSTRACT

The present disclosure generally pertains to a method for comparing the immunorepertoire diversity of a patient to the shared immunorepertoire of a group of individuals to identify whether the immunorepertoire diversity of the patient is normal or abnormal relative to the shared immunorepertoire of the group of individuals.

15 Claims, 1 Drawing Sheet
Specification includes a Sequence Listing.

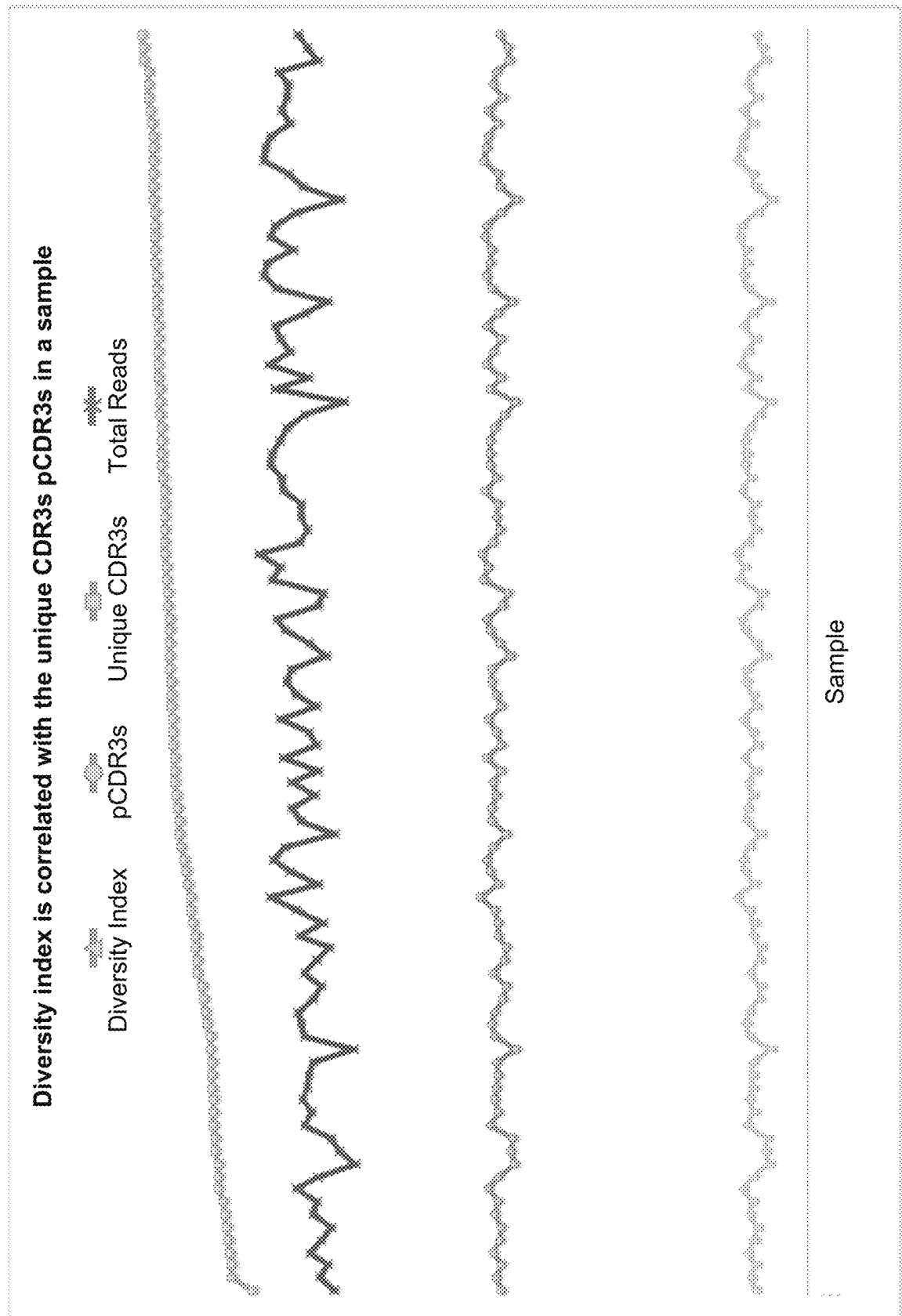

US 11,047,011 B2

IMMUNOREPERTOIRE NORMALITY ASSESSMENT METHOD AND ITS USE

CROSS REFERENCE TO RELATED APPLICATION

This application claims priority to U.S. Provisional Patent Application No. 62/234,424, entitled "Immunorepertoire Normality Assessment Method and Its Use" and filed on Sep. 29, 2015, which is incorporated herein by reference.

FIELD OF INVENTION

The present disclosure relates to methods for performing diagnostic tests. More specifically, the present disclosure relates to diagnostic tests for the assessment of immunorepertoire diversity relative to a standard index.

BACKGROUND OF INVENTION

Diagnostic tests may be used to detect the presence or absence of the normal state in a patient, and the results of these tests may be used to screen patients and collectively aid in diagnosis. For example, a normal white blood cell count is between 4,500 and 10,000 cells per microliter. An elevated white blood cell count is not determinative for a specific disease, but it may indicate an underlying problem that requires medical evaluation. Normal ranges of red blood cell counts for women and men are generally different, with a count of 5 to 6 million per microliter being normal for males and 3.6 to 5.6 million being normal for females. Platelet counts are normal if they are within the range of 150,000 to 400,000. In the presence of inflammation, for example, red cell count may go down, white cell count may go up, and platelet count may also be elevated.

Similarly, heart disease, the tendency to have heart disease, signs of certain cancers, and a variety of genetic diseases may have as their early signs one or more abnormal results for a variety of diagnostic tests. Such diagnostic tests include, for example, measures of albumin, alkaline phosphatase, alanine transaminase (ALT), aspartate aminotransferase (AST), blood urea nitrogen (BUN), serum calcium, serum chloride, carbon dioxide, creatinine, direct bilirubin, gamma-glutamyl-transpeptidase (gamma-GT), glucose, lactate dehydrogenase (LDH), serum phosphorus, potassium, serum sodium, total bilirubin, total cholesterol, total protein, and uric acid.

In addition, blood glucose levels may also be used as early indicators associated with diseases as varied as Cushing syndrome, hyperthyroidism, pancreatic cancer, pancreatitis, pre-diabetes, and diabetes.

As described above, diagnostic tests are currently available and performed on a regular basis to detect the presence or absence of a normal state in an individual. These tests, however, do not address the diversity of the immunorepertoire in a patient. The ability to detect the presence or absence of a diverse immunorepertoire, relative to a standard, in an individual may assist with an assessment of the health of such individual.

SUMMARY OF INVENTION

The present disclosure relates to a method for A method for determining the immunorepertoire diversity in a patient. The method comprises: quantifying the expression of third complementarity-determining region ("CDR3") in a population or sub-population of immune system cells in a patient sample; and identifying the percentage of pCDR3 represented by such CDR3s within that population or sub-population, wherein normal immunorepertoire diversity is characterized by the presence of a minimum percentage of pCDR3 and an abnormal immunorepertoire diversity status is characterized by the absence of a minimum percentage of pCDR3.

In certain embodiments, the minimum percentage of pCDR3 in such method is a percentage number selected from about 25 percent to about 75 percent. In other embodiments, the minimum percentage of pCDR3 is about 25 percent. In other embodiments, the pCDR3 is composed of about the 1000 most-frequently-shared CDR3. In other embodiments, the pCDR3 is composed of more than 1000 of the most-frequently-shared CDR3. In yet other embodiments, the pCDR3 is composed of fewer than 1000 of the most-frequently-shared CDR3. In other embodiments, the pCDR3 is composed of CDR3 shared by at least 25 percent of a pool of individuals.

In certain embodiments, the pCDR3 is composed of CDR3 shared by at least 50 percent of a pool of individuals. In certain embodiments, such pool contains at least 100 individuals. In other embodiments, such pool contains about 1000 individuals.

The present disclosure also relates to a method for determining the immunorepertoire diversity in a patient. The method comprises: amplifying polynucleotides from a population of white blood cells from a human or animal subject in a reaction mix comprising target-specific nested primers to produce a set of first amplicons, at least a portion of the target-specific nested primers comprising additional nucleotides which, during amplification, serve as a template for incorporating into the first amplicons a binding site for at least one common primer; transferring a portion of the first reaction mix containing the first amplicons to a second reaction mix comprising at least one common primer; amplifying, using the at least one common primer, the first amplicons to produce a set of second amplicons; sequencing the second amplicons to identify CDR3 sequences in the subpopulation of white blood cells; using the identified CDR3 sequences to quantify the percentage of pCDR3 represented by the sample to provide a normality index; and identifying whether the normality index is normal or abnormal, wherein a normal state is characterized by the presence of a minimum percentage of pCDR3 and an abnormal state is characterized by the absence of a minimum percentage of pCDR3.

In certain embodiments, such second method measures a population of white blood cells, wherein the population includes about 100,000 randomly-selected cells. In certain embodiments, the method is repeated about 10 to 100 times, each time with a random selection of cells, to determine the average percentage of pCDR3 expressed by the patient. In certain embodiments, the minimum percentage of pCDR3 is a percentage number from about 25 to about 75. In certain embodiments, the pCDR3 is composed of at least the 1000 most-frequently-shared CDR3. In certain embodiments, the pCDR3 includes SEQ ID NO:1 through SEQ ID NO: 4014 as described herein. For example, the normality index of a patient may be determined based on the percentage of pCDR3 sequences, represented by SEQ ID NO: 1 through SEQ ID NO: 4014, present in a predetermined number of reads of a patient sample. In certain embodiments, the pCDR3 is composed of CDR3 shared by at least 50 percent of a pool of individuals.

The reference pool of individuals may be different sizes. In certain embodiments, the reference pool includes at least 100 individuals. In certain embodiments, the pool contains about 1000 individuals. In certain embodiments, the pool is composed of healthy control individuals, whereas in other embodiments, the pool is composed of individuals with one or more specific disease states. The reference pool may further be controlled to account for certain variables of a given patient. In certain embodiments, the pool of individuals is approximately age-matched to the patient. In other embodiments, the pool of individuals is gender-matched to the patient.

In various aspects of the present disclosure, the immune system cells that are analyzed, under any method described herein, may include, for example, all T cells [panT], functional subsets of T cells such as CD8+ T cells [cytotoxic T (Ta)], CD4+ T cells and their subsets [TH1, TH2, TH17, regulatory T (reg) and follicular T (TFH)], or developmental subsets of T cells such as naive T (Tn), activated T (Ta), memory T (Tm), all B cells (panB) and their subsets such as naive B (Br), activated B (Ba), memory B (Bm), plasma and plasmablast B cells. Such cells may be obtained from peripheral blood or other sources known in the art.

It will be apparent to those skilled in the art that only the preferred embodiments have been described by way of exemplification and that there are various modifications which fall within the scope of the present disclosure. These and other aspects of the present disclosure will be discussed in greater detail below.

BRIEF DESCRIPTION OF THE DRAWINGS

FIG. 1 shows four plots overlaid into a single graph, representing (from top to bottom) the number of total reads, the number of unique CDR3s, the number of pCDR3s, and the normality index.

DETAILED DESCRIPTION

The inventor has developed a method for determining the diversity of a patient's immunorepertoire by comparing the CDR3 sequences in a patient sample to the most commonly-shared CDR3 sequences (i.e., the pCDR3) of an index group of individuals. This percentage of pCDR3 in a patient's sample is referred to as the "normality index" and may serve as a diagnostic indicator of the immunorepertoire diversity in such patient. The present disclosure further includes a method for determining such subset of highly-shared pCDR3. In one aspect of the present disclosure, the immunorepertoire of a patient is considered normal if the patient's normality index meets or exceeds a minimum percentage, whereas the immunorepertoire of the patient is considered abnormal of the patient's normality index is below such minimum percentage. As used herein, "patient" may refer to either a human or an animal.

The CDR3 expressed by individuals exhibits tremendous diversity, with up to $10^{15}$ unique CDR3 possible. As such, the present disclosure uses CDR3 as a basis for immune system diversity. The inventor has determined, based on a sampling of 75 million CDR3, that approximately 81% of randomly-selected CDR3 are unique to a given individual and are not shared among multiple individuals. The present disclosure, however, provides a method for determining a pool of highly-shared CDR3, thereby enabling a standard index of shared CDR3 by which the diversity of an individual's immunorepertoire may be compared.

As used herein, "abnormal" means the absence of a minimum percentage of pCDR3 sequences measured in a patient. As such, abnormal indicates a difference from the reference group of individuals used to generate the pCDR3. An abnormal immunorepertoire may, but does not necessarily, indicate the presence or absence of disease in the patient.

As used herein, "immunorepertoire" means the set of distinct CDR3 sequences detected in the lymphocytes of an individual or individuals, as applicable.

The method of the present disclosure may be performed using the following steps to identify a normal immune status or an abnormal immune status in a patient, the method comprising the steps of: (a) amplifying polynucleotides from a population of white blood cells from a patient in a reaction mix comprising target-specific nested primers to produce a set of first amplicons, at least a portion of the target-specific nested primers comprising additional nucleotides which, during amplification, serve as a template for incorporating into the first amplicons a binding site for at least one common primer; (b) transferring a portion of the first reaction mix containing the first amplicons to a second reaction mix comprising at least one common primer; (c) amplifying, using the at least one common primer, the first amplicons to produce a set of second amplicons; (d) sequencing the second amplicons to identify CDR3 sequences in the subpopulation of white blood cells, and (e) using the identified CDR3 sequences to quantify the percentage of pCDR3 represented by the sample to provide a normality index; and (f) identifying whether the normality index is normal or abnormal, wherein a normal state is characterized by the presence of a minimum percentage of pCDR3 and an abnormal state is characterized by the absence of a minimum percentage of pCDR3. As shown in FIG. 1, a patient's normality index, pCDR3s and unique CDR3s are correlated.

In certain embodiments, the sequencing includes about 100,000 reads taken per sample. In certain embodiments, the reads are performed multiple times, for example about 10 to 100 times, using random selection, to obtain an average percentage of pCDR3 sequences present in the sample. The resulting number is divided by the number of pCDR3 in the reference pool to obtain a percentage, referred to as the "normality index," which is a number between 0% and 100%. For example, if a patient sample contains 400 of 1000 pCDR3 sequences, then the patient's normality index is 0.40 or 40%. In other embodiments at least 10,000 reads are taken. In other embodiments, more than 100,000 reads are taken. In other embodiments, the reads are performed less than 10 times. In other embodiments, the reads are performed more than 100 times.

In certain embodiments, the index pool is composed of about 1000 individuals. In other embodiments, the index pool contains between 100 and 1000 individuals. In other embodiments, the index pool contains fewer than 100 individuals. In other embodiments, the index pool contains more than 1000 individuals. Relative to the patient, the individuals may be age-matched, gender-matched, healthy, disease-matched, and/or other criteria commonly known in the art when controlling for variables. In certain embodiments, the index pool is composed of healthy controls. In other embodiments, the index pool is composed of a mix of healthy controls and individuals with one or more disease states. In other embodiments, the index pool is composed of individuals with one or more particular disease states.

In certain embodiments, the CDR3 sequences shared by the index pool (i.e., the pCDR3) are determined by comparing each sample from the index pool and identifying those CDR3s that are shared by at least 50% of the individuals tested in such reference pool. In certain embodiments, the pCDR3 includes about the top 1000 shared CDR3 sequences. In other embodiments, the pCDR3 include at least 100 CDR3 sequences. In other embodiments, the pCDR3 includes more than 1000 CDR3 sequences.

In certain embodiments, the minimum percentage of pCDR3, used to determine the normal or abnormal state of the immunorepertoire, is about 25%. In other embodiments, the minimum percentage of pCDR3 is between 25% and 75%.

It has previously been difficult to assess the immune system in a broad manner, because the number and variety of cells in a human or animal immune system is so large that sequencing of more than a small subset of cells has been almost impossible. The inventor developed a semi-quantitative PCR method (arm-PCR, described in more detail in U.S. Patent Application Publication Number 20090253183), which provides increased sensitivity and specificity over previously-available methods, while producing semi-quantitative results. It is this ability to increase specificity and sensitivity, and thereby increase the number of targets detectable within a single sample that makes the method ideal for detecting relative numbers of clonotypes of the immunorepertoire. The inventor has more recently discovered that using this sequencing method allows comparison of a patient's CDR3 sequences to those commonly shared by an index group, which has led to the development of the present method. The method may be used to evaluate the diversity of the immunorepertoire of subjects relative to an index pool of individuals. For example, the inventor has demonstrated that the presence of disease correlates with decreased immunorepertoire diversity, for example a decrease in the diversity of CDR3 sequences, which can be readily detected using the method of the present disclosure. This method may therefore be useful as an initial diagnostic indicator, much as cell counts and biochemical tests are currently used in clinical practice, of normal versus abnormal immunorepertoire diversity.

Clonotypes (i.e., clonal types) of an immunorepertoire are determined by the rearrangement of Variable (V), Diverse (D) and Joining (J) gene segments through somatic recombination in the early stages of immunoglobulin (Ig) and T cell receptor (TCR) production of the immune system. The V(D)J rearrangement can be amplified and detected from T cell receptor alpha, beta, gamma, and delta chains, as well as from immunoglobulin heavy chain (IgH) and light chains (IgK, IgL). Cells may be obtained from a patient by obtaining peripheral blood, lymphoid tissue, cancer tissue, or tissue or fluids from other organs and/or organ systems, for example. Techniques for obtaining these samples, such as blood samples, are known to those of skill in the art. Cell counts may be extrapolated from the number of sequences detected by PCR amplification and sequencing.

The CDR3 region, comprising about 30-90 nucleotides, encompasses the junction of the recombined variable (V), diversity (D) and joining (J) segments of the gene. It encodes the binding specificity of the receptor and is useful as a sequence tag to identify unique V(D)J rearrangements.

Wang et al. disclosed that PCR may be used to obtain quantitative or semi-quantitative assessments of the numbers of target molecules in a specimen (Wang, M. et al, "Quantitation of mRNA by the polymerase chain reaction," (1989) Proc. Nat'l. Acad. Sci. 86: 9717-9721). Particularly effective methods for achieving quantitative amplification have been described previously by the inventor. One such method is known as arm-PCR, which is described in United States Patent Application Publication Number 20090253183A1.

Aspects of the present disclosure include arm-PCR amplification of CDR3 from T cells, B cells, and/or subsets of T or B cells. Such cell types may be sorted and isolated using techniques known in the art including, but not limited to, FACS sorting and magnetic bead sorting. The term "population" of cells, as used herein, therefore encompasses what are generally referred to as either "populations" or "subpopulations" of cells. Large numbers of amplified products may then be efficiently sequenced using next-generation sequencing using platforms such as 454 or Illumina, for example.

The arm-PCR method provides highly sensitive, semi-quantitative amplification of multiple polynucleotides in one reaction. The arm-PCR method may also be performed by automated methods in a closed cassette system (iCubate®, Huntsville, Ala.), which is beneficial in the present method because the repertoires of various T and B cells, for example, are so large. In the arm-PCR method, target numbers are increased in a reaction driven by DNA polymerase, which is the result of target-specific primers being introduced into the reaction. An additional result of this amplification reaction is the introduction of binding sites for common primers which will be used in a subsequent amplification by transferring a portion of the first reaction mix containing the first set of amplicons to a second reaction mix comprising common primers. "At least one common primer," as used herein, refers to at least one primer that will bind to such a binding site, and includes pairs of primers, such as forward and reverse primers. This transfer may be performed either by recovering a portion of the reaction mix from the first amplification reaction and introducing that sample into a second reaction tube or chamber, or by removing a portion of the liquid from the completed first amplification, leaving behind a portion, and adding fresh reagents into the tube in which the first amplification was performed. In either case, additional buffers, polymerase, etc., may then be added in conjunction with the common primers to produce amplified products for detection. The amplification of target molecules using common primers gives a semi-quantitative result wherein the quantitative numbers of targets amplified in the first amplification are amplified using common, rather than target-specific primers—making it possible to produce significantly higher numbers of targets for detection and to determine the relative amounts of the cells comprising various rearrangements within a patient blood sample. Also, combining the second reaction mix with a portion of the first reaction mix allows for higher concentrations of target-specific primers to be added to the first reaction mix, resulting in greater sensitivity in the first amplification reaction. It is the combination of specificity and sensitivity, along with the ability to achieve quantitative results by use of a method such as the arm-PCR method, which allows a sufficiently sensitive and quantitative assessment of the CDR3 expressed in a population of cells to produce a normality index that is of diagnostic use.

Clonal expansion due to recognition of antigen results in a larger population of cells that recognize that antigen, potentially including antibody-producing B cells or receptor-bearing T cells. This may cause the reads taken pursuant to the method disclosed herein to be biased in favor of the antigen-specific expansion, thereby reducing the percentage of pCDR3 sequences detected. Therefore, a relatively low normality index, for example one below the minimum percentage, may be indicative of the expansion of a particular population of cells that is prevalent in individuals who have been diagnosed with a particular disease or in individuals recently-vaccinated against a particular antigen.

Primers for amplifying and sequencing variable regions of immune system cells are available commercially, and have been described in publication such as the inventor's published patent applications WO2009137255 and US201000021896A1.

There are several commercially available high-throughput sequencing technologies, such as Hoffman-LaRoche, Inc.'s 454® sequencing system. In the 454® sequencing method, for example, the A and B adaptor are linked onto PCR products either during PCR or ligated on after the PCR reaction. The adaptors are used for amplification and sequencing steps. When done in conjunction with the arm-PCR technique, A and B adaptors may be used as common primers (which are sometimes referred to as "communal primers" or "superprimers") in the amplification reactions. After A and B adaptors have been physically attached to a sample library (such as PCR amplicons), a single-stranded DNA library is prepared using techniques known to those of skill in the art. The single-stranded DNA library is immobilized onto specifically-designed DNA capture beads. Each bead carries a unique singled-stranded DNA library fragment. The bead-bound library is emulsified with amplification reagents in a water-in-oil mixture, producing microreactors, each containing just one bead with one unique sample-library fragment. Each unique sample library fragment is amplified within its own microreactor, excluding competing or contaminating sequences. Amplification of the entire fragment collection is done in parallel. For each fragment, this results in copy numbers of several million per bead. Subsequently, the emulsion PCR is broken while the amplified fragments remain bound to their specific beads. The clonally amplified fragments are enriched and loaded onto a PicoTiterPlate® device for sequencing. The diameter of the PicoTiterPlate® wells allows for only one bead per well. After addition of sequencing enzymes, the fluidics subsystem of the sequencing instrument flows individual nucleotides in a fixed order across the hundreds of thousands of wells each containing a single bead. Addition of one (or more) nucleotide(s) complementary to the template strand results in a chemilluminescent signal recorded by a CCD camera within the instrument. The combination of signal intensity and positional information generated across the PicoTiterPlate® device allows the software to determine the sequence of more than 1,000,000 individual reads, each is up to about 450 base pairs, with the GS FLX system.

Having obtained the sequences using a quantitative and/or semi-quantitative method, it is then possible to calculate the normality index, for example, by determining the percentage of pCDR3 represented by a predetermined number of reads of a patient sample. Each patient's normality index may be compared to a predetermined threshold to determine whether the patient's normality index falls within the normal range, and therefore is normal, or below the threshold, and thereby is abnormal.

The method of the present disclosure provides a physician with an additional clinical test for diagnostic purposes to determine whether a patient's immunorepertoire is abnormal. Further, the method of the present disclosure, particularly if used in an automated system such as that described by the inventor in U.S. Patent Application Publication Number 201000291668A1, may be used to analyze samples from multiple patients, with detection of the amplified targets sequences being accomplished by the use of one or more microarrays.

EXAMPLES

Patient Samples

Whole blood samples (40 ml) collected in sodium heparin or peripheral blood mononuclear cells (PBMCs) were obtained from 1100 individuals, representing a mixed population of both healthy individuals and those with disease. The 1100 individuals were placed randomly into 11 different groups with 100 samples per group.

RNA Extraction and Repertoire Amplification

RNA extraction was performed using the RNeasy Mini Kit (Qiagen) according to the manufacturer's protocol. For each target, a set of nested sequence-specific primers (Forward-out, Fo; Forward-in, Fi; Reverse-out, Ro; and Reverse-in, Ri) was designed using primer software available at irepertoire.com. A pair of common sequence tags was linked to all internal primers (Fi and Ri). Once these tag sequences were incorporated into the PCR products in the first few amplification cycles, the exponential phase of the amplification was carried out with a pair of communal primers. In the first round of amplification, only sequence-specific nested primers were used. The nested primers were then removed by exonuclease digestion and the first-round PCR products were used as templates for a second round of amplification by adding communal primers and a mixture of fresh enzyme and dNTP. Each distinct barcode tag was introduced into amplicon from the same sample through PCR primer.

Sequencing

Barcode tagged amplicon products from different samples were pooled together and loaded into a 2% agarose gel. Following electrophoresis, DNA fragments were purified from DNA band corresponding to 250-500 bp fragments extracted from agarose gel. DNA was sequenced using the 454 GS FLX system with titanium kits (SeqWright, Inc.).

Sequencing Data Analysis

Sequences for each sample were sorted out according to barcode tag. Following sequence separation, sequence analysis was performed in a manner similar to the approach reported by Wang et al. (Wang C, et al. High throughput sequencing reveals a complex pattern of dynamic interrelationships among human T cell subsets. Proc Natl Acad Sci USA 107(4): 1518-1523). Briefly, germline V and J reference sequences, which were downloaded from the IMGT server (imgt.org), were mapped onto sequence reads using the program IRmap. The boundaries defining CDR3 region in reference sequences were mirrored onto sequencing reads through mapping information. The enclosed CDR3 regions in sequencing reads were extracted and translated into amino acid sequence.

Determination of pCDR3

Sequences obtained from each of the 11 groups were compared to determine which CDR3 sequences were detected in at least 50% of the samples in each group. The resulting CDR3 sequences were sorted such that the top 4014 most commonly shared CDR3 sequences were selected as the pCDR3 for purposes of calculating a normality index for patient samples. The CDR3 sequences selected for inclusion in the pCDR3—SEQ ID NO:1 through SEQ ID NO: 4014—are shown in Table I.

TABLE I

| Sequence | Sequence ID No |
|---|---|
| ASSLGETQY | SEQ ID NO: 1 |
| ASSLSTDTQY | SEQ ID NO: 2 |

TABLE I-continued

| Sequence | Sequence ID No |
|---|---|
| ASSLGTDTQY | SEQ ID NO: 3 |
| ASSPSTDTQY | SEQ ID NO: 4 |
| ASSLQETQY | SEQ ID NO: 5 |
| ASSLTDTQY | SEQ ID NO: 6 |
| ASSLGYEQY | SEQ ID NO: 7 |
| ASSLGDTQY | SEQ ID NO: 8 |
| ASSLGGNTEAF | SEQ ID NO: 9 |
| ASSLGGNQPQH | SEQ ID NO: 10 |
| ASSLEETQY | SEQ ID NO: 11 |
| ASSLDSNQPQH | SEQ ID NO: 12 |
| ASSLGQNTEAF | SEQ ID NO: 13 |
| ASSLRETQY | SEQ ID NO: 14 |
| ASSLADTQY | SEQ ID NO: 15 |
| ASSLSYEQY | SEQ ID NO: 16 |
| ASSLGSNQPQH | SEQ ID NO: 17 |
| ASSSSYEQY | SEQ ID NO: 18 |
| ASSSQETQY | SEQ ID NO: 19 |
| ASSPQETQY | SEQ ID NO: 20 |
| ASSLGGTEAF | SEQ ID NO: 21 |
| ASSSTDTQY | SEQ ID NO: 22 |
| ASSLGGTDTQY | SEQ ID NO: 23 |
| ASSLQGNTEAF | SEQ ID NO: 24 |
| ASSLAGGTDTQY | SEQ ID NO: 25 |
| ASSLGNTEAF | SEQ ID NO: 26 |
| ASSFGETQY | SEQ ID NO: 27 |
| ASSLGGYEQY | SEQ ID NO: 28 |
| ASSLGLNTEAF | SEQ ID NO: 29 |
| ASSLGSTDTQY | SEQ ID NO: 30 |
| ASSLTGNTEAF | SEQ ID NO: 31 |
| ASSLGRNTEAF | SEQ ID NO: 32 |
| ASSPSYEQY | SEQ ID NO: 33 |
| ASSPSSYEQY | SEQ ID NO: 34 |
| ASSLYNEQF | SEQ ID NO: 35 |
| ASSLGVNTEAF | SEQ ID NO: 36 |
| ASSSSTDTQY | SEQ ID NO: 37 |
| ASSLAGTDTQY | SEQ ID NO: 38 |
| ASSFTDTQY | SEQ ID NO: 39 |
| ASSLGQGYEQY | SEQ ID NO: 40 |
| ASSLGNEQF | SEQ ID NO: 41 |
| ASSLGTEAF | SEQ ID NO: 42 |
| ASSPGTDTQY | SEQ ID NO: 43 |
| ASSLSSYEQY | SEQ ID NO: 44 |
| ASSLDSYEQY | SEQ ID NO: 45 |
| ASSLGSYEQY | SEQ ID NO: 46 |
| ASSLDRNTEAF | SEQ ID NO: 47 |
| ASSLNTEAF | SEQ ID NO: 48 |
| ASSSYNEQF | SEQ ID NO: 49 |
| ASSPGETQY | SEQ ID NO: 50 |
| ASSLGGSTDTQY | SEQ ID NO: 51 |
| ASSLGGNEQF | SEQ ID NO: 52 |
| ASSQGYEQY | SEQ ID NO: 53 |
| ASSLSDTQY | SEQ ID NO: 54 |
| ASSLTVNTEAF | SEQ ID NO: 55 |
| ASSPPSTDTQY | SEQ ID NO: 56 |
| ASSLAGNTEAF | SEQ ID NO: 57 |
| ASSLGGSYEQY | SEQ ID NO: 58 |
| ASSPGQGYEQY | SEQ ID NO: 59 |
| ASSLGQGNTEAF | SEQ ID NO: 60 |
| ASSLGGSNQPQH | SEQ ID NO: 61 |
| ASSFQETQY | SEQ ID NO: 62 |
| ASSLQGYEQY | SEQ ID NO: 63 |
| ASSLGADTQY | SEQ ID NO: 64 |
| ASSLTGGTEAF | SEQ ID NO: 65 |
| ASSLGQGNQPQH | SEQ ID NO: 66 |
| ASSLGSSYEQY | SEQ ID NO: 67 |
| ASSLGSYNEQF | SEQ ID NO: 68 |
| ASSLGGSSYEQY | SEQ ID NO: 69 |
| ASSLAGYEQY | SEQ ID NO: 70 |
| ASSLAGSTDTQY | SEQ ID NO: 71 |
| ASSLKETQY | SEQ ID NO: 72 |
| ASSLGGGTEAF | SEQ ID NO: 73 |
| ASSRDSNQPQH | SEQ ID NO: 74 |
| ASSLGPNTEAF | SEQ ID NO: 75 |
| ASSLGGDTQY | SEQ ID NO: 76 |
| ASSSSSYEQY | SEQ ID NO: 77 |
| ASSLGNQPQH | SEQ ID NO: 78 |
| ASSSTYEQY | SEQ ID NO: 79 |
| ASSLGGGTDTQY | SEQ ID NO: 80 |

TABLE I-continued

| Sequence | Sequence ID No |
|---|---|
| ASSLSSYNEQF | SEQ ID NO: 81 |
| ASSFSTDTQY | SEQ ID NO: 82 |
| ASSLGMNTEAF | SEQ ID NO: 83 |
| ASSPDSYEQY | SEQ ID NO: 84 |
| ASSPGYEQY | SEQ ID NO: 85 |
| ASSPRTDTQY | SEQ ID NO: 86 |
| ASSLDTDTQY | SEQ ID NO: 87 |
| ASSLGGETQY | SEQ ID NO: 88 |
| ASSRQETQY | SEQ ID NO: 89 |
| ASSLAETQY | SEQ ID NO: 90 |
| ASSLGQGAYEQY | SEQ ID NO: 91 |
| ASSLNSNQPQH | SEQ ID NO: 92 |
| ASSLQGNQPQH | SEQ ID NO: 93 |
| ASSRTDTQY | SEQ ID NO: 94 |
| ASSLNTGELF | SEQ ID NO: 95 |
| ASSLGQGTDTQY | SEQ ID NO: 96 |
| ASSLGQNYGYT | SEQ ID NO: 97 |
| ASSLSGNTEAF | SEQ ID NO: 98 |
| ASSLSSNQPQH | SEQ ID NO: 99 |
| ASSLTGNQPQH | SEQ ID NO: 100 |
| ASSPQGYEQY | SEQ ID NO: 101 |
| ASSLSETQY | SEQ ID NO: 102 |
| ASSLGGEQY | SEQ ID NO: 103 |
| ASSLGYNEQF | SEQ ID NO: 104 |
| ASSLRDTQY | SEQ ID NO: 105 |
| ASSFSYEQY | SEQ ID NO: 106 |
| ASSLRGNTEAF | SEQ ID NO: 107 |
| ASSLGGSYNEQF | SEQ ID NO: 108 |
| ASSPGQNTEAF | SEQ ID NO: 109 |
| ASSLAGGYNEQF | SEQ ID NO: 110 |
| ASSSGYEQY | SEQ ID NO: 111 |
| ASSPTGNTEAF | SEQ ID NO: 112 |
| ASSLGQETQY | SEQ ID NO: 113 |
| ASSLAYEQY | SEQ ID NO: 114 |
| ASSLSGYEQY | SEQ ID NO: 115 |
| ASSLTYEQY | SEQ ID NO: 116 |
| ASSLDSYNEQF | SEQ ID NO: 117 |
| ASSLEGNQPQH | SEQ ID NO: 118 |
| ASSLGQQETQY | SEQ ID NO: 119 |
| ASSYTDTQY | SEQ ID NO: 120 |
| ASSFGGNTEAF | SEQ ID NO: 121 |
| ASSLVGYEQY | SEQ ID NO: 122 |
| ASSPYNEQF | SEQ ID NO: 123 |
| ASSLEGNTEAF | SEQ ID NO: 124 |
| ASSLGGYNEQF | SEQ ID NO: 125 |
| ASSLVGNTEAF | SEQ ID NO: 126 |
| ASSLEGYEQY | SEQ ID NO: 127 |
| ASSLGQLNTEAF | SEQ ID NO: 128 |
| ASSPGDTQY | SEQ ID NO: 129 |
| ASSLAGNQPQH | SEQ ID NO: 130 |
| ASSSGETQY | SEQ ID NO: 131 |
| ASSLGGQETQY | SEQ ID NO: 132 |
| ASSPNTDTQY | SEQ ID NO: 133 |
| ASSPGGTEAF | SEQ ID NO: 134 |
| ASSLNYEQY | SEQ ID NO: 135 |
| ASSSQGYEQY | SEQ ID NO: 136 |
| ASSLVETQY | SEQ ID NO: 137 |
| ASSLGENTEAF | SEQ ID NO: 138 |
| ASSPGGYEQY | SEQ ID NO: 139 |
| ASSLAGSYEQY | SEQ ID NO: 140 |
| ASSLSGANVLT | SEQ ID NO: 141 |
| ASSPQGNTEAF | SEQ ID NO: 142 |
| ASSLLETQY | SEQ ID NO: 143 |
| ASSRGYEQY | SEQ ID NO: 144 |
| ASSLLNTEAF | SEQ ID NO: 145 |
| ASSLGPYEQY | SEQ ID NO: 146 |
| ASSYQETQY | SEQ ID NO: 147 |
| ASSYSYEQY | SEQ ID NO: 148 |
| ASSLAGGTEAF | SEQ ID NO: 149 |
| ASSLQGTDTQY | SEQ ID NO: 150 |
| ASSLRGTDTQY | SEQ ID NO: 151 |
| ASSLNTDTQY | SEQ ID NO: 152 |
| ASSLGANTEAF | SEQ ID NO: 153 |
| ASSPGLNTEAF | SEQ ID NO: 154 |
| ASSLGQGSYEQY | SEQ ID NO: 155 |
| ASSFRETQY | SEQ ID NO: 156 |
| ASSLTANTEAF | SEQ ID NO: 157 |
| ASSLNNEQF | SEQ ID NO: 158 |

TABLE I-continued

| Sequence | Sequence ID No |
|---|---|
| ASSFGDTQY | SEQ ID NO: 159 |
| ASSRQGNTEAF | SEQ ID NO: 160 |
| ASSLTENTEAF | SEQ ID NO: 161 |
| ASSLTTDTQY | SEQ ID NO: 162 |
| ASSRTGNTEAF | SEQ ID NO: 163 |
| ASSLGGQPQH | SEQ ID NO: 164 |
| ASSLTGYEQY | SEQ ID NO: 165 |
| ASSQQETQY | SEQ ID NO: 166 |
| ASSSAYEQY | SEQ ID NO: 167 |
| ASSLDGNTEAF | SEQ ID NO: 168 |
| ASSLGQSYEQY | SEQ ID NO: 169 |
| ASSLAGGYEQY | SEQ ID NO: 170 |
| ASSPTTDTQY | SEQ ID NO: 171 |
| ASSPDRNTEAF | SEQ ID NO: 172 |
| ASSLGGSSYNEQF | SEQ ID NO: 173 |
| ASSLGGYGYT | SEQ ID NO: 174 |
| ASSFGTDTQY | SEQ ID NO: 175 |
| ASSLASTDTQY | SEQ ID NO: 176 |
| ASSLGQSTDTQY | SEQ ID NO: 177 |
| ASSRSTDTQY | SEQ ID NO: 178 |
| ASSLDSTDTQY | SEQ ID NO: 179 |
| ASSSQGNTEAF | SEQ ID NO: 180 |
| ASSFGYEQY | SEQ ID NO: 181 |
| ASSLGTANTEAF | SEQ ID NO: 182 |
| ASSSPYEQY | SEQ ID NO: 183 |
| ASSLAGQETQY | SEQ ID NO: 184 |
| ASSLSNQPQH | SEQ ID NO: 185 |
| ASSLVGTDTQY | SEQ ID NO: 186 |
| ASSLVTDTQY | SEQ ID NO: 187 |
| ASSLSGNTIY | SEQ ID NO: 188 |
| ASSLGGGNQPQH | SEQ ID NO: 189 |
| ASSLRTDTQY | SEQ ID NO: 190 |
| ASSPGQGNQPQH | SEQ ID NO: 191 |
| ASSLMNTEAF | SEQ ID NO: 192 |
| ASSLSGSTDTQY | SEQ ID NO: 193 |
| ASSPRETQY | SEQ ID NO: 194 |
| ASSPDSNQPQH | SEQ ID NO: 195 |
| ASSSYTDTQY | SEQ ID NO: 196 |
| ASSLTSTDTQY | SEQ ID NO: 197 |
| ASSPGQGNTEAF | SEQ ID NO: 198 |
| ASSPGQGAYEQY | SEQ ID NO: 199 |
| ASSRNTEAF | SEQ ID NO: 200 |
| ASSQSYEQY | SEQ ID NO: 201 |
| ASSSGTDTQY | SEQ ID NO: 202 |
| ASSLGQGYGYT | SEQ ID NO: 203 |
| ASSQGETQY | SEQ ID NO: 204 |
| ASSPGQGTDTQY | SEQ ID NO: 205 |
| ASSYSTDTQY | SEQ ID NO: 206 |
| ASSLGQMNTEAF | SEQ ID NO: 207 |
| ASSLQGGTEAF | SEQ ID NO: 208 |
| ASSLVGETQY | SEQ ID NO: 209 |
| ASSLAGSYNEQF | SEQ ID NO: 210 |
| ASSRDSYEQY | SEQ ID NO: 211 |
| ASSRDSQETQY | SEQ ID NO: 212 |
| ASSLDYEQY | SEQ ID NO: 213 |
| ASSLDGNQPQH | SEQ ID NO: 214 |
| ASSRYNEQF | SEQ ID NO: 215 |
| ASSLGLQETQY | SEQ ID NO: 216 |
| ASSFSDTQY | SEQ ID NO: 217 |
| ASSPGTGSYEQY | SEQ ID NO: 218 |
| ASSLSGNQPQH | SEQ ID NO: 219 |
| ASSDSYEQY | SEQ ID NO: 220 |
| ASSLGDTEAF | SEQ ID NO: 221 |
| ASSLAGDTQY | SEQ ID NO: 222 |
| ASSRSYEQY | SEQ ID NO: 223 |
| ASSLVGNEQF | SEQ ID NO: 224 |
| ASSLGQTYEQY | SEQ ID NO: 225 |
| ASSPGGTDTQY | SEQ ID NO: 226 |
| ASSPGQGSYEQY | SEQ ID NO: 227 |
| ASSLAGETQY | SEQ ID NO: 228 |
| ASSLRGTEAF | SEQ ID NO: 229 |
| ASSPGSYEQY | SEQ ID NO: 230 |
| ASSLSRNTEAF | SEQ ID NO: 231 |
| ASSPGQQETQY | SEQ ID NO: 232 |
| ASSLGTGELF | SEQ ID NO: 233 |
| ASSLGGEQF | SEQ ID NO: 234 |
| ASSLYSNQPQH | SEQ ID NO: 235 |
| ASSPTDTQY | SEQ ID NO: 236 |

TABLE I-continued

| Sequence | Sequence ID No |
|---|---|
| ASSLAGNEQF | SEQ ID NO: 237 |
| ASSPGTGGYEQY | SEQ ID NO: 238 |
| ASSLATDTQY | SEQ ID NO: 239 |
| ASSRDSSYEQY | SEQ ID NO: 240 |
| ASSPGTANTEAF | SEQ ID NO: 241 |
| ASSLGPDTQY | SEQ ID NO: 242 |
| ASSLAVNTEAF | SEQ ID NO: 243 |
| ASSLEDTQY | SEQ ID NO: 244 |
| ASSLGGADTQY | SEQ ID NO: 245 |
| ASSLGSSYNEQF | SEQ ID NO: 246 |
| ASSLAGGSYEQY | SEQ ID NO: 247 |
| ASSRDRNTEAF | SEQ ID NO: 248 |
| ASSSDSYEQY | SEQ ID NO: 249 |
| ASSLEVNTEAF | SEQ ID NO: 250 |
| ASSLSGSSYNEQF | SEQ ID NO: 251 |
| ASSLSSTDTQY | SEQ ID NO: 252 |
| ASSLGTSTDTQY | SEQ ID NO: 253 |
| ASSLGTGSYEQY | SEQ ID NO: 254 |
| ASSLVADTQY | SEQ ID NO: 255 |
| ASSLSYNEQF | SEQ ID NO: 256 |
| ASSLGGMNTEAF | SEQ ID NO: 257 |
| ASSSGSYEQY | SEQ ID NO: 258 |
| ASSLDGYEQY | SEQ ID NO: 259 |
| ASSLSGTDTQY | SEQ ID NO: 260 |
| ASSLGSDTQY | SEQ ID NO: 261 |
| ASSQGLNTEAF | SEQ ID NO: 262 |
| ASSLVDTQY | SEQ ID NO: 263 |
| ASSLGAYEQY | SEQ ID NO: 264 |
| ASSLDRNQPQH | SEQ ID NO: 265 |
| ASSLGTYEQY | SEQ ID NO: 266 |
| ASSLVNTEAF | SEQ ID NO: 267 |
| ASSLSVNTEAF | SEQ ID NO: 268 |
| ASSAQETQY | SEQ ID NO: 269 |
| ASSLVNEQF | SEQ ID NO: 270 |
| ASSLRGYEQY | SEQ ID NO: 271 |
| ASSLTGGNTEAF | SEQ ID NO: 272 |
| ASSLDSSYEQY | SEQ ID NO: 273 |
| ASSLAGADTQY | SEQ ID NO: 274 |
| ASSLAGGPYEQY | SEQ ID NO: 275 |
| ASSPGTGNQPQH | SEQ ID NO: 276 |
| ASSPGLQETQY | SEQ ID NO: 277 |
| ASSTSTDTQY | SEQ ID NO: 278 |
| ASSLDRGTDTQY | SEQ ID NO: 279 |
| ASSLQENTEAF | SEQ ID NO: 280 |
| ASSSLYEQY | SEQ ID NO: 281 |
| ASSPGNTEAF | SEQ ID NO: 282 |
| ASSQDSNQPQH | SEQ ID NO: 283 |
| ASSLTGSYEQY | SEQ ID NO: 284 |
| ASSLAGSSYEQY | SEQ ID NO: 285 |
| ASSFGSNQPQH | SEQ ID NO: 286 |
| ASSLGGSGNTIY | SEQ ID NO: 287 |
| ASSLSLNTEAF | SEQ ID NO: 288 |
| ASSNTDTQY | SEQ ID NO: 289 |
| ASSRTVNTEAF | SEQ ID NO: 290 |
| ASSPAYEQY | SEQ ID NO: 291 |
| ASSPTVNTEAF | SEQ ID NO: 292 |
| ASSRGETQY | SEQ ID NO: 293 |
| ASSLVGTEAF | SEQ ID NO: 294 |
| ASSRDRQETQY | SEQ ID NO: 295 |
| ASSLGGLNTEAF | SEQ ID NO: 296 |
| ASSFGGTEAF | SEQ ID NO: 297 |
| ASSQETQY | SEQ ID NO: 298 |
| ASSLSGSYEQY | SEQ ID NO: 299 |
| ASSPEETQY | SEQ ID NO: 300 |
| ASSPGGNTEAF | SEQ ID NO: 301 |
| ASSLLDTQY | SEQ ID NO: 302 |
| ASSLLTDTQY | SEQ ID NO: 303 |
| ASSSYYEQY | SEQ ID NO: 304 |
| ASSQSTDTQY | SEQ ID NO: 305 |
| ASSFGNTEAF | SEQ ID NO: 306 |
| ASSLTGDTEAF | SEQ ID NO: 307 |
| ASSPSSYNEQF | SEQ ID NO: 308 |
| ASSFGGTDTQY | SEQ ID NO: 309 |
| ASSSDRNTEAF | SEQ ID NO: 310 |
| ASSQDRNTEAF | SEQ ID NO: 311 |
| ASSLGLYNEQF | SEQ ID NO: 312 |
| ASSLTGGNQPQH | SEQ ID NO: 313 |
| ASSLGGNYGYT | SEQ ID NO: 314 |

TABLE I-continued

| Sequence | Sequence ID No |
|---|---|
| ASSPPTDTQY | SEQ ID NO: 315 |
| ASSLAGGQETQY | SEQ ID NO: 316 |
| ASSLTGTDTQY | SEQ ID NO: 317 |
| ASSLGQAYEQY | SEQ ID NO: 318 |
| ASSRDSTDTQY | SEQ ID NO: 319 |
| ASSPTGYEQY | SEQ ID NO: 320 |
| ASSLQGSNQPQH | SEQ ID NO: 321 |
| ASSLTGGTDTQY | SEQ ID NO: 322 |
| ASSYGETQY | SEQ ID NO: 323 |
| ASSPYTDTQY | SEQ ID NO: 324 |
| ASSLDLNTEAF | SEQ ID NO: 325 |
| ASSLTGSNQPQH | SEQ ID NO: 326 |
| ASSLSNEQF | SEQ ID NO: 327 |
| ASSLGTNTEAF | SEQ ID NO: 328 |
| ASSPGADTQY | SEQ ID NO: 329 |
| ASSLTGNYGYT | SEQ ID NO: 330 |
| ASSLAGSNQPQH | SEQ ID NO: 331 |
| ASSSTGNTEAF | SEQ ID NO: 332 |
| ASSLSGGTDTQY | SEQ ID NO: 333 |
| ASSPNTEAF | SEQ ID NO: 334 |
| ASSLGYGYT | SEQ ID NO: 335 |
| ASSLAGGNTEAF | SEQ ID NO: 336 |
| ASSQGGNTEAF | SEQ ID NO: 337 |
| ASSRDRGYEQY | SEQ ID NO: 338 |
| ASSRGTDTQY | SEQ ID NO: 339 |
| ASSLRNTEAF | SEQ ID NO: 340 |
| ASSSRETQY | SEQ ID NO: 341 |
| ASSLGQPQH | SEQ ID NO: 342 |
| ASSLVGDTQY | SEQ ID NO: 343 |
| ASSLTETQY | SEQ ID NO: 344 |
| ASSLGTVNTEAF | SEQ ID NO: 345 |
| ASSQGTDTQY | SEQ ID NO: 346 |
| ASSFYNEQF | SEQ ID NO: 347 |
| ASSSGSTDTQY | SEQ ID NO: 348 |
| ASSLDTEAF | SEQ ID NO: 349 |
| ASSLEGGTEAF | SEQ ID NO: 350 |
| ASSLGLSTDTQY | SEQ ID NO: 351 |
| ASSLGDQPQH | SEQ ID NO: 352 |
| ASSLRENTEAF | SEQ ID NO: 353 |
| ASSLALNTEAF | SEQ ID NO: 354 |
| ASSVTDTQY | SEQ ID NO: 355 |
| ASSLDQETQY | SEQ ID NO: 356 |
| ASSLSGSSYEQY | SEQ ID NO: 357 |
| ASSPKETQY | SEQ ID NO: 358 |
| ASSLSQETQY | SEQ ID NO: 359 |
| ASSLAQETQY | SEQ ID NO: 360 |
| ASSLQNTEAF | SEQ ID NO: 361 |
| ASSLRNEQF | SEQ ID NO: 362 |
| ASSLSGGTEAF | SEQ ID NO: 363 |
| ASSPGGETQY | SEQ ID NO: 364 |
| ASSRDSYNEQF | SEQ ID NO: 365 |
| ASSSSYNEQF | SEQ ID NO: 366 |
| ASSRQGYEQY | SEQ ID NO: 367 |
| ASSLAENTEAF | SEQ ID NO: 368 |
| ASSLYTDTQY | SEQ ID NO: 369 |
| ASSLGQYNEQF | SEQ ID NO: 370 |
| ASSLTLNTEAF | SEQ ID NO: 371 |
| ASSLAGAYEQY | SEQ ID NO: 372 |
| ASSLGGGNTEAF | SEQ ID NO: 373 |
| ASSLQVNTEAF | SEQ ID NO: 374 |
| ASSLAGSSYNEQF | SEQ ID NO: 375 |
| ASSLRGNQPQH | SEQ ID NO: 376 |
| ASSLDRGYEQY | SEQ ID NO: 377 |
| ASSPPGTDTQY | SEQ ID NO: 378 |
| ASSLGTGNQPQH | SEQ ID NO: 379 |
| ASSSRTDTQY | SEQ ID NO: 380 |
| ASSLRVNTEAF | SEQ ID NO: 381 |
| ASSLAGGSYNEQF | SEQ ID NO: 382 |
| ASSPGTGAYEQY | SEQ ID NO: 383 |
| ASSPGSNQPQH | SEQ ID NO: 384 |
| ASSPNTGELF | SEQ ID NO: 385 |
| ASSPGRNTEAF | SEQ ID NO: 386 |
| ASSLTGELF | SEQ ID NO: 387 |
| ASSPDRNYGYT | SEQ ID NO: 388 |
| ASSPGTVNTEAF | SEQ ID NO: 389 |
| ASSLAGGNEQF | SEQ ID NO: 390 |
| ASSQGGTEAF | SEQ ID NO: 391 |
| ASSLDRNYGYT | SEQ ID NO: 392 |

TABLE I-continued

| Sequence | Sequence ID No |
|---|---|
| ASSIQETQY | SEQ ID NO: 393 |
| ASSLGRSYEQY | SEQ ID NO: 394 |
| ASSRGNTEAF | SEQ ID NO: 395 |
| ASSLSGETQY | SEQ ID NO: 396 |
| ASSLDNEQF | SEQ ID NO: 397 |
| ASSSGQNTEAF | SEQ ID NO: 398 |
| ASSPGQGYGYT | SEQ ID NO: 399 |
| ASSPDTDTQY | SEQ ID NO: 400 |
| ASSSGDTQY | SEQ ID NO: 401 |
| ASSPGSTDTQY | SEQ ID NO: 402 |
| ASSPGSSYEQY | SEQ ID NO: 403 |
| ASSLGGGYEQY | SEQ ID NO: 404 |
| ASSLDRGTEAF | SEQ ID NO: 405 |
| ASSGSTDTQY | SEQ ID NO: 406 |
| ASRLNTEAF | SEQ ID NO: 407 |
| ASSLEGTDTQY | SEQ ID NO: 408 |
| ASSQGNTEAF | SEQ ID NO: 409 |
| ASSLAGGNQPQH | SEQ ID NO: 410 |
| ASSLGRTDTQY | SEQ ID NO: 411 |
| ASSLGRSTDTQY | SEQ ID NO: 412 |
| ASSLRGNEQF | SEQ ID NO: 413 |
| ASSPGGNQPQH | SEQ ID NO: 414 |
| ASSLLGNTEAF | SEQ ID NO: 415 |
| ASSPGQNYGYT | SEQ ID NO: 416 |
| ASSTTDTQY | SEQ ID NO: 417 |
| ASSQGDTQY | SEQ ID NO: 418 |
| ASSLGGDQPQH | SEQ ID NO: 419 |
| ASSLGTAYEQY | SEQ ID NO: 420 |
| ASSLGTYNEQF | SEQ ID NO: 421 |
| ASSTQETQY | SEQ ID NO: 422 |
| ASSLGPQETQY | SEQ ID NO: 423 |
| ASSQDRETQY | SEQ ID NO: 424 |
| ASSLAADTQY | SEQ ID NO: 425 |
| ASSLLGNEQF | SEQ ID NO: 426 |
| ASSLGQGTEAF | SEQ ID NO: 427 |
| ASSPGQSYEQY | SEQ ID NO: 428 |
| ASSVQETQY | SEQ ID NO: 429 |
| ASSPNQETQY | SEQ ID NO: 430 |
| ASSFSNQPQH | SEQ ID NO: 431 |
| ASSLGRNQPQH | SEQ ID NO: 432 |
| ASSRGTEAF | SEQ ID NO: 433 |
| ASSFGQNTEAF | SEQ ID NO: 434 |
| ASSLGGDTEAF | SEQ ID NO: 435 |
| ASSPTGGNQPQH | SEQ ID NO: 436 |
| ASSLGSNTEAF | SEQ ID NO: 437 |
| ASSPGTAYEQY | SEQ ID NO: 438 |
| ASSPYQETQY | SEQ ID NO: 439 |
| ASSLGGTYEQY | SEQ ID NO: 440 |
| ASSLGLATDTQY | SEQ ID NO: 441 |
| ASSQGRNTEAF | SEQ ID NO: 442 |
| ASSPTGNYGYT | SEQ ID NO: 443 |
| ASSGQGNTEAF | SEQ ID NO: 444 |
| ASSRTENTEAF | SEQ ID NO: 445 |
| ASSLRYEQY | SEQ ID NO: 446 |
| ASSQGSNQPQH | SEQ ID NO: 447 |
| ASSLARNTEAF | SEQ ID NO: 448 |
| ASSLAGYNEQF | SEQ ID NO: 449 |
| ASSLLNEQF | SEQ ID NO: 450 |
| ASSPLTDTQY | SEQ ID NO: 451 |
| ASSLGSGNTIY | SEQ ID NO: 452 |
| ASSRGDTQY | SEQ ID NO: 453 |
| ASSASYEQY | SEQ ID NO: 454 |
| ASSLEGYGYT | SEQ ID NO: 455 |
| ASSFQGNTEAF | SEQ ID NO: 456 |
| ASSSNTEAF | SEQ ID NO: 457 |
| ASSLTGMNTEAF | SEQ ID NO: 458 |
| ASSLGTGNTEAF | SEQ ID NO: 459 |
| ASSFGGSTDTQY | SEQ ID NO: 460 |
| ASSFSSYEQY | SEQ ID NO: 461 |
| ASSFGGNQPQH | SEQ ID NO: 462 |
| ASSLSGNEQF | SEQ ID NO: 463 |
| ASSQYNEQF | SEQ ID NO: 464 |
| ASSLRSTDTQY | SEQ ID NO: 465 |
| ASSLGGTQY | SEQ ID NO: 466 |
| ASSLGASTDTQY | SEQ ID NO: 467 |
| ASSLAGEETQY | SEQ ID NO: 468 |
| ASSFGNQPQH | SEQ ID NO: 469 |
| ASSLTGLNTEAF | SEQ ID NO: 470 |

TABLE I-continued

| Sequence | Sequence ID No |
|---|---|
| ASSLGSQETQY | SEQ ID NO: 471 |
| ASSLSGDTQY | SEQ ID NO: 472 |
| ASSLTGSTDTQY | SEQ ID NO: 473 |
| ASSSGNQPQH | SEQ ID NO: 474 |
| ASSSSNQPQH | SEQ ID NO: 475 |
| ASSGYNEQF | SEQ ID NO: 476 |
| ASSLARETQY | SEQ ID NO: 477 |
| ASSLVSYEQY | SEQ ID NO: 478 |
| ASSLAGGPDTQY | SEQ ID NO: 479 |
| ASSLTSGTDTQY | SEQ ID NO: 480 |
| ASSLGRETQY | SEQ ID NO: 481 |
| ASSLGQGGTEAF | SEQ ID NO: 482 |
| ASSLSADTQY | SEQ ID NO: 483 |
| ASSSGQGYEQY | SEQ ID NO: 484 |
| ASSLTSYEQY | SEQ ID NO: 485 |
| ASSLAGGETQY | SEQ ID NO: 486 |
| ASSFADTQY | SEQ ID NO: 487 |
| ASSFGRNTEAF | SEQ ID NO: 488 |
| ASSFSGSTDTQY | SEQ ID NO: 489 |
| ASSLVQETQY | SEQ ID NO: 490 |
| ASSHTDTQY | SEQ ID NO: 491 |
| ASSFGSTDTQY | SEQ ID NO: 492 |
| ASSPRGNTEAF | SEQ ID NO: 493 |
| ASSSGQGTDTQY | SEQ ID NO: 494 |
| ASSLGRQETQY | SEQ ID NO: 495 |
| ASSGQGNQPQH | SEQ ID NO: 496 |
| ASSLVSTDTQY | SEQ ID NO: 497 |
| ASSSNYEQY | SEQ ID NO: 498 |
| ASSQAYEQY | SEQ ID NO: 499 |
| ASSLGPNQPQH | SEQ ID NO: 500 |
| ASSLQGSYEQY | SEQ ID NO: 501 |
| ASSPGTEAF | SEQ ID NO: 502 |
| ASSSSSYNEQF | SEQ ID NO: 503 |
| ASSASTDTQY | SEQ ID NO: 504 |
| ASSLGPSTDTQY | SEQ ID NO: 505 |
| ASSLDSYGYT | SEQ ID NO: 506 |
| ASSLRGDTQY | SEQ ID NO: 507 |
| ASSFGSSYEQY | SEQ ID NO: 508 |
| ASSHSYEQY | SEQ ID NO: 509 |
| ASSQGSYEQY | SEQ ID NO: 510 |
| ASSLYQETQY | SEQ ID NO: 511 |
| ASSPGTGNTEAF | SEQ ID NO: 512 |
| ASSPQGNQPQH | SEQ ID NO: 513 |
| ASSTYNEQF | SEQ ID NO: 514 |
| ASSSNTDTQY | SEQ ID NO: 515 |
| ASSPRGYEQY | SEQ ID NO: 516 |
| ASSQGGNQPQH | SEQ ID NO: 517 |
| ASSLGDEQF | SEQ ID NO: 518 |
| ASSLRGGTEAF | SEQ ID NO: 519 |
| ASSLGQSNQPQH | SEQ ID NO: 520 |
| ASSLANEQF | SEQ ID NO: 521 |
| ASSLNSYEQY | SEQ ID NO: 522 |
| ASSPGTYEQY | SEQ ID NO: 523 |
| ASSLGTSYEQY | SEQ ID NO: 524 |
| ASSPGGSYEQY | SEQ ID NO: 525 |
| ASSLGPTDTQY | SEQ ID NO: 526 |
| ASSLGQNQPQH | SEQ ID NO: 527 |
| ASSLGGSTEAF | SEQ ID NO: 528 |
| ASSLAGTYEQY | SEQ ID NO: 529 |
| ASSLLYEQY | SEQ ID NO: 530 |
| ASSLGPSYEQY | SEQ ID NO: 531 |
| ASSSGQGNQPQH | SEQ ID NO: 532 |
| ASSPGTSGYNEQF | SEQ ID NO: 533 |
| ASSSGGTEAF | SEQ ID NO: 534 |
| ASSLGNTIY | SEQ ID NO: 535 |
| ASSLGDSNQPQH | SEQ ID NO: 536 |
| ASSLGQGADTQY | SEQ ID NO: 537 |
| ASSLGGPYEQY | SEQ ID NO: 538 |
| ASSLLGTDTQY | SEQ ID NO: 539 |
| ASSLGTGGYEQY | SEQ ID NO: 540 |
| ASSLGGAYEQY | SEQ ID NO: 541 |
| ASSQGNQPQH | SEQ ID NO: 542 |
| ASSLASNQPQH | SEQ ID NO: 543 |
| ASSLGLSYEQY | SEQ ID NO: 544 |
| ASSLDNQPQH | SEQ ID NO: 545 |
| ASSPSYNEQF | SEQ ID NO: 546 |
| ASRDSNQPQH | SEQ ID NO: 547 |
| ASSLSSGNTIY | SEQ ID NO: 548 |

TABLE I-continued

| Sequence | Sequence ID No |
|---|---|
| ASSFGTEAF | SEQ ID NO: 549 |
| ASSLQGLNTEAF | SEQ ID NO: 550 |
| ASSITDTQY | SEQ ID NO: 551 |
| ASSYSNQPQH | SEQ ID NO: 552 |
| ASSPGGDTQY | SEQ ID NO: 553 |
| ASSLDRDQPQH | SEQ ID NO: 554 |
| ASSPGMNTEAF | SEQ ID NO: 555 |
| ASSLPNQPQH | SEQ ID NO: 556 |
| ASSLGPYNEQF | SEQ ID NO: 557 |
| ASSLRQNTEAF | SEQ ID NO: 558 |
| ASSRNTGELF | SEQ ID NO: 559 |
| ASSPSGSTDTQY | SEQ ID NO: 560 |
| ASSLPGTDTQY | SEQ ID NO: 561 |
| ASSLGQGPYEQY | SEQ ID NO: 562 |
| ASSQGNEQF | SEQ ID NO: 563 |
| ASSQGGYEQY | SEQ ID NO: 564 |
| ASSLLGYEQY | SEQ ID NO: 565 |
| ASSLVGNQPQH | SEQ ID NO: 566 |
| ASSLDRAYEQY | SEQ ID NO: 567 |
| ASSPRGTEAF | SEQ ID NO: 568 |
| ASSLVGSTDTQY | SEQ ID NO: 569 |
| ASSLSPNTEAF | SEQ ID NO: 570 |
| ASSPGPNTEAF | SEQ ID NO: 571 |
| ASSYRGNTEAF | SEQ ID NO: 572 |
| ASSLDRDTEAF | SEQ ID NO: 573 |
| ASSSTVNTEAF | SEQ ID NO: 574 |
| ASSSLTDTQY | SEQ ID NO: 575 |
| ASSLLGQPQH | SEQ ID NO: 576 |
| ASSLAGTEAF | SEQ ID NO: 577 |
| ASSSEETQY | SEQ ID NO: 578 |
| ASSLASYEQY | SEQ ID NO: 579 |
| ASSLSTEAF | SEQ ID NO: 580 |
| ASSPGQLNTEAF | SEQ ID NO: 581 |
| ASSRSSYEQY | SEQ ID NO: 582 |
| ASSPGNEQF | SEQ ID NO: 583 |
| ASSLQGMNTEAF | SEQ ID NO: 584 |
| ASSQTDTQY | SEQ ID NO: 585 |
| ASSQGTEAF | SEQ ID NO: 586 |
| ASSFSETQY | SEQ ID NO: 587 |
| ASSPSGSSYNEQF | SEQ ID NO: 588 |
| ASSLDSNYGYT | SEQ ID NO: 589 |
| ASSLGNTGELF | SEQ ID NO: 590 |
| ASSEGYEQY | SEQ ID NO: 591 |
| ASSLTGVNTEAF | SEQ ID NO: 592 |
| ASSQGMNTEAF | SEQ ID NO: 593 |
| ASSYYNEQF | SEQ ID NO: 594 |
| ASSFEETQY | SEQ ID NO: 595 |
| ASSLGEKLF | SEQ ID NO: 596 |
| ASRSTDTQY | SEQ ID NO: 597 |
| ASSPDSNYGYT | SEQ ID NO: 598 |
| ASSLGTGAYEQY | SEQ ID NO: 599 |
| ASSLTGDQPQH | SEQ ID NO: 600 |
| ASSLPSTDTQY | SEQ ID NO: 601 |
| ASSLQGGNQPQH | SEQ ID NO: 602 |
| ASSLDRETQY | SEQ ID NO: 603 |
| ASSRDRAYEQY | SEQ ID NO: 604 |
| ASSLTSGSYEQY | SEQ ID NO: 605 |
| ASSRGNEQF | SEQ ID NO: 606 |
| ASSFGGSYEQY | SEQ ID NO: 607 |
| ASSQDSYEQY | SEQ ID NO: 608 |
| ASSLGGNTIY | SEQ ID NO: 609 |
| ASSLLAGGTDTQY | SEQ ID NO: 610 |
| ASSVGGNTEAF | SEQ ID NO: 611 |
| ASSQNTEAF | SEQ ID NO: 612 |
| ASSLELNTEAF | SEQ ID NO: 613 |
| ASSFTGNTEAF | SEQ ID NO: 614 |
| ASSSGSSYNEQF | SEQ ID NO: 615 |
| ASSSGNTIY | SEQ ID NO: 616 |
| ASSLDMNTEAF | SEQ ID NO: 617 |
| ASSPSGANVLT | SEQ ID NO: 618 |
| ASRGNTEAF | SEQ ID NO: 619 |
| ASSPGLATDTQY | SEQ ID NO: 620 |
| ASSLQGTEAF | SEQ ID NO: 621 |
| ASSFDSNQPQH | SEQ ID NO: 622 |
| ASSAYNEQF | SEQ ID NO: 623 |
| ASSLDYNEQF | SEQ ID NO: 624 |
| ASSLVGGNTEAF | SEQ ID NO: 625 |
| ASSLSGSNQPQH | SEQ ID NO: 626 |

TABLE I-continued

| Sequence | Sequence ID No |
|---|---|
| ASSGTGNQPQH | SEQ ID NO: 627 |
| ASSRQGNQPQH | SEQ ID NO: 628 |
| ASSQGQNTEAF | SEQ ID NO: 629 |
| ASSLSMNTEAF | SEQ ID NO: 630 |
| ASSTSYEQY | SEQ ID NO: 631 |
| ASSLRGQETQY | SEQ ID NO: 632 |
| ASSPGQTYEQY | SEQ ID NO: 633 |
| ASSFSGANVLT | SEQ ID NO: 634 |
| ASSFRGNTEAF | SEQ ID NO: 635 |
| ASSLDRGNTEAF | SEQ ID NO: 636 |
| ASSPDRNQPQH | SEQ ID NO: 637 |
| ASSVYNEQF | SEQ ID NO: 638 |
| ASSPGTGYEQY | SEQ ID NO: 639 |
| ASSPRGTDTQY | SEQ ID NO: 640 |
| ASSLRGSTDTQY | SEQ ID NO: 641 |
| ASSPGVNTEAF | SEQ ID NO: 642 |
| ASSLGGTGELF | SEQ ID NO: 643 |
| ASSLGGGSYEQY | SEQ ID NO: 644 |
| ASSLLGETQY | SEQ ID NO: 645 |
| ASSVSYEQY | SEQ ID NO: 646 |
| ASSSGQGNTEAF | SEQ ID NO: 647 |
| ASSLNYGYT | SEQ ID NO: 648 |
| ASSSGNTEAF | SEQ ID NO: 649 |
| ASSLAGMNTEAF | SEQ ID NO: 650 |
| ASSPGYNEQF | SEQ ID NO: 651 |
| ASSPNYEQY | SEQ ID NO: 652 |
| ASSSTGYEQY | SEQ ID NO: 653 |
| ASSDSNQPQH | SEQ ID NO: 654 |
| ASRRNTEAF | SEQ ID NO: 655 |
| ASSNSYEQY | SEQ ID NO: 656 |
| ASSSGTGSYEQY | SEQ ID NO: 657 |
| ASSLGYTEAF | SEQ ID NO: 658 |
| ASSLWGNTEAF | SEQ ID NO: 659 |
| ASSLGLAGTDTQY | SEQ ID NO: 660 |
| ASSLAGLNTEAF | SEQ ID NO: 661 |
| ASSFSGNTEAF | SEQ ID NO: 662 |
| ASSSSGNTIY | SEQ ID NO: 663 |
| ASSSGGYEQY | SEQ ID NO: 664 |
| ASSRGLNTEAF | SEQ ID NO: 665 |
| ASSLSSGANVLT | SEQ ID NO: 666 |
| ASSLEMNTEAF | SEQ ID NO: 667 |
| ASSLGDEQY | SEQ ID NO: 668 |
| ASSLTGSSYEQY | SEQ ID NO: 669 |
| ASSSGLNTEAF | SEQ ID NO: 670 |
| ASSLGQNTGELF | SEQ ID NO: 671 |
| ASSLANTEAF | SEQ ID NO: 672 |
| ASSPLNTEAF | SEQ ID NO: 673 |
| ASSPGLSTDTQY | SEQ ID NO: 674 |
| ASSPRDTQY | SEQ ID NO: 675 |
| ASSLAGANVLT | SEQ ID NO: 676 |
| ASSGSYEQY | SEQ ID NO: 677 |
| ASSLSGQPQH | SEQ ID NO: 678 |
| ASSLQGNYGYT | SEQ ID NO: 679 |
| ASSFLETQY | SEQ ID NO: 680 |
| ASSLSGQETQY | SEQ ID NO: 681 |
| ASSFDRNTEAF | SEQ ID NO: 682 |
| ASSGTGGNQPQH | SEQ ID NO: 683 |
| ASSLEGTEAF | SEQ ID NO: 684 |
| ASSLENTEAF | SEQ ID NO: 685 |
| ASSLVVNTEAF | SEQ ID NO: 686 |
| ASSLTNTEAF | SEQ ID NO: 687 |
| ASSRDRGTDTQY | SEQ ID NO: 688 |
| ASSFRGTDTQY | SEQ ID NO: 689 |
| ASSLAGQPQH | SEQ ID NO: 690 |
| ASSPGTSTDTQY | SEQ ID NO: 691 |
| ASSLVGQPQH | SEQ ID NO: 692 |
| ASSLDRVNTEAF | SEQ ID NO: 693 |
| ASSNQETQY | SEQ ID NO: 694 |
| ASSLGQGNYGYT | SEQ ID NO: 695 |
| ASSQGVNTEAF | SEQ ID NO: 696 |
| ASSPGQGPYEQY | SEQ ID NO: 697 |
| ASSGGYEQY | SEQ ID NO: 698 |
| ASSLAGAYNEQF | SEQ ID NO: 699 |
| ASSATDTQY | SEQ ID NO: 700 |
| ASSSADTQY | SEQ ID NO: 701 |
| ASSLVPDTQY | SEQ ID NO: 702 |
| ASSLERNTEAF | SEQ ID NO: 703 |
| ASSLDRGNQPQH | SEQ ID NO: 704 |

TABLE I-continued

| Sequence | Sequence ID No |
|---|---|
| ASSLYYEQY | SEQ ID NO: 705 |
| ASSLVGGTDTQY | SEQ ID NO: 706 |
| ASSPRTGNTEAF | SEQ ID NO: 707 |
| ASSQDRNQPQH | SEQ ID NO: 708 |
| ASSSGGTDTQY | SEQ ID NO: 709 |
| ASSLVYEQY | SEQ ID NO: 710 |
| ASSLRTEAF | SEQ ID NO: 711 |
| ASSLLGNQPQH | SEQ ID NO: 712 |
| ASSLVGGTEAF | SEQ ID NO: 713 |
| ASSLGLAGYNEQF | SEQ ID NO: 714 |
| ASSFGVNTEAF | SEQ ID NO: 715 |
| ASSLLGDTQY | SEQ ID NO: 716 |
| ASSQTYEQY | SEQ ID NO: 717 |
| ASSPGTGTYEQY | SEQ ID NO: 718 |
| ASSFGLNTEAF | SEQ ID NO: 719 |
| ASSPGTSYEQY | SEQ ID NO: 720 |
| ASSLLGTEAF | SEQ ID NO: 721 |
| ASSLRGSYEQY | SEQ ID NO: 722 |
| ASSLRGETQY | SEQ ID NO: 723 |
| ASSLGQANTEAF | SEQ ID NO: 724 |
| ASSLDRYEQY | SEQ ID NO: 725 |
| ASSPGPYEQY | SEQ ID NO: 726 |
| ASSSYSNQPQH | SEQ ID NO: 727 |
| ASSLQGYGYT | SEQ ID NO: 728 |
| ASSLGRNYGYT | SEQ ID NO: 729 |
| ASSLETDTQY | SEQ ID NO: 730 |
| ASSLGGGETQY | SEQ ID NO: 731 |
| ASSFRDTQY | SEQ ID NO: 732 |
| ASSLASSYEQY | SEQ ID NO: 733 |
| ASSQADTQY | SEQ ID NO: 734 |
| ASSLGRMNTEAF | SEQ ID NO: 735 |
| ASSLQGNEQF | SEQ ID NO: 736 |
| ASSLGQVNTEAF | SEQ ID NO: 737 |
| ASSLRGSNQPQH | SEQ ID NO: 738 |
| ASSLVGSYEQY | SEQ ID NO: 739 |
| ASSGTDTQY | SEQ ID NO: 740 |
| ASSLGYSNQPQH | SEQ ID NO: 741 |
| ASSLGGVNTEAF | SEQ ID NO: 742 |
| ASSLTYNEQF | SEQ ID NO: 743 |
| ASSLVLNTEAF | SEQ ID NO: 744 |
| ASSPDSYNEQF | SEQ ID NO: 745 |
| ASSLGQGTYEQY | SEQ ID NO: 746 |
| ASSLTRNTEAF | SEQ ID NO: 747 |
| ASSLQGDTEAF | SEQ ID NO: 748 |
| ASSLTGGSYEQY | SEQ ID NO: 749 |
| ASSYSSYEQY | SEQ ID NO: 750 |
| ASSSTTDTQY | SEQ ID NO: 751 |
| ASSLDGNYGYT | SEQ ID NO: 752 |
| ASSLVSNQPQH | SEQ ID NO: 753 |
| ASSPGGNEQF | SEQ ID NO: 754 |
| ASSGGTDTQY | SEQ ID NO: 755 |
| ASSPRGETQY | SEQ ID NO: 756 |
| ASSLVSDTQY | SEQ ID NO: 757 |
| ASSPYSNQPQH | SEQ ID NO: 758 |
| ASSLGRYNEQF | SEQ ID NO: 759 |
| ASSRTGGTEAF | SEQ ID NO: 760 |
| ASSSLNTEAF | SEQ ID NO: 761 |
| ASSPGGSYNEQF | SEQ ID NO: 762 |
| ASSLAGGPYNEQF | SEQ ID NO: 763 |
| ASSLEADTQY | SEQ ID NO: 764 |
| ASSLGGGQPQH | SEQ ID NO: 765 |
| ASSRTANTEAF | SEQ ID NO: 766 |
| ASSLEYEQY | SEQ ID NO: 767 |
| ASSPPSSYEQY | SEQ ID NO: 768 |
| ASSLETQY | SEQ ID NO: 769 |
| ASSLGRTYEQY | SEQ ID NO: 770 |
| ASSEYNEQF | SEQ ID NO: 771 |
| ASSLLNQPQH | SEQ ID NO: 772 |
| ASSYGYEQY | SEQ ID NO: 773 |
| ASSLLAGGYNEQF | SEQ ID NO: 774 |
| ASSQDRDQPQH | SEQ ID NO: 775 |
| ASSLGRDTQY | SEQ ID NO: 776 |
| ASSLSSSYEQY | SEQ ID NO: 777 |
| ASSLGSSTDTQY | SEQ ID NO: 778 |
| ASSPGQAYEQY | SEQ ID NO: 779 |
| ASSYGGNTEAF | SEQ ID NO: 780 |
| ASSLRGDTEAF | SEQ ID NO: 781 |
| ASSLSGSYNEQF | SEQ ID NO: 782 |

TABLE I-continued

| Sequence | Sequence ID No |
|---|---|
| ASSLEGDTQY | SEQ ID NO: 783 |
| ASSLEGETQY | SEQ ID NO: 784 |
| ASSLGQGNSPLH | SEQ ID NO: 785 |
| ASSFSGNTIY | SEQ ID NO: 786 |
| ASSFGNEQF | SEQ ID NO: 787 |
| ASSLRSNQPQH | SEQ ID NO: 788 |
| ASSLDPNTEAF | SEQ ID NO: 789 |
| ASSDTDTQY | SEQ ID NO: 790 |
| ASSLGRGTEAF | SEQ ID NO: 791 |
| ASSLGSSGNTIY | SEQ ID NO: 792 |
| ASSLKDTQY | SEQ ID NO: 793 |
| ASSLAANTEAF | SEQ ID NO: 794 |
| ASSLAGNTIY | SEQ ID NO: 795 |
| ASSPGSYNEQF | SEQ ID NO: 796 |
| ASSSSDTQY | SEQ ID NO: 797 |
| ASSLTSNQPQH | SEQ ID NO: 798 |
| ASSLDSNTEAF | SEQ ID NO: 799 |
| ASSQDRGQPQH | SEQ ID NO: 800 |
| ASSLTGNEQF | SEQ ID NO: 801 |
| ASSPTGNQPQH | SEQ ID NO: 802 |
| ASSLQGANTEAF | SEQ ID NO: 803 |
| ASSLGQGGQPQH | SEQ ID NO: 804 |
| ASSSRYEQY | SEQ ID NO: 805 |
| ASSPRNTEAF | SEQ ID NO: 806 |
| ASSLRLNTEAF | SEQ ID NO: 807 |
| ASSLNRNTEAF | SEQ ID NO: 808 |
| ASSLGRTEAF | SEQ ID NO: 809 |
| ASSFLNTEAF | SEQ ID NO: 810 |
| ASSLAGSGNTIY | SEQ ID NO: 811 |
| ASSYRENTEAF | SEQ ID NO: 812 |
| ASSPPSYEQY | SEQ ID NO: 813 |
| ASSLTGQETQY | SEQ ID NO: 814 |
| ASSLRADTQY | SEQ ID NO: 815 |
| ASSLGGRETQY | SEQ ID NO: 816 |
| ASSLLSTDTQY | SEQ ID NO: 817 |
| ASSLGTGYEQY | SEQ ID NO: 818 |
| ASSPPGETQY | SEQ ID NO: 819 |
| ASSLSTGELF | SEQ ID NO: 820 |
| ASSPGSSYNEQF | SEQ ID NO: 821 |
| ASSLSGTEAF | SEQ ID NO: 822 |
| ASSIGETQY | SEQ ID NO: 823 |
| ASSLTSGSYNEQF | SEQ ID NO: 824 |
| ASSLSENTEAF | SEQ ID NO: 825 |
| ASSSNYGYT | SEQ ID NO: 826 |
| ASSQQGNTEAF | SEQ ID NO: 827 |
| ASSSDSNQPQH | SEQ ID NO: 828 |
| ASSSSGANVLT | SEQ ID NO: 829 |
| ASSLGLAGDTQY | SEQ ID NO: 830 |
| ASSSGSSYEQY | SEQ ID NO: 831 |
| ASSLGVSYEQY | SEQ ID NO: 832 |
| ASSPGYGYT | SEQ ID NO: 833 |
| ASSPSNQPQH | SEQ ID NO: 834 |
| ASSLGGRTDTQY | SEQ ID NO: 835 |
| ASSRTGGNQPQH | SEQ ID NO: 836 |
| ASSVSTDTQY | SEQ ID NO: 837 |
| ASSLRGLNTEAF | SEQ ID NO: 838 |
| ASSSTGGTEAF | SEQ ID NO: 839 |
| ASSQEETQY | SEQ ID NO: 840 |
| ASSLGGEAF | SEQ ID NO: 841 |
| ASSLNQPQH | SEQ ID NO: 842 |
| ASSRGGTEAF | SEQ ID NO: 843 |
| ASSPGQGNYGYT | SEQ ID NO: 844 |
| ASSLAGNYGYT | SEQ ID NO: 845 |
| ASSPLYEQY | SEQ ID NO: 846 |
| ASSLGTGTDTQY | SEQ ID NO: 847 |
| ASSLGRDQPQH | SEQ ID NO: 848 |
| ASSLDTGELF | SEQ ID NO: 849 |
| ASSLGTSGYNEQF | SEQ ID NO: 850 |
| ASSQSSYEQY | SEQ ID NO: 851 |
| ASSLGGGQETQY | SEQ ID NO: 852 |
| ASSPQGNEQF | SEQ ID NO: 853 |
| ASSLVRNTEAF | SEQ ID NO: 854 |
| ASSPGQMNTEAF | SEQ ID NO: 855 |
| ASSLGGGSYNEQF | SEQ ID NO: 856 |
| ASSLRGGTDTQY | SEQ ID NO: 857 |
| ASSPGAYEQY | SEQ ID NO: 858 |
| ASSPRGDTQY | SEQ ID NO: 859 |
| ASSFGGSNQPQH | SEQ ID NO: 860 |

TABLE I-continued

| Sequence | Sequence ID No |
|---|---|
| ASSLEGQPQH | SEQ ID NO: 861 |
| ASSLGQNNEQF | SEQ ID NO: 862 |
| ASSLASYNEQF | SEQ ID NO: 863 |
| ASSYGGTEAF | SEQ ID NO: 864 |
| ASSPSDTQY | SEQ ID NO: 865 |
| ASSLGQGQETQY | SEQ ID NO: 866 |
| ASSSNTGELF | SEQ ID NO: 867 |
| ASSLVRETQY | SEQ ID NO: 868 |
| ASSSYQETQY | SEQ ID NO: 869 |
| ASSLGGYTEAF | SEQ ID NO: 870 |
| ASSLDSSYNEQF | SEQ ID NO: 871 |
| ASSPPNQPQH | SEQ ID NO: 872 |
| ASSLRNQPQH | SEQ ID NO: 873 |
| ASSFSSNQPQH | SEQ ID NO: 874 |
| ASSLVGSNQPQH | SEQ ID NO: 875 |
| ASSPGTGYGYT | SEQ ID NO: 876 |
| ASSPDRGNQPQH | SEQ ID NO: 877 |
| ASSDYNEQF | SEQ ID NO: 878 |
| ASSQDRGYEQY | SEQ ID NO: 879 |
| ASSPGQSTDTQY | SEQ ID NO: 880 |
| ASSYSGNTEAF | SEQ ID NO: 881 |
| ASSLSNTEAF | SEQ ID NO: 882 |
| ASSLDRGYGYT | SEQ ID NO: 883 |
| ASSPRSTDTQY | SEQ ID NO: 884 |
| ASSLGVNQPQH | SEQ ID NO: 885 |
| ASSPGQETQY | SEQ ID NO: 886 |
| ASSESYEQY | SEQ ID NO: 887 |
| ASSLTQETQY | SEQ ID NO: 888 |
| ASSGQLNTEAF | SEQ ID NO: 889 |
| ASSPPGNTEAF | SEQ ID NO: 890 |
| ASSLLADTQY | SEQ ID NO: 891 |
| ASSPNSYEQY | SEQ ID NO: 892 |
| ASSLGRGTDTQY | SEQ ID NO: 893 |
| ASSLNQETQY | SEQ ID NO: 894 |
| ASSLTGYNEQF | SEQ ID NO: 895 |
| ASSSSGSSYNEQF | SEQ ID NO: 896 |
| ASSLRMNTEAF | SEQ ID NO: 897 |
| ASSLITDTQY | SEQ ID NO: 898 |
| ASSLGVQETQY | SEQ ID NO: 899 |
| ASSLTGTYEQY | SEQ ID NO: 900 |
| ASSLESNQPQH | SEQ ID NO: 901 |
| ASSLVENTEAF | SEQ ID NO: 902 |
| ASSTGNTEAF | SEQ ID NO: 903 |
| ASSLGSTEAF | SEQ ID NO: 904 |
| ASSLGGSQETQY | SEQ ID NO: 905 |
| ASSLAGVNTEAF | SEQ ID NO: 906 |
| ASSSRDTQY | SEQ ID NO: 907 |
| ASSPTENTEAF | SEQ ID NO: 908 |
| ASSRGSYEQY | SEQ ID NO: 909 |
| ASSPGGNQPQH | SEQ ID NO: 910 |
| ASSPADTQY | SEQ ID NO: 911 |
| ASSLAGYGYT | SEQ ID NO: 912 |
| ASSLGVTDTQY | SEQ ID NO: 913 |
| ASSPGGGTEAF | SEQ ID NO: 914 |
| ASSLGVYEQY | SEQ ID NO: 915 |
| ASRENTEAF | SEQ ID NO: 916 |
| ASSLTGGYEQY | SEQ ID NO: 917 |
| ASSLAGEQY | SEQ ID NO: 918 |
| ASSLGLNQPQH | SEQ ID NO: 919 |
| ASSYRETQY | SEQ ID NO: 920 |
| ASSSGQGYGYT | SEQ ID NO: 921 |
| ASSQGGTDTQY | SEQ ID NO: 922 |
| ASSLTSGSTDTQY | SEQ ID NO: 923 |
| ASSLYTEAF | SEQ ID NO: 924 |
| ASSPTGSYEQY | SEQ ID NO: 925 |
| ASSRTYEQY | SEQ ID NO: 926 |
| ASSLAGDQPQH | SEQ ID NO: 927 |
| ASSLQMNTEAF | SEQ ID NO: 928 |
| ASSPPGSYEQY | SEQ ID NO: 929 |
| ASSRTGYEQY | SEQ ID NO: 930 |
| ASSLLSYEQY | SEQ ID NO: 931 |
| ASSLGRDTEAF | SEQ ID NO: 932 |
| ASSQGQGYEQY | SEQ ID NO: 933 |
| ASSLRRNTEAF | SEQ ID NO: 934 |
| ASSLDRSTDTQY | SEQ ID NO: 935 |
| ASSLNEQF | SEQ ID NO: 936 |
| ASSLGGANTEAF | SEQ ID NO: 937 |
| ASSLDSQETQY | SEQ ID NO: 938 |

TABLE I-continued

| Sequence | Sequence ID No |
|---|---|
| ASSPDRGYGYT | SEQ ID NO: 939 |
| ASSLGANYGYT | SEQ ID NO: 940 |
| ASSLGSGANVLT | SEQ ID NO: 941 |
| ASSLGGGNEQF | SEQ ID NO: 942 |
| ASSGETQY | SEQ ID NO: 943 |
| ASSYGNTEAF | SEQ ID NO: 944 |
| ASSPTSTDTQY | SEQ ID NO: 945 |
| ASSFNTEAF | SEQ ID NO: 946 |
| ASSLGQGSYNEQF | SEQ ID NO: 947 |
| ASTSTDTQY | SEQ ID NO: 948 |
| ASSLGLAYEQY | SEQ ID NO: 949 |
| ASSPSGYEQY | SEQ ID NO: 950 |
| ASSLRGQPQH | SEQ ID NO: 951 |
| ASSLDRSYEQY | SEQ ID NO: 952 |
| ASSLDRTDTQY | SEQ ID NO: 953 |
| ASSSGSYNEQF | SEQ ID NO: 954 |
| ASSLSGELF | SEQ ID NO: 955 |
| ASSSQGNQPQH | SEQ ID NO: 956 |
| ASSLGTGGTEAF | SEQ ID NO: 957 |
| ASSLQGDQPQH | SEQ ID NO: 958 |
| ASSGDSNQPQH | SEQ ID NO: 959 |
| ASSPGGQETQY | SEQ ID NO: 960 |
| ASSGQETQY | SEQ ID NO: 961 |
| ASSLFTDTQY | SEQ ID NO: 962 |
| ASSLGAEAF | SEQ ID NO: 963 |
| ASSFKETQY | SEQ ID NO: 964 |
| ASSGQGTDTQY | SEQ ID NO: 965 |
| ASSRDTEAF | SEQ ID NO: 966 |
| ASSPGTDYGYT | SEQ ID NO: 967 |
| ASSSGQQETQY | SEQ ID NO: 968 |
| ASSRTGSYEQY | SEQ ID NO: 969 |
| ASSLGGNTGELF | SEQ ID NO: 970 |
| ASSIYNEQF | SEQ ID NO: 971 |
| ASSLGAYNEQF | SEQ ID NO: 972 |
| ASSLGLYEQY | SEQ ID NO: 973 |
| ASSLGRGNTEAF | SEQ ID NO: 974 |
| ASSPDRDQPQH | SEQ ID NO: 975 |
| ASSFRGTEAF | SEQ ID NO: 976 |
| ASSGQGYEQY | SEQ ID NO: 977 |
| ASSRGGNTEAF | SEQ ID NO: 978 |
| ASRGQGNQPQH | SEQ ID NO: 979 |
| ASSLGPEAF | SEQ ID NO: 980 |
| ASSLEGSNQPQH | SEQ ID NO: 981 |
| ASSPTGGTEAF | SEQ ID NO: 982 |
| ASSFRNTEAF | SEQ ID NO: 983 |
| ASSQDRGTEAF | SEQ ID NO: 984 |
| ASSLGRLNTEAF | SEQ ID NO: 985 |
| ASSSPSTDTQY | SEQ ID NO: 986 |
| ASSRQENTEAF | SEQ ID NO: 987 |
| ASSREETQY | SEQ ID NO: 988 |
| ASSLKGNTEAF | SEQ ID NO: 989 |
| ASSPSQETQY | SEQ ID NO: 990 |
| ASSPDYEQY | SEQ ID NO: 991 |
| ASSLGLTDTQY | SEQ ID NO: 992 |
| ASSRTSGTDTQY | SEQ ID NO: 993 |
| ASSRGGTDTQY | SEQ ID NO: 994 |
| ASSPNNEQF | SEQ ID NO: 995 |
| ASSRDRSYEQY | SEQ ID NO: 996 |
| ASSPGQGTYEQY | SEQ ID NO: 997 |
| ASSLGLAGGNEQF | SEQ ID NO: 998 |
| ASSGSSYEQY | SEQ ID NO: 999 |
| ASSSQGGTEAF | SEQ ID NO: 1000 |
| ASSLGLAADTQY | SEQ ID NO: 1001 |
| ASSSDTDTQY | SEQ ID NO: 1002 |
| ASSLTGDTQY | SEQ ID NO: 1003 |
| ASSFGGYEQY | SEQ ID NO: 1004 |
| ASSSGNEQF | SEQ ID NO: 1005 |
| ASSLSGYGYT | SEQ ID NO: 1006 |
| ASSLTGETQY | SEQ ID NO: 1007 |
| ASSLPGNTEAF | SEQ ID NO: 1008 |
| ASSPGLSYEQY | SEQ ID NO: 1009 |
| ASSSFYEQY | SEQ ID NO: 1010 |
| ASSLSGGNQPQH | SEQ ID NO: 1011 |
| ASSPGLAGTDTQY | SEQ ID NO: 1012 |
| ASSGSSYNEQF | SEQ ID NO: 1013 |
| ASSSGANVLT | SEQ ID NO: 1014 |
| ASSLSANTEAF | SEQ ID NO: 1015 |
| ASSLGSEQY | SEQ ID NO: 1016 |

TABLE I-continued

| Sequence | Sequence ID No |
|---|---|
| ASSLGRNEQF | SEQ ID NO: 1017 |
| ASSSGTGAYEQY | SEQ ID NO: 1018 |
| ASSFNTGELF | SEQ ID NO: 1019 |
| ASSLTPNTEAF | SEQ ID NO: 1020 |
| ASSLSGGNTEAF | SEQ ID NO: 1021 |
| ASSPGNQPQH | SEQ ID NO: 1022 |
| ASSLGNSPLH | SEQ ID NO: 1023 |
| ASSLRQGNQPQH | SEQ ID NO: 1024 |
| ASSPGTGPYEQY | SEQ ID NO: 1025 |
| ASSLGRAYEQY | SEQ ID NO: 1026 |
| ASSSGTEAF | SEQ ID NO: 1027 |
| ASSLGGSGANVLT | SEQ ID NO: 1028 |
| ASSLTGTEAF | SEQ ID NO: 1029 |
| ASSSNQPQH | SEQ ID NO: 1030 |
| ASSFSGTDTQY | SEQ ID NO: 1031 |
| ASSPGTSGYEQY | SEQ ID NO: 1032 |
| ASSLDGTDTQY | SEQ ID NO: 1033 |
| ASSPTSYEQY | SEQ ID NO: 1034 |
| ASSLEGNEQF | SEQ ID NO: 1035 |
| ASSLQGGNTEAF | SEQ ID NO: 1036 |
| ASSRQGTDTQY | SEQ ID NO: 1037 |
| ASSSGYNEQF | SEQ ID NO: 1038 |
| ASSLDRYNEQF | SEQ ID NO: 1039 |
| ASSPGQGYNEQF | SEQ ID NO: 1040 |
| ASSLGQTNTEAF | SEQ ID NO: 1041 |
| ASSPGLYNEQF | SEQ ID NO: 1042 |
| ASSLQLNTEAF | SEQ ID NO: 1043 |
| ASSPRGNEQF | SEQ ID NO: 1044 |
| ASSPRDSSYEQY | SEQ ID NO: 1045 |
| ASSSGYGYT | SEQ ID NO: 1046 |
| ASSLTGSGNTIY | SEQ ID NO: 1047 |
| ASSFGGSSYEQY | SEQ ID NO: 1048 |
| ASSLLAGTDTQY | SEQ ID NO: 1049 |
| ASSLGGPDTQY | SEQ ID NO: 1050 |
| ASSLGLGTDTQY | SEQ ID NO: 1051 |
| ASSPQGGTEAF | SEQ ID NO: 1052 |
| ASSLQGSTDTQY | SEQ ID NO: 1053 |
| ASSLAGATDTQY | SEQ ID NO: 1054 |
| ASSLGRGYEQY | SEQ ID NO: 1055 |
| ASSLGLAGGTDTQY | SEQ ID NO: 1056 |
| ASSLEANTEAF | SEQ ID NO: 1057 |
| ASSLQGSGNTIY | SEQ ID NO: 1058 |
| ASSDQETQY | SEQ ID NO: 1059 |
| ASSFGGGTEAF | SEQ ID NO: 1060 |
| ASSPGPSYEQY | SEQ ID NO: 1061 |
| ASRGQGNTEAF | SEQ ID NO: 1062 |
| ASSLGTTDTQY | SEQ ID NO: 1063 |
| ASSLGDYGYT | SEQ ID NO: 1064 |
| ASSLRGSGNTIY | SEQ ID NO: 1065 |
| ASSFGSYEQY | SEQ ID NO: 1066 |
| ASSLGQGYNEQF | SEQ ID NO: 1067 |
| ASSPQGSNQPQH | SEQ ID NO: 1068 |
| ASSRTGNQPQH | SEQ ID NO: 1069 |
| ASSLGQGGYEQY | SEQ ID NO: 1070 |
| ASSPTGSNQPQH | SEQ ID NO: 1071 |
| ASSLGRYEQY | SEQ ID NO: 1072 |
| ASSSGQGAYEQY | SEQ ID NO: 1073 |
| ASSRQGGTEAF | SEQ ID NO: 1074 |
| ASSLGDYEQY | SEQ ID NO: 1075 |
| ASSPDSSYEQY | SEQ ID NO: 1076 |
| ASSYRGTEAF | SEQ ID NO: 1077 |
| ASSLGDSYEQY | SEQ ID NO: 1078 |
| ASSRTSGSYEQY | SEQ ID NO: 1079 |
| ASSLRGEQY | SEQ ID NO: 1080 |
| ASSRGGNQPQH | SEQ ID NO: 1081 |
| ASSLTGDYGYT | SEQ ID NO: 1082 |
| ASSYSGYEQY | SEQ ID NO: 1083 |
| ASSQGGEQY | SEQ ID NO: 1084 |
| ASSLAGDTEAF | SEQ ID NO: 1085 |
| ASSYSGETQY | SEQ ID NO: 1086 |
| ASSPSETQY | SEQ ID NO: 1087 |
| ASSSGQSYEQY | SEQ ID NO: 1088 |
| ASSYGQNTEAF | SEQ ID NO: 1089 |
| ASSFGQGYEQY | SEQ ID NO: 1090 |
| ASSRQGSNQPQH | SEQ ID NO: 1091 |
| ASSPGGSNQPQH | SEQ ID NO: 1092 |
| ASSLGTGTYEQY | SEQ ID NO: 1093 |
| ASSFLDTQY | SEQ ID NO: 1094 |

TABLE I-continued

| Sequence | Sequence ID No |
|---|---|
| ASSLRSSYEQY | SEQ ID NO: 1095 |
| ASSFSGSSYNEQF | SEQ ID NO: 1096 |
| ASSPGGGTDTQY | SEQ ID NO: 1097 |
| ASRQGNQPQH | SEQ ID NO: 1098 |
| ASSLTGAYEQY | SEQ ID NO: 1099 |
| ASSFPNQPQH | SEQ ID NO: 1100 |
| ASSLDRGSYEQY | SEQ ID NO: 1101 |
| ASSSTGGNQPQH | SEQ ID NO: 1102 |
| ASSLGGEETQY | SEQ ID NO: 1103 |
| ASSLVGQETQY | SEQ ID NO: 1104 |
| ASSRDREETQY | SEQ ID NO: 1105 |
| ASSYRNTEAF | SEQ ID NO: 1106 |
| ASSLGATDTQY | SEQ ID NO: 1107 |
| ASSLTSSYEQY | SEQ ID NO: 1108 |
| ASSLDRGQPQH | SEQ ID NO: 1109 |
| ASSLDRQETQY | SEQ ID NO: 1110 |
| ASSLSPDTQY | SEQ ID NO: 1111 |
| ASSLSGYNEQF | SEQ ID NO: 1112 |
| ASSLGQETQY | SEQ ID NO: 1113 |
| ASSQTGNTEAF | SEQ ID NO: 1114 |
| ASSRGNQPQH | SEQ ID NO: 1115 |
| ASSPDGNYGYT | SEQ ID NO: 1116 |
| ASSGGTEAF | SEQ ID NO: 1117 |
| ASSLAGGSTDTQY | SEQ ID NO: 1118 |
| ASSLLGGTEAF | SEQ ID NO: 1119 |
| ASSQGYGYT | SEQ ID NO: 1120 |
| ASSSGTANTEAF | SEQ ID NO: 1121 |
| ASSGTVNTEAF | SEQ ID NO: 1122 |
| ASSLTGGYGYT | SEQ ID NO: 1123 |
| ASSQNTGELF | SEQ ID NO: 1124 |
| ASSFGENTEAF | SEQ ID NO: 1125 |
| ASSLAASTDTQY | SEQ ID NO: 1126 |
| ASSSPNQPQH | SEQ ID NO: 1127 |
| ASSQGPYEQY | SEQ ID NO: 1128 |
| ASSLARTDTQY | SEQ ID NO: 1129 |
| ASSGDSYEQY | SEQ ID NO: 1130 |
| ASSLDSSNQPQH | SEQ ID NO: 1131 |
| ASSFSNEQF | SEQ ID NO: 1132 |
| ASSLGSYGYT | SEQ ID NO: 1133 |
| ASSLSGGYEQY | SEQ ID NO: 1134 |
| ASSLGGRTEAF | SEQ ID NO: 1135 |
| ASRGTDTQY | SEQ ID NO: 1136 |
| ASSLDRDYGYT | SEQ ID NO: 1137 |
| ASSRDRNQPQH | SEQ ID NO: 1138 |
| ASSLAYNEQF | SEQ ID NO: 1139 |
| ASSLTGANTEAF | SEQ ID NO: 1140 |
| ASSRDTDTQY | SEQ ID NO: 1141 |
| ASSLQGYTEAF | SEQ ID NO: 1142 |
| ASRVNTEAF | SEQ ID NO: 1143 |
| ASSLAGGDTQY | SEQ ID NO: 1144 |
| ASSQGGNEQF | SEQ ID NO: 1145 |
| ASSPQGNYGYT | SEQ ID NO: 1146 |
| ASSPGPYNEQF | SEQ ID NO: 1147 |
| ASSLSGNYGYT | SEQ ID NO: 1148 |
| ASSFGMNTEAF | SEQ ID NO: 1149 |
| ASRTGGTEAF | SEQ ID NO: 1150 |
| ASSRQGSYEQY | SEQ ID NO: 1151 |
| ASSSGTGGYEQY | SEQ ID NO: 1152 |
| ASSEQETQY | SEQ ID NO: 1153 |
| ASSHQETQY | SEQ ID NO: 1154 |
| ASSRADTQY | SEQ ID NO: 1155 |
| ASSYSSGANVLT | SEQ ID NO: 1156 |
| ASSPDRDYGYT | SEQ ID NO: 1157 |
| ASSSGQNYGYT | SEQ ID NO: 1158 |
| ASSPGLAGYNEQF | SEQ ID NO: 1159 |
| ASSSGTSGYNEQF | SEQ ID NO: 1160 |
| ASSLLQETQY | SEQ ID NO: 1161 |
| ASSQGNYGYT | SEQ ID NO: 1162 |
| ASSPQGTEAF | SEQ ID NO: 1163 |
| ASSGQMNTEAF | SEQ ID NO: 1164 |
| ASSLSQNTEAF | SEQ ID NO: 1165 |
| ASSLGLDTQY | SEQ ID NO: 1166 |
| ASSSYTEAF | SEQ ID NO: 1167 |
| ASSLANQPQH | SEQ ID NO: 1168 |
| ASSPSGNTIY | SEQ ID NO: 1169 |
| ASSLGQGGNQPQH | SEQ ID NO: 1170 |
| ASSRQNTEAF | SEQ ID NO: 1171 |
| ASSLTANYGYT | SEQ ID NO: 1172 |

TABLE I-continued

| Sequence | Sequence ID No |
|---|---|
| ASSLTGNTIY | SEQ ID NO: 1173 |
| ASSLAGGTYEQY | SEQ ID NO: 1174 |
| ASSTGGTEAF | SEQ ID NO: 1175 |
| ASSLQGSTEAF | SEQ ID NO: 1176 |
| ASSPNSNQPQH | SEQ ID NO: 1177 |
| ASSQGADTQY | SEQ ID NO: 1178 |
| ASRTGNTEAF | SEQ ID NO: 1179 |
| ASSLGVTEAF | SEQ ID NO: 1180 |
| ASSQNYEQY | SEQ ID NO: 1181 |
| ASSLVYNEQF | SEQ ID NO: 1182 |
| ASSSTSTDTQY | SEQ ID NO: 1183 |
| ASSPSSTDTQY | SEQ ID NO: 1184 |
| ASSLGEETQY | SEQ ID NO: 1185 |
| ASSLDREETQY | SEQ ID NO: 1186 |
| ASSLGGRNTEAF | SEQ ID NO: 1187 |
| ASSLPTDTQY | SEQ ID NO: 1188 |
| ASSSSGSTDTQY | SEQ ID NO: 1189 |
| ASSVNTEAF | SEQ ID NO: 1190 |
| ASSLEGGNQPQH | SEQ ID NO: 1191 |
| ASSLGTGGNQPQH | SEQ ID NO: 1192 |
| ASSLDGYGYT | SEQ ID NO: 1193 |
| ASSRMNTEAF | SEQ ID NO: 1194 |
| ASSPTGLNTEAF | SEQ ID NO: 1195 |
| ASSPGQGGTEAF | SEQ ID NO: 1196 |
| ASSVQGNTEAF | SEQ ID NO: 1197 |
| ASSLTGYGYT | SEQ ID NO: 1198 |
| ASSLAGRTDTQY | SEQ ID NO: 1199 |
| ASSLGQNYEQY | SEQ ID NO: 1200 |
| ASSSFTDTQY | SEQ ID NO: 1201 |
| ASSLSRETQY | SEQ ID NO: 1202 |
| ASSNYNEQF | SEQ ID NO: 1203 |
| ASSLAGGADTQY | SEQ ID NO: 1204 |
| ASSSGTYEQY | SEQ ID NO: 1205 |
| ASSSGPYEQY | SEQ ID NO: 1206 |
| ASSLGTGYGYT | SEQ ID NO: 1207 |
| ASSLRGADTQY | SEQ ID NO: 1208 |
| ASSPGLAYEQY | SEQ ID NO: 1209 |
| ASSGTSGSTDTQY | SEQ ID NO: 1210 |
| ASSLGLAGNEQF | SEQ ID NO: 1211 |
| ASSQVGETQY | SEQ ID NO: 1212 |
| ASSPRQGNTEAF | SEQ ID NO: 1213 |
| ASSQGYNEQF | SEQ ID NO: 1214 |
| ASSLSPYEQY | SEQ ID NO: 1215 |
| ASSRNNEQF | SEQ ID NO: 1216 |
| ASSLGLAGYEQY | SEQ ID NO: 1217 |
| ASSLGTDYGYT | SEQ ID NO: 1218 |
| ASSLAPNTEAF | SEQ ID NO: 1219 |
| ASSLSGGSYEQY | SEQ ID NO: 1220 |
| ASSLGASYEQY | SEQ ID NO: 1221 |
| ASSRETQY | SEQ ID NO: 1222 |
| ASSPGGSTDTQY | SEQ ID NO: 1223 |
| ASSSDYEQY | SEQ ID NO: 1224 |
| ASSPGGEQY | SEQ ID NO: 1225 |
| ASRGSTDTQY | SEQ ID NO: 1226 |
| ASSPGSQETQY | SEQ ID NO: 1227 |
| ASSLVGGNQPQH | SEQ ID NO: 1228 |
| ASSGNTEAF | SEQ ID NO: 1229 |
| ASRGSNQPQH | SEQ ID NO: 1230 |
| ASSPSGTDTQY | SEQ ID NO: 1231 |
| ASSRGSNQPQH | SEQ ID NO: 1232 |
| ASTLNTEAF | SEQ ID NO: 1233 |
| ASSLTGSSYNEQF | SEQ ID NO: 1234 |
| ASSPLGETQY | SEQ ID NO: 1235 |
| ASSSGGNTEAF | SEQ ID NO: 1236 |
| ASSLRGMNTEAF | SEQ ID NO: 1237 |
| ASSLRQGNTEAF | SEQ ID NO: 1238 |
| ASSLDTNTEAF | SEQ ID NO: 1239 |
| ASSRGSTDTQY | SEQ ID NO: 1240 |
| ASSWDRNTEAF | SEQ ID NO: 1241 |
| ASSRGQNTEAF | SEQ ID NO: 1242 |
| ASSSYEQY | SEQ ID NO: 1243 |
| ASSPTSGSYNEQF | SEQ ID NO: 1244 |
| ASSSGGNQPQH | SEQ ID NO: 1245 |
| ASRRTDTQY | SEQ ID NO: 1246 |
| ASSWTGNTEAF | SEQ ID NO: 1247 |
| ASSPDSYGYT | SEQ ID NO: 1248 |
| ASSGGNQPQH | SEQ ID NO: 1249 |
| ASSLEQNTEAF | SEQ ID NO: 1250 |

TABLE I-continued

| Sequence | Sequence ID No |
|---|---|
| ASSLAGPYEQY | SEQ ID NO: 1251 |
| ASSLGLNNEQF | SEQ ID NO: 1252 |
| ASSLVNQPQH | SEQ ID NO: 1253 |
| ASSVGETQY | SEQ ID NO: 1254 |
| ASSLDRLNTEAF | SEQ ID NO: 1255 |
| ASSQGGETQY | SEQ ID NO: 1256 |
| ASSRDRGETQY | SEQ ID NO: 1257 |
| ASSFGGQETQY | SEQ ID NO: 1258 |
| ASRSSYEQY | SEQ ID NO: 1259 |
| ASSLPQETQY | SEQ ID NO: 1260 |
| ASSPGPNQPQH | SEQ ID NO: 1261 |
| ASSFSGGTDTQY | SEQ ID NO: 1262 |
| ASRGYNEQF | SEQ ID NO: 1263 |
| ASSQDLGQPQH | SEQ ID NO: 1264 |
| ASSPGTYNEQF | SEQ ID NO: 1265 |
| ASSLGQPNTEAF | SEQ ID NO: 1266 |
| ASSLDETQY | SEQ ID NO: 1267 |
| ASSLDGSYEQY | SEQ ID NO: 1268 |
| ASSPRGGTEAF | SEQ ID NO: 1269 |
| ASSLSGSGNTIY | SEQ ID NO: 1270 |
| ASSLGSEAF | SEQ ID NO: 1271 |
| ASSLEGNYGYT | SEQ ID NO: 1272 |
| ASSLAGELF | SEQ ID NO: 1273 |
| ASSRTGSNQPQH | SEQ ID NO: 1274 |
| ASSLQGADTQY | SEQ ID NO: 1275 |
| ASSLVDEQF | SEQ ID NO: 1276 |
| ASSSRGNTEAF | SEQ ID NO: 1277 |
| ASSFGGNEQF | SEQ ID NO: 1278 |
| ASSPRADTQY | SEQ ID NO: 1279 |
| ASSISTDTQY | SEQ ID NO: 1280 |
| ASSLVQNTEAF | SEQ ID NO: 1281 |
| ASSQGPNTEAF | SEQ ID NO: 1282 |
| ASSPGGYGYT | SEQ ID NO: 1283 |
| ASSLGREETQY | SEQ ID NO: 1284 |
| ASSSGSNQPQH | SEQ ID NO: 1285 |
| ASSWTVNTEAF | SEQ ID NO: 1286 |
| ASSLRGGNTEAF | SEQ ID NO: 1287 |
| ASSLRDTEAF | SEQ ID NO: 1288 |
| ASSLRYNEQF | SEQ ID NO: 1289 |
| ASSLGLAEETQY | SEQ ID NO: 1290 |
| ASSGAYEQY | SEQ ID NO: 1291 |
| ASSRLNTEAF | SEQ ID NO: 1292 |
| ASSLGDNEQF | SEQ ID NO: 1293 |
| ASSRDSNYGYT | SEQ ID NO: 1294 |
| ASSLGTSGTDTQY | SEQ ID NO: 1295 |
| ASSPLNEQF | SEQ ID NO: 1296 |
| ASSRDRDQPQH | SEQ ID NO: 1297 |
| ASSPTANTEAF | SEQ ID NO: 1298 |
| ASSQDLNQPQH | SEQ ID NO: 1299 |
| ASSSRGTDTQY | SEQ ID NO: 1300 |
| ASSLVGSSYEQY | SEQ ID NO: 1301 |
| ASSLGYQETQY | SEQ ID NO: 1302 |
| ASSPSGGTDTQY | SEQ ID NO: 1303 |
| ASSLRDEQF | SEQ ID NO: 1304 |
| ASSLQGQETQY | SEQ ID NO: 1305 |
| ASSPGPQETQY | SEQ ID NO: 1306 |
| ASSYGGNQPQH | SEQ ID NO: 1307 |
| ASSEQGNTEAF | SEQ ID NO: 1308 |
| ASSRSNQPQH | SEQ ID NO: 1309 |
| ASSQGSTDTQY | SEQ ID NO: 1310 |
| ASSYSRNTEAF | SEQ ID NO: 1311 |
| ASSLGGGYT | SEQ ID NO: 1312 |
| ASSQDLNTEAF | SEQ ID NO: 1313 |
| ASSRGQQETQY | SEQ ID NO: 1314 |
| ASSSGTVNTEAF | SEQ ID NO: 1315 |
| ASSLEGSTDTQY | SEQ ID NO: 1316 |
| ASSLQGAYEQY | SEQ ID NO: 1317 |
| ASSRDYEQY | SEQ ID NO: 1318 |
| ASRLAGGTDTQY | SEQ ID NO: 1319 |
| ASSLGTGQETQY | SEQ ID NO: 1320 |
| ASSLVMNTEAF | SEQ ID NO: 1321 |
| ASSLGLADTQY | SEQ ID NO: 1322 |
| ASSPLAGGYNEQF | SEQ ID NO: 1323 |
| ASSLRGYGYT | SEQ ID NO: 1324 |
| ASSLGVYNEQF | SEQ ID NO: 1325 |
| ASSWGNTEAF | SEQ ID NO: 1326 |
| ASSRDSYGYT | SEQ ID NO: 1327 |
| ASSLPNTEAF | SEQ ID NO: 1328 |

TABLE I-continued

| Sequence | Sequence ID No |
|---|---|
| ASSSGQLNTEAF | SEQ ID NO: 1329 |
| ASSRGMNTEAF | SEQ ID NO: 1330 |
| ASSWGTDTQY | SEQ ID NO: 1331 |
| ASSLGGGYGYT | SEQ ID NO: 1332 |
| ASSFRTDTQY | SEQ ID NO: 1333 |
| ASSPLGDTQY | SEQ ID NO: 1334 |
| ASSLGGGYNEQF | SEQ ID NO: 1335 |
| ASSLDRGETQY | SEQ ID NO: 1336 |
| ASSLDGSTDTQY | SEQ ID NO: 1337 |
| ASSYGRNTEAF | SEQ ID NO: 1338 |
| ASSLDSSGNTIY | SEQ ID NO: 1339 |
| ASSLTSYNEQF | SEQ ID NO: 1340 |
| ASSRVNTEAF | SEQ ID NO: 1341 |
| ASSLRGGNQPQH | SEQ ID NO: 1342 |
| ASSRTSTDTQY | SEQ ID NO: 1343 |
| ASSRTVQETQY | SEQ ID NO: 1344 |
| ASSLDRGSYNEQF | SEQ ID NO: 1345 |
| ASSLVGEQY | SEQ ID NO: 1346 |
| ASSSSGGTDTQY | SEQ ID NO: 1347 |
| ASSWDSSYEQY | SEQ ID NO: 1348 |
| ASSPGQGADTQY | SEQ ID NO: 1349 |
| ASSSGADTQY | SEQ ID NO: 1350 |
| ASSEGNQPQH | SEQ ID NO: 1351 |
| ASSRTGGTDTQY | SEQ ID NO: 1352 |
| ASSLGTQETQY | SEQ ID NO: 1353 |
| ASSLYTGELF | SEQ ID NO: 1354 |
| ASSLSGEQY | SEQ ID NO: 1355 |
| ASSLAPDTQY | SEQ ID NO: 1356 |
| ASSSTSYEQY | SEQ ID NO: 1357 |
| ASSPTGDYGYT | SEQ ID NO: 1358 |
| ASSLGQGNEQF | SEQ ID NO: 1359 |
| ASSLGQGSNQPQH | SEQ ID NO: 1360 |
| ASSLVGEQF | SEQ ID NO: 1361 |
| ASSPTGMNTEAF | SEQ ID NO: 1362 |
| ASSRQGGNQPQH | SEQ ID NO: 1363 |
| ASSLGNYGYT | SEQ ID NO: 1364 |
| ASSPDSTDTQY | SEQ ID NO: 1365 |
| ASSLRDSNQPQH | SEQ ID NO: 1366 |
| ASSFGGGTDTQY | SEQ ID NO: 1367 |
| ASSYLETQY | SEQ ID NO: 1368 |
| ASSSGTSTDTQY | SEQ ID NO: 1369 |
| ASSRTSGSTDTQY | SEQ ID NO: 1370 |
| ASSPGQSNQPQH | SEQ ID NO: 1371 |
| ASSFGTGSYEQY | SEQ ID NO: 1372 |
| ASSLRGSYNEQF | SEQ ID NO: 1373 |
| ASSDSTDTQY | SEQ ID NO: 1374 |
| ASSPDYNEQF | SEQ ID NO: 1375 |
| ASSLGTGPYEQY | SEQ ID NO: 1376 |
| ASSPGTAQETQY | SEQ ID NO: 1377 |
| ASSLVPYEQY | SEQ ID NO: 1378 |
| ASSPYTGELF | SEQ ID NO: 1379 |
| ASSPSMNTEAF | SEQ ID NO: 1380 |
| ASSLGGAEAF | SEQ ID NO: 1381 |
| ASSYRGNQPQH | SEQ ID NO: 1382 |
| ASSGGSTDTQY | SEQ ID NO: 1383 |
| ASSLGYEQF | SEQ ID NO: 1384 |
| ASSFSYNEQF | SEQ ID NO: 1385 |
| ASSLLVNTEAF | SEQ ID NO: 1386 |
| ASSGTGNTEAF | SEQ ID NO: 1387 |
| ASSESTDTQY | SEQ ID NO: 1388 |
| ASSLSGGSYNEQF | SEQ ID NO: 1389 |
| ASSLRTGNTEAF | SEQ ID NO: 1390 |
| ASSPQGTDTQY | SEQ ID NO: 1391 |
| ASSLSNTGELF | SEQ ID NO: 1392 |
| ASSYSGANVLT | SEQ ID NO: 1393 |
| ASSLAMNTEAF | SEQ ID NO: 1394 |
| ASSLDSLNTEAF | SEQ ID NO: 1395 |
| ASSPGTAYGYT | SEQ ID NO: 1396 |
| ASSPFTDTQY | SEQ ID NO: 1397 |
| ASSPTGTDTQY | SEQ ID NO: 1398 |
| ASSYGDTQY | SEQ ID NO: 1399 |
| ASSYGSNQPQH | SEQ ID NO: 1400 |
| ASSLPSYEQY | SEQ ID NO: 1401 |
| ASSLASDTQY | SEQ ID NO: 1402 |
| ASSPRVNTEAF | SEQ ID NO: 1403 |
| ASSLGAGNTEAF | SEQ ID NO: 1404 |
| ASSQGGGTEAF | SEQ ID NO: 1405 |
| ASSLAQNTEAF | SEQ ID NO: 1406 |

TABLE I-continued

| Sequence | Sequence ID No |
|---|---|
| ASSSRGYEQY | SEQ ID NO: 1407 |
| ASRQNTEAF | SEQ ID NO: 1408 |
| ASSLGGDYGYT | SEQ ID NO: 1409 |
| ASSWDSNQPQH | SEQ ID NO: 1410 |
| ASSENTEAF | SEQ ID NO: 1411 |
| ASSPRQNTEAF | SEQ ID NO: 1412 |
| ASSPGNTIY | SEQ ID NO: 1413 |
| ASSPQNTEAF | SEQ ID NO: 1414 |
| ASSEETQY | SEQ ID NO: 1415 |
| ASSRGQETQY | SEQ ID NO: 1416 |
| ASSLQRNTEAF | SEQ ID NO: 1417 |
| ASSLDSSTDTQY | SEQ ID NO: 1418 |
| ASSPSNEQF | SEQ ID NO: 1419 |
| ASSSVNTEAF | SEQ ID NO: 1420 |
| ASSSPTDTQY | SEQ ID NO: 1421 |
| ASSPSGDTQY | SEQ ID NO: 1422 |
| ASSSNNEQF | SEQ ID NO: 1423 |
| ASSFSNTEAF | SEQ ID NO: 1424 |
| ASSSKETQY | SEQ ID NO: 1425 |
| ASSPRQGSYEQY | SEQ ID NO: 1426 |
| ASSPGQGNSPLH | SEQ ID NO: 1427 |
| ASSPRENTEAF | SEQ ID NO: 1428 |
| ASSLASSYNEQF | SEQ ID NO: 1429 |
| ASSLTSGYNEQF | SEQ ID NO: 1430 |
| ASSFSSYNEQF | SEQ ID NO: 1431 |
| ASSSGRNTEAF | SEQ ID NO: 1432 |
| ASSLTGSTEAF | SEQ ID NO: 1433 |
| ASSRDSSYNEQF | SEQ ID NO: 1434 |
| ASSAGYEQY | SEQ ID NO: 1435 |
| ASSPGTNTEAF | SEQ ID NO: 1436 |
| ASSLGNEQY | SEQ ID NO: 1437 |
| ASSLDGSSYNEQF | SEQ ID NO: 1438 |
| ASSLDRGQETQY | SEQ ID NO: 1439 |
| ASSPLAGGTDTQY | SEQ ID NO: 1440 |
| ASSSQGNEQF | SEQ ID NO: 1441 |
| ASSLLNTGELF | SEQ ID NO: 1442 |
| ASSLTSGQETQY | SEQ ID NO: 1443 |
| ASSLAGGGTDTQY | SEQ ID NO: 1444 |
| ASSFSSTDTQY | SEQ ID NO: 1445 |
| ASSPGTEETQY | SEQ ID NO: 1446 |
| ASSLTNEQF | SEQ ID NO: 1447 |
| ASSSLNQPQH | SEQ ID NO: 1448 |
| ASSPGTSSYNEQF | SEQ ID NO: 1449 |
| ASSLDRDTQY | SEQ ID NO: 1450 |
| ASSPRGDTEAF | SEQ ID NO: 1451 |
| ASSFRGNQPQH | SEQ ID NO: 1452 |
| ASSFSGYEQY | SEQ ID NO: 1453 |
| ASSLNSYNEQF | SEQ ID NO: 1454 |
| ASSRDRGNQPQH | SEQ ID NO: 1455 |
| ASSLAGEQF | SEQ ID NO: 1456 |
| ASSRTGGYEQY | SEQ ID NO: 1457 |
| ASSPTLNTEAF | SEQ ID NO: 1458 |
| ASSADRNTEAF | SEQ ID NO: 1459 |
| ASSLDGSNQPQH | SEQ ID NO: 1460 |
| ASSPTGDTQY | SEQ ID NO: 1461 |
| ASSFGPNTEAF | SEQ ID NO: 1462 |
| ASGSYEQY | SEQ ID NO: 1463 |
| ASSPSGETQY | SEQ ID NO: 1464 |
| ASSLGGPNTEAF | SEQ ID NO: 1465 |
| ASSQDYEQY | SEQ ID NO: 1466 |
| ASSSLETQY | SEQ ID NO: 1467 |
| ASSQDGNQPQH | SEQ ID NO: 1468 |
| ASSLESTDTQY | SEQ ID NO: 1469 |
| ASSLGTLNTEAF | SEQ ID NO: 1470 |
| ASSLANTGELF | SEQ ID NO: 1471 |
| ASSLGKNTEAF | SEQ ID NO: 1472 |
| ASSQDTDTQY | SEQ ID NO: 1473 |
| ASSPDSQETQY | SEQ ID NO: 1474 |
| ASSLRTGELF | SEQ ID NO: 1475 |
| ASSVGTDTQY | SEQ ID NO: 1476 |
| ASSRTGELF | SEQ ID NO: 1477 |
| ASSSGPNTEAF | SEQ ID NO: 1478 |
| ASSLDRANTEAF | SEQ ID NO: 1479 |
| ASSQRETQY | SEQ ID NO: 1480 |
| ASSLGREQY | SEQ ID NO: 1481 |
| ASSPGTGGTEAF | SEQ ID NO: 1482 |
| ASSRDGNQPQH | SEQ ID NO: 1483 |
| ASSPGGSGNTIY | SEQ ID NO: 1484 |

TABLE I-continued

| Sequence | Sequence ID No |
|---|---|
| ASSYSGSTDTQY | SEQ ID NO: 1485 |
| ASSYGTSTDTQY | SEQ ID NO: 1486 |
| ASSYSGGTEAF | SEQ ID NO: 1487 |
| ASSPSLNTEAF | SEQ ID NO: 1488 |
| ASSLGGDEQF | SEQ ID NO: 1489 |
| ASSLGTNYGYT | SEQ ID NO: 1490 |
| ASRGTGNQPQH | SEQ ID NO: 1491 |
| ASSLTGSYNEQF | SEQ ID NO: 1492 |
| ASSLGGGEQY | SEQ ID NO: 1493 |
| ASSLTMNTEAF | SEQ ID NO: 1494 |
| ASSPGTQETQY | SEQ ID NO: 1495 |
| ASSLAGNTGELF | SEQ ID NO: 1496 |
| ASSRTSGYNEQF | SEQ ID NO: 1497 |
| ASSLSGDTEAF | SEQ ID NO: 1498 |
| ASSFSGSSYEQY | SEQ ID NO: 1499 |
| ASSLRSYEQY | SEQ ID NO: 1500 |
| ASSSGGSYNEQF | SEQ ID NO: 1501 |
| ASSPTYNEQF | SEQ ID NO: 1502 |
| ASSFRENTEAF | SEQ ID NO: 1503 |
| ASSRQGMNTEAF | SEQ ID NO: 1504 |
| ASSLSSSYNEQF | SEQ ID NO: 1505 |
| ASSLGSQPQH | SEQ ID NO: 1506 |
| ASSLGAGELF | SEQ ID NO: 1507 |
| ASSTGYEQY | SEQ ID NO: 1508 |
| ASSPDRGTEAF | SEQ ID NO: 1509 |
| ASSLRGDQPQH | SEQ ID NO: 1510 |
| ASSLDRGGTEAF | SEQ ID NO: 1511 |
| ASSLGSNYGYT | SEQ ID NO: 1512 |
| ASSLLGGNTEAF | SEQ ID NO: 1513 |
| ASSLGSNEQF | SEQ ID NO: 1514 |
| ASSLGVSTDTQY | SEQ ID NO: 1515 |
| ASSQDRGNTEAF | SEQ ID NO: 1516 |
| ASSFGTGELF | SEQ ID NO: 1517 |
| ASSPHTDTQY | SEQ ID NO: 1518 |
| ASSFTYEQY | SEQ ID NO: 1519 |
| ASSVDSNQPQH | SEQ ID NO: 1520 |
| ASSPQGLNTEAF | SEQ ID NO: 1521 |
| ASSLSSDTQY | SEQ ID NO: 1522 |
| ASSGSNQPQH | SEQ ID NO: 1523 |
| ASSLSRGTEAF | SEQ ID NO: 1524 |
| ASRRDSNQPQH | SEQ ID NO: 1525 |
| ASSLTNTGELF | SEQ ID NO: 1526 |
| ASSLGHEQY | SEQ ID NO: 1527 |
| ASSPSGSYEQY | SEQ ID NO: 1528 |
| ASSLGGYSNQPQH | SEQ ID NO: 1529 |
| ASSLGGELF | SEQ ID NO: 1530 |
| ASSPDLNTEAF | SEQ ID NO: 1531 |
| ASSDSSGANVLT | SEQ ID NO: 1532 |
| ASSLNYNEQF | SEQ ID NO: 1533 |
| ASRQGNTEAF | SEQ ID NO: 1534 |
| ASSSTGNQPQH | SEQ ID NO: 1535 |
| ASSLVGADTQY | SEQ ID NO: 1536 |
| ASSLGRGNQPQH | SEQ ID NO: 1537 |
| ASSLGTAQETQY | SEQ ID NO: 1538 |
| ASSLEGLNTEAF | SEQ ID NO: 1539 |
| ASSRLAGGTDTQY | SEQ ID NO: 1540 |
| ASSFSVNTEAF | SEQ ID NO: 1541 |
| ASSLGLANEQF | SEQ ID NO: 1542 |
| ASSLDTYEQY | SEQ ID NO: 1543 |
| ASSPSGSYNEQF | SEQ ID NO: 1544 |
| ASSPGTGGNQPQH | SEQ ID NO: 1545 |
| ASSSDSYNEQF | SEQ ID NO: 1546 |
| ASSYSNEQF | SEQ ID NO: 1547 |
| ASSPGTSGTDTQY | SEQ ID NO: 1548 |
| ASSSTENTEAF | SEQ ID NO: 1549 |
| ASSVGDTQY | SEQ ID NO: 1550 |
| ASSPDNEQF | SEQ ID NO: 1551 |
| ASSPSGNTEAF | SEQ ID NO: 1552 |
| ASSRTGDTEAF | SEQ ID NO: 1553 |
| ASSLRGTGELF | SEQ ID NO: 1554 |
| ASSLQGYNEQF | SEQ ID NO: 1555 |
| ASSFGQGNTEAF | SEQ ID NO: 1556 |
| ASSLGTSGYEQY | SEQ ID NO: 1557 |
| ASSLRGSSYNEQF | SEQ ID NO: 1558 |
| ASSLSRTDTQY | SEQ ID NO: 1559 |
| ASSLGSSNQPQH | SEQ ID NO: 1560 |
| ASSNTGELF | SEQ ID NO: 1561 |
| ASSEQGYEQY | SEQ ID NO: 1562 |

TABLE I-continued

| Sequence | Sequence ID No |
|---|---|
| ASSLSRDTQY | SEQ ID NO: 1563 |
| ASSFSGNQPQH | SEQ ID NO: 1564 |
| ASRSYNEQF | SEQ ID NO: 1565 |
| ASSLGLAGSTDTQY | SEQ ID NO: 1566 |
| ASSPGGYNEQF | SEQ ID NO: 1567 |
| ASSLGGSYGYT | SEQ ID NO: 1568 |
| ASSPGQYNEQF | SEQ ID NO: 1569 |
| ASSLRANTEAF | SEQ ID NO: 1570 |
| ASSQDQETQY | SEQ ID NO: 1571 |
| ASSRSSYNEQF | SEQ ID NO: 1572 |
| ASSLPGYEQY | SEQ ID NO: 1573 |
| ASSLRGNYGYT | SEQ ID NO: 1574 |
| ASSFLYEQY | SEQ ID NO: 1575 |
| ASSFLNQPQH | SEQ ID NO: 1576 |
| ASSPGQGQETQY | SEQ ID NO: 1577 |
| ASSPRLNTEAF | SEQ ID NO: 1578 |
| ASSDRGNQPQH | SEQ ID NO: 1579 |
| ASSFGQGNQPQH | SEQ ID NO: 1580 |
| ASSLGAQETQY | SEQ ID NO: 1581 |
| ASSLDGYNEQF | SEQ ID NO: 1582 |
| ASSLAGTYNEQF | SEQ ID NO: 1583 |
| ASSLPGSYEQY | SEQ ID NO: 1584 |
| ASSPQGGNQPQH | SEQ ID NO: 1585 |
| ASSPPGDTQY | SEQ ID NO: 1586 |
| ASSLGQGDQPQH | SEQ ID NO: 1587 |
| ASSLSGGQETQY | SEQ ID NO: 1588 |
| ASSLSRDTEAF | SEQ ID NO: 1589 |
| ASSPDGNTEAF | SEQ ID NO: 1590 |
| ASSLAGPTDTQY | SEQ ID NO: 1591 |
| ASSFGGETQY | SEQ ID NO: 1592 |
| ASSPGQETQY | SEQ ID NO: 1593 |
| ASSFQGTDTQY | SEQ ID NO: 1594 |
| ASSLQANTEAF | SEQ ID NO: 1595 |
| ASSLGQSSYNEQF | SEQ ID NO: 1596 |
| ASSQGLQETQY | SEQ ID NO: 1597 |
| SARQGDTEAF | SEQ ID NO: 1598 |
| ASSPGTGTDTQY | SEQ ID NO: 1599 |
| ASSLINEQF | SEQ ID NO: 1600 |
| ASSLGGAYNEQF | SEQ ID NO: 1601 |
| ASSLYEQY | SEQ ID NO: 1602 |
| ASSSGGETQY | SEQ ID NO: 1603 |
| ASSLAGPYNEQF | SEQ ID NO: 1604 |
| ASSRDNEQF | SEQ ID NO: 1605 |
| ASSLAGANTEAF | SEQ ID NO: 1606 |
| ASSPTGGTDTQY | SEQ ID NO: 1607 |
| ASSLTSSYNEQF | SEQ ID NO: 1608 |
| ASSLGNSNQPQH | SEQ ID NO: 1609 |
| ASSPSGSSYEQY | SEQ ID NO: 1610 |
| ASSSHYEQY | SEQ ID NO: 1611 |
| ASSYSRETQY | SEQ ID NO: 1612 |
| ASSASSYEQY | SEQ ID NO: 1613 |
| ASSPGQGGYEQY | SEQ ID NO: 1614 |
| ASSLDRMNTEAF | SEQ ID NO: 1615 |
| ASSLEGSYEQY | SEQ ID NO: 1616 |
| ASRMNTEAF | SEQ ID NO: 1617 |
| ASSQDSYNEQF | SEQ ID NO: 1618 |
| ASSQGGQPQH | SEQ ID NO: 1619 |
| ASSLDVNTEAF | SEQ ID NO: 1620 |
| ASSLHNEQF | SEQ ID NO: 1621 |
| ASSPTGDTEAF | SEQ ID NO: 1622 |
| ASSRGSYNEQF | SEQ ID NO: 1623 |
| ASSPDQETQY | SEQ ID NO: 1624 |
| ASSPGTGQETQY | SEQ ID NO: 1625 |
| ASSLAGGPNEQF | SEQ ID NO: 1626 |
| ASSPDRGNTEAF | SEQ ID NO: 1627 |
| ASSLVGSSYNEQF | SEQ ID NO: 1628 |
| ASSGTANTEAF | SEQ ID NO: 1629 |
| ASSSGVNTEAF | SEQ ID NO: 1630 |
| ASSPPGQPQH | SEQ ID NO: 1631 |
| ASSSTGNYGYT | SEQ ID NO: 1632 |
| ASSQGGSNQPQH | SEQ ID NO: 1633 |
| ASSLNLNTEAF | SEQ ID NO: 1634 |
| ASSPDRGTDTQY | SEQ ID NO: 1635 |
| ASSSGQGSYEQY | SEQ ID NO: 1636 |
| ASSPGGNYGYT | SEQ ID NO: 1637 |
| ASSLGQPYEQY | SEQ ID NO: 1638 |
| ASSLVSSYEQY | SEQ ID NO: 1639 |
| ASSPQVNTEAF | SEQ ID NO: 1640 |

TABLE I-continued

| Sequence | Sequence ID No |
|---|---|
| ASSPMNTEAF | SEQ ID NO: 1641 |
| ASSLSNYGYT | SEQ ID NO: 1642 |
| ASSSGGYGYT | SEQ ID NO: 1643 |
| ASSPRTGSYEQY | SEQ ID NO: 1644 |
| ASSLGTVQETQY | SEQ ID NO: 1645 |
| ASSPGLAGYEQY | SEQ ID NO: 1646 |
| ASSLAGVTDTQY | SEQ ID NO: 1647 |
| ASSYSDTQY | SEQ ID NO: 1648 |
| ASSYSETQY | SEQ ID NO: 1649 |
| ASSLVANTEAF | SEQ ID NO: 1650 |
| ASSFGADTQY | SEQ ID NO: 1651 |
| ASSLQGVNTEAF | SEQ ID NO: 1652 |
| ASSLLGSNQPQH | SEQ ID NO: 1653 |
| ASSLTGYTEAF | SEQ ID NO: 1654 |
| ASSLEENTEAF | SEQ ID NO: 1655 |
| ASSLAGGQPQH | SEQ ID NO: 1656 |
| ASSRGGSTDTQY | SEQ ID NO: 1657 |
| ASSLTDSNQPQH | SEQ ID NO: 1658 |
| ASSSGTGTYEQY | SEQ ID NO: 1659 |
| ASSLGQGAYNEQF | SEQ ID NO: 1660 |
| ASSLTGNTGELF | SEQ ID NO: 1661 |
| ASSPTSGSYEQY | SEQ ID NO: 1662 |
| ASSLAGRNTEAF | SEQ ID NO: 1663 |
| ASSPRGSYEQY | SEQ ID NO: 1664 |
| ASSLGVNEQF | SEQ ID NO: 1665 |
| ASSETDTQY | SEQ ID NO: 1666 |
| ASSFQGNQPQH | SEQ ID NO: 1667 |
| ASSSGQTYEQY | SEQ ID NO: 1668 |
| ASSFGQGAYEQY | SEQ ID NO: 1669 |
| ASSWGYEQY | SEQ ID NO: 1670 |
| ASSSQGTDTQY | SEQ ID NO: 1671 |
| ASSSPSYEQY | SEQ ID NO: 1672 |
| ASSPDGNQPQH | SEQ ID NO: 1673 |
| ASSLQGGQPQH | SEQ ID NO: 1674 |
| ASSSGLQETQY | SEQ ID NO: 1675 |
| ASSLSGADTQY | SEQ ID NO: 1676 |
| ASSLGQSYGYT | SEQ ID NO: 1677 |
| SARDSNQPQH | SEQ ID NO: 1678 |
| ASSLANYGYT | SEQ ID NO: 1679 |
| ASRTSTDTQY | SEQ ID NO: 1680 |
| ASSFPNTEAF | SEQ ID NO: 1681 |
| ASSPRYEQY | SEQ ID NO: 1682 |
| ASSRYQETQY | SEQ ID NO: 1683 |
| ASSSTYNEQF | SEQ ID NO: 1684 |
| ASSPGNYGYT | SEQ ID NO: 1685 |
| ASSLESYEQY | SEQ ID NO: 1686 |
| ASSLAEETQY | SEQ ID NO: 1687 |
| ASRTSGTDTQY | SEQ ID NO: 1688 |
| ASSQQGYEQY | SEQ ID NO: 1689 |
| ASSYDSNQPQH | SEQ ID NO: 1690 |
| ASSFTSTDTQY | SEQ ID NO: 1691 |
| ASRTGNQPQH | SEQ ID NO: 1692 |
| ASSSPDTQY | SEQ ID NO: 1693 |
| ASSYGSSYEQY | SEQ ID NO: 1694 |
| ASSLNSGNTIY | SEQ ID NO: 1695 |
| ASSFGDTEAF | SEQ ID NO: 1696 |
| ASGSTDTQY | SEQ ID NO: 1697 |
| ASSRTGSTDTQY | SEQ ID NO: 1698 |
| ASSYRVNTEAF | SEQ ID NO: 1699 |
| ASSLGGGGTEAF | SEQ ID NO: 1700 |
| ASSFSLNTEAF | SEQ ID NO: 1701 |
| ASSLDADTQY | SEQ ID NO: 1702 |
| ASSLGRSSYEQY | SEQ ID NO: 1703 |
| ASSLGYTDTQY | SEQ ID NO: 1704 |
| ASSLGPTYEQY | SEQ ID NO: 1705 |
| ASSLGTTYEQY | SEQ ID NO: 1706 |
| ASSRTGQETQY | SEQ ID NO: 1707 |
| ASSLAGTGELF | SEQ ID NO: 1708 |
| ASSQGQGNQPQH | SEQ ID NO: 1709 |
| ASSLVGDTEAF | SEQ ID NO: 1710 |
| ASSRGQGNTEAF | SEQ ID NO: 1711 |
| ASSRTGSSYEQY | SEQ ID NO: 1712 |
| ASSLRDSYEQY | SEQ ID NO: 1713 |
| ASSFNSNQPQH | SEQ ID NO: 1714 |
| ASSSGMNTEAF | SEQ ID NO: 1715 |
| ASSFDTEAF | SEQ ID NO: 1716 |
| ASSLDRTYEQY | SEQ ID NO: 1717 |
| SARTGNTEAF | SEQ ID NO: 1718 |

TABLE I-continued

| Sequence | Sequence ID No |
|---|---|
| ASSLFYEQY | SEQ ID NO: 1719 |
| ASSQNTDTQY | SEQ ID NO: 1720 |
| ASSRDRGNTEAF | SEQ ID NO: 1721 |
| ASSFGNTIY | SEQ ID NO: 1722 |
| ASSPDRVNTEAF | SEQ ID NO: 1723 |
| ASSQDRDTEAF | SEQ ID NO: 1724 |
| ASSPQGETQY | SEQ ID NO: 1725 |
| ASSGQGGNQPQH | SEQ ID NO: 1726 |
| ASSFGGSGNTIY | SEQ ID NO: 1727 |
| ASSFQGYEQY | SEQ ID NO: 1728 |
| ASSLRQETQY | SEQ ID NO: 1729 |
| ASSLLAGSTDTQY | SEQ ID NO: 1730 |
| ASSFGSSYNEQF | SEQ ID NO: 1731 |
| ASRGGTEAF | SEQ ID NO: 1732 |
| ASSFTGGTEAF | SEQ ID NO: 1733 |
| ASSLAGGGTEAF | SEQ ID NO: 1734 |
| ASSLFNEQF | SEQ ID NO: 1735 |
| ASSSTGELF | SEQ ID NO: 1736 |
| ASSFRNEQF | SEQ ID NO: 1737 |
| ASSFGDQPQH | SEQ ID NO: 1738 |
| ASSRGSSYNEQF | SEQ ID NO: 1739 |
| ASSLEYNEQF | SEQ ID NO: 1740 |
| ASSVGQNTEAF | SEQ ID NO: 1741 |
| ASSRDRDYEQY | SEQ ID NO: 1742 |
| ASSLTSGGYNEQF | SEQ ID NO: 1743 |
| ASSLTGGGTEAF | SEQ ID NO: 1744 |
| ASSLDNYGYT | SEQ ID NO: 1745 |
| ASSPGRSTDTQY | SEQ ID NO: 1746 |
| ASSPGQGSYNEQF | SEQ ID NO: 1747 |
| ASSPRGQETQY | SEQ ID NO: 1748 |
| ASSPTQETQY | SEQ ID NO: 1749 |
| ASSPGPSTDTQY | SEQ ID NO: 1750 |
| ASSSGTGNQPQH | SEQ ID NO: 1751 |
| ASSPSSGNTIY | SEQ ID NO: 1752 |
| ASSLGPNYGYT | SEQ ID NO: 1753 |
| ASSPGTLNTEAF | SEQ ID NO: 1754 |
| ASSLGLAGADTQY | SEQ ID NO: 1755 |
| ASSYGTDTQY | SEQ ID NO: 1756 |
| ASSLGLNEQF | SEQ ID NO: 1757 |
| ASSSTGGTDTQY | SEQ ID NO: 1758 |
| ASSLVGYNEQF | SEQ ID NO: 1759 |
| ASSFYSNQPQH | SEQ ID NO: 1760 |
| ASSLGLAGETQY | SEQ ID NO: 1761 |
| ASSQAETQY | SEQ ID NO: 1762 |
| ASSYSSNQPQH | SEQ ID NO: 1763 |
| ASSYDRNTEAF | SEQ ID NO: 1764 |
| ASSLLGEQY | SEQ ID NO: 1765 |
| ASSSGGSYEQY | SEQ ID NO: 1766 |
| ASSKNTEAF | SEQ ID NO: 1767 |
| ASRQGYEQY | SEQ ID NO: 1768 |
| ASSLGGNNEQF | SEQ ID NO: 1769 |
| ASSPPSYNEQF | SEQ ID NO: 1770 |
| ASSFSGSYEQY | SEQ ID NO: 1771 |
| ASSLVGGNEQF | SEQ ID NO: 1772 |
| ASSFLTDTQY | SEQ ID NO: 1773 |
| ASSWGTEAF | SEQ ID NO: 1774 |
| ASSFGGNYGYT | SEQ ID NO: 1775 |
| ASSGQGGTEAF | SEQ ID NO: 1776 |
| ASSPQGMNTEAF | SEQ ID NO: 1777 |
| ASSFGGLNTEAF | SEQ ID NO: 1778 |
| ASSSLSYEQY | SEQ ID NO: 1779 |
| ASSLLMNTEAF | SEQ ID NO: 1780 |
| ASSLVPNTEAF | SEQ ID NO: 1781 |
| ASSFAGNTEAF | SEQ ID NO: 1782 |
| ASSFGQGTDTQY | SEQ ID NO: 1783 |
| ASSLTGPYEQY | SEQ ID NO: 1784 |
| ASSFYTDTQY | SEQ ID NO: 1785 |
| ASSLRSSYNEQF | SEQ ID NO: 1786 |
| ASSLVGGSYEQY | SEQ ID NO: 1787 |
| ASSLGGPYNEQF | SEQ ID NO: 1788 |
| ASSFNTDTQY | SEQ ID NO: 1789 |
| ASSLGQGDGYT | SEQ ID NO: 1790 |
| ASSSGTYNEQF | SEQ ID NO: 1791 |
| ASSPTGGYGYT | SEQ ID NO: 1792 |
| ASSLATEAF | SEQ ID NO: 1793 |
| ASSPLGNEQF | SEQ ID NO: 1794 |
| ASSTQGNTEAF | SEQ ID NO: 1795 |
| ASSPDTEAF | SEQ ID NO: 1796 |

TABLE I-continued

| Sequence | Sequence ID No |
|---|---|
| ASSLDSGNTIY | SEQ ID NO: 1797 |
| ASSELAGGPDTQY | SEQ ID NO: 1798 |
| ASSPLQETQY | SEQ ID NO: 1799 |
| ASSLSGTGELF | SEQ ID NO: 1800 |
| ASSYSGNQPQH | SEQ ID NO: 1801 |
| ASSFGSYNEQF | SEQ ID NO: 1802 |
| ASSGTSTDTQY | SEQ ID NO: 1803 |
| ASSPPGQETQY | SEQ ID NO: 1804 |
| ASSPGLAGETQY | SEQ ID NO: 1805 |
| ASSLGGSNTEAF | SEQ ID NO: 1806 |
| ASRLTDTQY | SEQ ID NO: 1807 |
| ASRGGNQPQH | SEQ ID NO: 1808 |
| ASSQGGDTQY | SEQ ID NO: 1809 |
| ASSEGETQY | SEQ ID NO: 1810 |
| ASSFGGDTQY | SEQ ID NO: 1811 |
| ASSSIYEQY | SEQ ID NO: 1812 |
| ASSPRDSYEQY | SEQ ID NO: 1813 |
| ASSYSLNTEAF | SEQ ID NO: 1814 |
| ASSFPGNTEAF | SEQ ID NO: 1815 |
| ASSQVGYEQY | SEQ ID NO: 1816 |
| ASSLTQNTEAF | SEQ ID NO: 1817 |
| ASSLQDTQY | SEQ ID NO: 1818 |
| ASSPGQGNEKLF | SEQ ID NO: 1819 |
| ASSLGGANVLT | SEQ ID NO: 1820 |
| ASSRQMNTEAF | SEQ ID NO: 1821 |
| ASSLRDQPQH | SEQ ID NO: 1822 |
| ASSLQGSYNEQF | SEQ ID NO: 1823 |
| ASSPGGSSYNEQF | SEQ ID NO: 1824 |
| ASSLWGTEAF | SEQ ID NO: 1825 |
| ASSTGLNTEAF | SEQ ID NO: 1826 |
| ASSPDRGYEQY | SEQ ID NO: 1827 |
| ASSRQLNTEAF | SEQ ID NO: 1828 |
| ASSFGGSSYNEQF | SEQ ID NO: 1829 |
| ASSLGNNEQF | SEQ ID NO: 1830 |
| ASSPGRETQY | SEQ ID NO: 1831 |
| ASSSGGQPQH | SEQ ID NO: 1832 |
| ASSLNEKLF | SEQ ID NO: 1833 |
| ASSSGLSTDTQY | SEQ ID NO: 1834 |
| ASSLPYNEQF | SEQ ID NO: 1835 |
| ASSPQMNTEAF | SEQ ID NO: 1836 |
| ASSPGRMNTEAF | SEQ ID NO: 1837 |
| ASSRDRNYGYT | SEQ ID NO: 1838 |
| ASSFRVNTEAF | SEQ ID NO: 1839 |
| ASSLGRNNEQF | SEQ ID NO: 1840 |
| ASSLGQSSYEQY | SEQ ID NO: 1841 |
| ASSSMNTEAF | SEQ ID NO: 1842 |
| ASSSSSTDTQY | SEQ ID NO: 1843 |
| ASSRQGDTEAF | SEQ ID NO: 1844 |
| ASSLASGTDTQY | SEQ ID NO: 1845 |
| ASSLGQDYGYT | SEQ ID NO: 1846 |
| ASSPTGQETQY | SEQ ID NO: 1847 |
| ASSLQGDTQY | SEQ ID NO: 1848 |
| ASSPGANTEAF | SEQ ID NO: 1849 |
| ASSLGQGGYT | SEQ ID NO: 1850 |
| ASSLRGSSYEQY | SEQ ID NO: 1851 |
| ASSFGQPQH | SEQ ID NO: 1852 |
| ASSQDGYEQY | SEQ ID NO: 1853 |
| ASSAQGNTEAF | SEQ ID NO: 1854 |
| ASSLVGTGELF | SEQ ID NO: 1855 |
| ASSLNNQPQH | SEQ ID NO: 1856 |
| ASSSVYEQY | SEQ ID NO: 1857 |
| ASSRTGTDTQY | SEQ ID NO: 1858 |
| ASSYNTEAF | SEQ ID NO: 1859 |
| ASSLGGGEQF | SEQ ID NO: 1860 |
| ASSDYEQY | SEQ ID NO: 1861 |
| ASSPRGNQPQH | SEQ ID NO: 1862 |
| ASSPRMNTEAF | SEQ ID NO: 1863 |
| ASSPLGTEAF | SEQ ID NO: 1864 |
| ASSPRTGQETQY | SEQ ID NO: 1865 |
| ASSPTGNEQF | SEQ ID NO: 1866 |
| ASSPRNEQF | SEQ ID NO: 1867 |
| ASSYSGDTQY | SEQ ID NO: 1868 |
| ASSPQGDTQY | SEQ ID NO: 1869 |
| ASSPATDTQY | SEQ ID NO: 1870 |
| ASSLGTSSYNEQF | SEQ ID NO: 1871 |
| ASSLGRSSYNEQF | SEQ ID NO: 1872 |
| ASSFQGGTEAF | SEQ ID NO: 1873 |
| ASSPGGSSYEQY | SEQ ID NO: 1874 |

TABLE I-continued

| Sequence | Sequence ID No |
|---|---|
| ASSLAGGYGYT | SEQ ID NO: 1875 |
| ASSLSRNQPQH | SEQ ID NO: 1876 |
| SARGGNTEAF | SEQ ID NO: 1877 |
| ASSFTENTEAF | SEQ ID NO: 1878 |
| ASSFGANTEAF | SEQ ID NO: 1879 |
| ASSYGTEAF | SEQ ID NO: 1880 |
| ASSSGTGNTEAF | SEQ ID NO: 1881 |
| ASSLGATNEKLF | SEQ ID NO: 1882 |
| ASSLTGRTEAF | SEQ ID NO: 1883 |
| ASSLNMNTEAF | SEQ ID NO: 1884 |
| ASSDSSYEQY | SEQ ID NO: 1885 |
| ASSRQGLNTEAF | SEQ ID NO: 1886 |
| ASSFMNTEAF | SEQ ID NO: 1887 |
| ASSQGGYGYT | SEQ ID NO: 1888 |
| ASSLTGGSYNEQF | SEQ ID NO: 1889 |
| ASSLGGTYNEQF | SEQ ID NO: 1890 |
| ASSSLAGGYNEQF | SEQ ID NO: 1891 |
| ASSLQGSSYEQY | SEQ ID NO: 1892 |
| ASSLVSYNEQF | SEQ ID NO: 1893 |
| ASSYSGEQY | SEQ ID NO: 1894 |
| ASSLLLNTEAF | SEQ ID NO: 1895 |
| ASSLGGATDTQY | SEQ ID NO: 1896 |
| ASSLLAGSYNEQF | SEQ ID NO: 1897 |
| ASSQGANTEAF | SEQ ID NO: 1898 |
| ASSVGLNTEAF | SEQ ID NO: 1899 |
| ASSYLYEQY | SEQ ID NO: 1900 |
| ASSLGVSNQPQH | SEQ ID NO: 1901 |
| ASSWGQNTEAF | SEQ ID NO: 1902 |
| ASRTGGTDTQY | SEQ ID NO: 1903 |
| ASSVADTQY | SEQ ID NO: 1904 |
| ASSLDRGNEQF | SEQ ID NO: 1905 |
| ASSRGTGELF | SEQ ID NO: 1906 |
| ASRDSSYEQY | SEQ ID NO: 1907 |
| ASSVTGNTEAF | SEQ ID NO: 1908 |
| ASSSTANTEAF | SEQ ID NO: 1909 |
| ASSSLAGGTDTQY | SEQ ID NO: 1910 |
| ASSRGLQETQY | SEQ ID NO: 1911 |
| ASSLLGSTDTQY | SEQ ID NO: 1912 |
| ASSPDGYEQY | SEQ ID NO: 1913 |
| ASSLARDTQY | SEQ ID NO: 1914 |
| ASSLGGGADTQY | SEQ ID NO: 1915 |
| ASSQGSYNEQF | SEQ ID NO: 1916 |
| ASSLTGGETQY | SEQ ID NO: 1917 |
| ASSPGTTYEQY | SEQ ID NO: 1918 |
| ASSPGTANYGYT | SEQ ID NO: 1919 |
| ASSFSSGNTIY | SEQ ID NO: 1920 |
| ASSDRGNTEAF | SEQ ID NO: 1921 |
| ASSLAGGEQY | SEQ ID NO: 1922 |
| ASSPDRDTEAF | SEQ ID NO: 1923 |
| ASSPLNQPQH | SEQ ID NO: 1924 |
| ASSESSYEQY | SEQ ID NO: 1925 |
| ASSPGGGYEQY | SEQ ID NO: 1926 |
| ASRGQLNTEAF | SEQ ID NO: 1927 |
| ASSRTGNYGYT | SEQ ID NO: 1928 |
| ASSSNSYEQY | SEQ ID NO: 1929 |
| ASSLGTEETQY | SEQ ID NO: 1930 |
| ASSLVDTEAF | SEQ ID NO: 1931 |
| SARDSYEQY | SEQ ID NO: 1932 |
| ASSYSGTEAF | SEQ ID NO: 1933 |
| ASSLGTENTEAF | SEQ ID NO: 1934 |
| ASSYSSYNEQF | SEQ ID NO: 1935 |
| ASSWTENTEAF | SEQ ID NO: 1936 |
| ASSLGAGTDTQY | SEQ ID NO: 1937 |
| ASSPTSGSTDTQY | SEQ ID NO: 1938 |
| ASSPNYGYT | SEQ ID NO: 1939 |
| ASSRDRSTDTQY | SEQ ID NO: 1940 |
| ASSPQGDTEAF | SEQ ID NO: 1941 |
| ASSTNTEAF | SEQ ID NO: 1942 |
| ASSPGQNQPQH | SEQ ID NO: 1943 |
| ASSQVGNTEAF | SEQ ID NO: 1944 |
| ASSPLETQY | SEQ ID NO: 1945 |
| ASSDRDTGELF | SEQ ID NO: 1946 |
| ASSPTGGYEQY | SEQ ID NO: 1947 |
| ASSPTGYGYT | SEQ ID NO: 1948 |
| ASSVGGGTEAF | SEQ ID NO: 1949 |
| ASSFRGETQY | SEQ ID NO: 1950 |
| ASSLGLAAYNEQF | SEQ ID NO: 1951 |
| ASSLDGETQY | SEQ ID NO: 1952 |

TABLE I-continued

| Sequence | Sequence ID No |
|---|---|
| ASSDGYEQY | SEQ ID NO: 1953 |
| ASSPGLAYNEQF | SEQ ID NO: 1954 |
| ASSLIGETQY | SEQ ID NO: 1955 |
| ASSRGDTEAF | SEQ ID NO: 1956 |
| ASSSQMNTEAF | SEQ ID NO: 1957 |
| ASSQDRGTDTQY | SEQ ID NO: 1958 |
| ASSLTSGGTDTQY | SEQ ID NO: 1959 |
| ASSFGGSYNEQF | SEQ ID NO: 1960 |
| ASSLGPGELF | SEQ ID NO: 1961 |
| ASSQDGETQY | SEQ ID NO: 1962 |
| ASSLEGGQPQH | SEQ ID NO: 1963 |
| ASSPVNTEAF | SEQ ID NO: 1964 |
| ASSFGGQPQH | SEQ ID NO: 1965 |
| ASSYGLNTEAF | SEQ ID NO: 1966 |
| ASSPGTASYEQY | SEQ ID NO: 1967 |
| ASSLGRGNEQF | SEQ ID NO: 1968 |
| ASSLVGYGYT | SEQ ID NO: 1969 |
| ASSPTYEQY | SEQ ID NO: 1970 |
| ASSFRGYEQY | SEQ ID NO: 1971 |
| ASSLDGNTIY | SEQ ID NO: 1972 |
| ASSTGNQPQH | SEQ ID NO: 1973 |
| ASSAGETQY | SEQ ID NO: 1974 |
| ASSQGSSYEQY | SEQ ID NO: 1975 |
| ASSLRDSSYEQY | SEQ ID NO: 1976 |
| ASSLRQGTDTQY | SEQ ID NO: 1977 |
| ASSPGSGNTIY | SEQ ID NO: 1978 |
| ASSLQGGTDTQY | SEQ ID NO: 1979 |
| ASSLTGGQPQH | SEQ ID NO: 1980 |
| ASSLGVGTEAF | SEQ ID NO: 1981 |
| ASSPGTSGSYEQY | SEQ ID NO: 1982 |
| ASSRGYNEQF | SEQ ID NO: 1983 |
| ASSPPNTEAF | SEQ ID NO: 1984 |
| ASSLLAGAYNEQF | SEQ ID NO: 1985 |
| ASSPDRLNTEAF | SEQ ID NO: 1986 |
| ASSRAYEQY | SEQ ID NO: 1987 |
| ASSGGSNQPQH | SEQ ID NO: 1988 |
| ASSPGTGNYGYT | SEQ ID NO: 1989 |
| ASSQDRGNQPQH | SEQ ID NO: 1990 |
| ASSRTSGSYNEQF | SEQ ID NO: 1991 |
| ASSPGLAGGTDTQY | SEQ ID NO: 1992 |
| ASSLVTEAF | SEQ ID NO: 1993 |
| ASSLLENTEAF | SEQ ID NO: 1994 |
| ASSLTGGQETQY | SEQ ID NO: 1995 |
| ASSGYEQY | SEQ ID NO: 1996 |
| ASSLGQGSTEAF | SEQ ID NO: 1997 |
| ASSLAPYEQY | SEQ ID NO: 1998 |
| ASSFRGSYEQY | SEQ ID NO: 1999 |
| ASSLIYEQY | SEQ ID NO: 2000 |
| ASSFRGNEQF | SEQ ID NO: 2001 |
| ASSRDGNTEAF | SEQ ID NO: 2002 |
| ASSSGLAGGTDTQY | SEQ ID NO: 2003 |
| ASSFPGTDTQY | SEQ ID NO: 2004 |
| ASSFRGGTEAF | SEQ ID NO: 2005 |
| ASSLGQGDTEAF | SEQ ID NO: 2006 |
| ASSLLYNEQF | SEQ ID NO: 2007 |
| ASSEAYEQY | SEQ ID NO: 2008 |
| ASSLRGEQF | SEQ ID NO: 2009 |
| ASSFTVNTEAF | SEQ ID NO: 2010 |
| ASSLTGADTQY | SEQ ID NO: 2011 |
| ASSLVGSYNEQF | SEQ ID NO: 2012 |
| ASSPLSTDTQY | SEQ ID NO: 2013 |
| ASSGTYEQY | SEQ ID NO: 2014 |
| ASSSGGSTDTQY | SEQ ID NO: 2015 |
| ASSLSGMNTEAF | SEQ ID NO: 2016 |
| ASSPGTGYNEQF | SEQ ID NO: 2017 |
| ASSSGGEQY | SEQ ID NO: 2018 |
| ASSQGAYEQY | SEQ ID NO: 2019 |
| ASSLVGGYEQY | SEQ ID NO: 2020 |
| ASSGQGYGYT | SEQ ID NO: 2021 |
| ASSPGTAYNEQF | SEQ ID NO: 2022 |
| ASSDSSTDTQY | SEQ ID NO: 2023 |
| ASSQVNEQF | SEQ ID NO: 2024 |
| ASSLAGGAYEQY | SEQ ID NO: 2025 |
| ASSLGRDYEQY | SEQ ID NO: 2026 |
| ASSLGFTDTQY | SEQ ID NO: 2027 |
| ASSLGWNTEAF | SEQ ID NO: 2028 |
| ASSLGLNTGELF | SEQ ID NO: 2029 |
| ASSFRYEQY | SEQ ID NO: 2030 |

TABLE I-continued

| Sequence | Sequence ID No |
|---|---|
| ASSPGQANTEAF | SEQ ID NO: 2031 |
| ASSGGNTEAF | SEQ ID NO: 2032 |
| ASSLAGRETQY | SEQ ID NO: 2033 |
| ASSFGQETQY | SEQ ID NO: 2034 |
| ASSLAGGPTDTQY | SEQ ID NO: 2035 |
| ASSYTGELF | SEQ ID NO: 2036 |
| SARQGNQPQH | SEQ ID NO: 2037 |
| ASSFSGNEQF | SEQ ID NO: 2038 |
| ASSLEGYNEQF | SEQ ID NO: 2039 |
| ASSPGDYGYT | SEQ ID NO: 2040 |
| SARTGNQPQH | SEQ ID NO: 2041 |
| ASSRDRDTEAF | SEQ ID NO: 2042 |
| ASSVGYEQY | SEQ ID NO: 2043 |
| ASSGGGTDTQY | SEQ ID NO: 2044 |
| ASSLEGDQPQH | SEQ ID NO: 2045 |
| SARLAGGQETQY | SEQ ID NO: 2046 |
| ASSGGSSYNEQF | SEQ ID NO: 2047 |
| ASSSSGTDTQY | SEQ ID NO: 2048 |
| ASSQTVNTEAF | SEQ ID NO: 2049 |
| ASSEGNTEAF | SEQ ID NO: 2050 |
| ASSSLDTQY | SEQ ID NO: 2051 |
| ASSQGQGAYEQY | SEQ ID NO: 2052 |
| ASSLGQRNTEAF | SEQ ID NO: 2053 |
| ASSFSENTEAF | SEQ ID NO: 2054 |
| ASSSGGDTQY | SEQ ID NO: 2055 |
| ASSLDSMNTEAF | SEQ ID NO: 2056 |
| SARQGNTEAF | SEQ ID NO: 2057 |
| ASSLGLAQETQY | SEQ ID NO: 2058 |
| ASSQNNEQF | SEQ ID NO: 2059 |
| ASSLGRSNQPQH | SEQ ID NO: 2060 |
| ASSLGPNEQF | SEQ ID NO: 2061 |
| ASSSPGTDTQY | SEQ ID NO: 2062 |
| ASSFSRNTEAF | SEQ ID NO: 2063 |
| ASSPGGQPQH | SEQ ID NO: 2064 |
| ASSSQGSNQPQH | SEQ ID NO: 2065 |
| ASSPLGYEQY | SEQ ID NO: 2066 |
| ASSLDYGYT | SEQ ID NO: 2067 |
| ASSLSGTYEQY | SEQ ID NO: 2068 |
| ASSSGTAYEQY | SEQ ID NO: 2069 |
| ASSRQVNTEAF | SEQ ID NO: 2070 |
| ASSLDRGPYEQY | SEQ ID NO: 2071 |
| ASSLQGQPQH | SEQ ID NO: 2072 |
| ASSLSGGETQY | SEQ ID NO: 2073 |
| ASSRGGQETQY | SEQ ID NO: 2074 |
| ASSRDRGSYEQY | SEQ ID NO: 2075 |
| ASRSSGNTIY | SEQ ID NO: 2076 |
| ASSSGLAGYNEQF | SEQ ID NO: 2077 |
| ASSLQGRNTEAF | SEQ ID NO: 2078 |
| ASSLEGYTEAF | SEQ ID NO: 2079 |
| ASSPGLAGNEQF | SEQ ID NO: 2080 |
| ASSLQGPNTEAF | SEQ ID NO: 2081 |
| ASSRDRGTEAF | SEQ ID NO: 2082 |
| ASSEGTDTQY | SEQ ID NO: 2083 |
| ASSFGQNYGYT | SEQ ID NO: 2084 |
| ASSGTSGYNEQF | SEQ ID NO: 2085 |
| ASSATGNTEAF | SEQ ID NO: 2086 |
| ASSLVGGQETQY | SEQ ID NO: 2087 |
| ASSPTGSTDTQY | SEQ ID NO: 2088 |
| ASSLGDSSYEQY | SEQ ID NO: 2089 |
| ASSLGTNQPQH | SEQ ID NO: 2090 |
| ASSLQGAGTEAF | SEQ ID NO: 2091 |
| ASSRQGAYEQY | SEQ ID NO: 2092 |
| ASSFNNEQF | SEQ ID NO: 2093 |
| ASSFGYNEQF | SEQ ID NO: 2094 |
| ASSWTANTEAF | SEQ ID NO: 2095 |
| ASSPGQGGQPQH | SEQ ID NO: 2096 |
| ASSFGGMNTEAF | SEQ ID NO: 2097 |
| ASSLKNTEAF | SEQ ID NO: 2098 |
| ASSRRETQY | SEQ ID NO: 2099 |
| ASSLEPNTEAF | SEQ ID NO: 2100 |
| ASSFDNEQF | SEQ ID NO: 2101 |
| ASSFLNEQF | SEQ ID NO: 2102 |
| ASSRDSNTEAF | SEQ ID NO: 2103 |
| ASSSSGYEQY | SEQ ID NO: 2104 |
| ASSPPGADTQY | SEQ ID NO: 2105 |
| ASSLSGDQPQH | SEQ ID NO: 2106 |
| ASSLENQPQH | SEQ ID NO: 2107 |
| ASSLRNTGELF | SEQ ID NO: 2108 |

TABLE I-continued

| Sequence | Sequence ID No |
|---|---|
| ASSPGQGTEAF | SEQ ID NO: 2109 |
| ASSSGAYEQY | SEQ ID NO: 2110 |
| ASSQGSGNTIY | SEQ ID NO: 2111 |
| ASSPQGYGYT | SEQ ID NO: 2112 |
| ASSLGPNNEQF | SEQ ID NO: 2113 |
| ASSSQENTEAF | SEQ ID NO: 2114 |
| ASSYSSTDTQY | SEQ ID NO: 2115 |
| ASSLQGETQY | SEQ ID NO: 2116 |
| ASSLQGATEAF | SEQ ID NO: 2117 |
| ASSLLSNQPQH | SEQ ID NO: 2118 |
| ASTGNTEAF | SEQ ID NO: 2119 |
| ASRGSSYNEQF | SEQ ID NO: 2120 |
| ASSPGSDTQY | SEQ ID NO: 2121 |
| ASGQETQY | SEQ ID NO: 2122 |
| ASSLDRSSYEQY | SEQ ID NO: 2123 |
| ASSQGDQPQH | SEQ ID NO: 2124 |
| ASSLGGGDTQY | SEQ ID NO: 2125 |
| ASRRGNTEAF | SEQ ID NO: 2126 |
| ASSPDSSNQPQH | SEQ ID NO: 2127 |
| ASSLTADTQY | SEQ ID NO: 2128 |
| ASSLQNTGELF | SEQ ID NO: 2129 |
| ASSSSQETQY | SEQ ID NO: 2130 |
| ASSPGLAGDTQY | SEQ ID NO: 2131 |
| ASSDRYEQY | SEQ ID NO: 2132 |
| ASRGQGTDTQY | SEQ ID NO: 2133 |
| ASSSNSNQPQH | SEQ ID NO: 2134 |
| ASSPGGTQY | SEQ ID NO: 2135 |
| ASSRDRSSYEQY | SEQ ID NO: 2136 |
| ASSLEGGTDTQY | SEQ ID NO: 2137 |
| ASSFRGQETQY | SEQ ID NO: 2138 |
| ASSRDRTYEQY | SEQ ID NO: 2139 |
| ASSPQGANTEAF | SEQ ID NO: 2140 |
| ASRDSYEQY | SEQ ID NO: 2141 |
| ASSLGTGNYGYT | SEQ ID NO: 2142 |
| ASSPRGPDTQY | SEQ ID NO: 2143 |
| ASSDTYEQY | SEQ ID NO: 2144 |
| ASSYGNEQF | SEQ ID NO: 2145 |
| ASSLGTANYGYT | SEQ ID NO: 2146 |
| ASSDRGYEQY | SEQ ID NO: 2147 |
| ASSQTGGTEAF | SEQ ID NO: 2148 |
| ASSPGLAGGNEQF | SEQ ID NO: 2149 |
| ASSQGGEQF | SEQ ID NO: 2150 |
| ASSLSGLNTEAF | SEQ ID NO: 2151 |
| ASSRGGYEQY | SEQ ID NO: 2152 |
| ASSPRTSTDTQY | SEQ ID NO: 2153 |
| ASSVGNTEAF | SEQ ID NO: 2154 |
| ASSSGLAGTDTQY | SEQ ID NO: 2155 |
| ASSLGGGSTDTQY | SEQ ID NO: 2156 |
| ASSPTGSSYEQY | SEQ ID NO: 2157 |
| ASSRGADTQY | SEQ ID NO: 2158 |
| ASSLGPNTGELF | SEQ ID NO: 2159 |
| ASSLARGTEAF | SEQ ID NO: 2160 |
| ASSPDRAYEQY | SEQ ID NO: 2161 |
| ASSQVADTQY | SEQ ID NO: 2162 |
| ASRGETQY | SEQ ID NO: 2163 |
| ASSEGSNQPQH | SEQ ID NO: 2164 |
| ASRGGTDTQY | SEQ ID NO: 2165 |
| ASSFSGQETQY | SEQ ID NO: 2166 |
| ASSFDSYEQY | SEQ ID NO: 2167 |
| ASSIGGTEAF | SEQ ID NO: 2168 |
| ASSPGLAEETQY | SEQ ID NO: 2169 |
| ASSAAYEQY | SEQ ID NO: 2170 |
| ASSFSGELF | SEQ ID NO: 2171 |
| ASSLSPSYEQY | SEQ ID NO: 2172 |
| ASSLGQGNEKLF | SEQ ID NO: 2173 |
| ASSLGGASTDTQY | SEQ ID NO: 2174 |
| ASSSTGSYEQY | SEQ ID NO: 2175 |
| ASSPLDTQY | SEQ ID NO: 2176 |
| ASSSGQMNTEAF | SEQ ID NO: 2177 |
| ASSPPGNEQF | SEQ ID NO: 2178 |
| ASSQGPDTQY | SEQ ID NO: 2179 |
| ASSGGSYEQY | SEQ ID NO: 2180 |
| ASSLGLAYNEQF | SEQ ID NO: 2181 |
| ASSNSNQPQH | SEQ ID NO: 2182 |
| ASRNTGELF | SEQ ID NO: 2183 |
| ASSRSYNEQF | SEQ ID NO: 2184 |
| ASSQVTDTQY | SEQ ID NO: 2185 |
| ASSLGGNEQY | SEQ ID NO: 2186 |

TABLE I-continued

| Sequence | Sequence ID No |
|---|---|
| ASSSSETQY | SEQ ID NO: 2187 |
| ASSQVNTEAF | SEQ ID NO: 2188 |
| ASSPPGQGYEQY | SEQ ID NO: 2189 |
| ASSYSENTEAF | SEQ ID NO: 2190 |
| SARGGYEQY | SEQ ID NO: 2191 |
| ASSLRDEQY | SEQ ID NO: 2192 |
| ASSPGQVNTEAF | SEQ ID NO: 2193 |
| ASSLTGEETQY | SEQ ID NO: 2194 |
| ASSSRNTEAF | SEQ ID NO: 2195 |
| ASSFRSTDTQY | SEQ ID NO: 2196 |
| ASSFTGELF | SEQ ID NO: 2197 |
| ASSYSRGTEAF | SEQ ID NO: 2198 |
| ASSFAYEQY | SEQ ID NO: 2199 |
| ASSRQGNYGYT | SEQ ID NO: 2200 |
| ASSYSYNEQF | SEQ ID NO: 2201 |
| ASSLQGNTGELF | SEQ ID NO: 2202 |
| ASSPRTANTEAF | SEQ ID NO: 2203 |
| ASSPGTTDTQY | SEQ ID NO: 2204 |
| ASGYNEQF | SEQ ID NO: 2205 |
| ASSLGNTDTQY | SEQ ID NO: 2206 |
| ASSSGTSGTDTQY | SEQ ID NO: 2207 |
| ASSQDRAYEQY | SEQ ID NO: 2208 |
| ASSTGTDTQY | SEQ ID NO: 2209 |
| ASSQEGYEQY | SEQ ID NO: 2210 |
| ASSLGVDTQY | SEQ ID NO: 2211 |
| ASSPTSGGYNEQF | SEQ ID NO: 2212 |
| ASSLDGDTQY | SEQ ID NO: 2213 |
| ASSATYEQY | SEQ ID NO: 2214 |
| ASSPPYNEQF | SEQ ID NO: 2215 |
| ASSLTNQPQH | SEQ ID NO: 2216 |
| ASSLTAYEQY | SEQ ID NO: 2217 |
| ASSQGGNQPQH | SEQ ID NO: 2218 |
| ASSLVGGETQY | SEQ ID NO: 2219 |
| ASSRQGQETQY | SEQ ID NO: 2220 |
| ASSLSGAYEQY | SEQ ID NO: 2221 |
| ASSSGLYNEQF | SEQ ID NO: 2222 |
| ASSLMGNTEAF | SEQ ID NO: 2223 |
| ASRNTDTQY | SEQ ID NO: 2224 |
| ASSLGGSDTQY | SEQ ID NO: 2225 |
| ASSPPQETQY | SEQ ID NO: 2226 |
| ASSLTGTNTEAF | SEQ ID NO: 2227 |
| ASSLASGSYEQY | SEQ ID NO: 2228 |
| ASSLEGDTEAF | SEQ ID NO: 2229 |
| ASSQDRGYGYT | SEQ ID NO: 2230 |
| ASSLASGNTIY | SEQ ID NO: 2231 |
| ASSPGGMNTEAF | SEQ ID NO: 2232 |
| ASSTTGNTEAF | SEQ ID NO: 2233 |
| ASSFRNQPQH | SEQ ID NO: 2234 |
| ASSPGSSGNTIY | SEQ ID NO: 2235 |
| ASSLSGGYNEQF | SEQ ID NO: 2236 |
| ASSLRQGYEQY | SEQ ID NO: 2237 |
| ASRGSGNTIY | SEQ ID NO: 2238 |
| ASSRTTDTQY | SEQ ID NO: 2239 |
| ASSSGQGPYEQY | SEQ ID NO: 2240 |
| ASSGSYNEQF | SEQ ID NO: 2241 |
| ASSQGQNYGYT | SEQ ID NO: 2242 |
| ASSLLGGTDTQY | SEQ ID NO: 2243 |
| ASSLVTGELF | SEQ ID NO: 2244 |
| ASSLGQGGYGYT | SEQ ID NO: 2245 |
| ASSPGTSSYEQY | SEQ ID NO: 2246 |
| ASSTNTGELF | SEQ ID NO: 2247 |
| ASSSRGTEAF | SEQ ID NO: 2248 |
| ASSPGPDTQY | SEQ ID NO: 2249 |
| ASRGTEAF | SEQ ID NO: 2250 |
| ASSQGQGNTEAF | SEQ ID NO: 2251 |
| ASSLRPNTEAF | SEQ ID NO: 2252 |
| ASSLDRNEQF | SEQ ID NO: 2253 |
| ASSPDRYEQY | SEQ ID NO: 2254 |
| ASSSQVNTEAF | SEQ ID NO: 2255 |
| ASSLMETQY | SEQ ID NO: 2256 |
| ASSSGNYGYT | SEQ ID NO: 2257 |
| ASSSDSTDTQY | SEQ ID NO: 2258 |
| ASSSQGDTEAF | SEQ ID NO: 2259 |
| ASSLDRSSYNEQF | SEQ ID NO: 2260 |
| ASSFAETQY | SEQ ID NO: 2261 |
| ASSSGGSNQPQH | SEQ ID NO: 2262 |
| ASSLAVQETQY | SEQ ID NO: 2263 |
| ASSRTGGNTEAF | SEQ ID NO: 2264 |

TABLE I-continued

| Sequence | Sequence ID No |
|---|---|
| ASSLQGTGELF | SEQ ID NO: 2265 |
| ASSSTGSNQPQH | SEQ ID NO: 2266 |
| ASSYSGGYEQY | SEQ ID NO: 2267 |
| ASSRDYNEQF | SEQ ID NO: 2268 |
| ASSLDQNTEAF | SEQ ID NO: 2269 |
| ASSPPGYEQY | SEQ ID NO: 2270 |
| ASSRTGDQPQH | SEQ ID NO: 2271 |
| ASSLLRNTEAF | SEQ ID NO: 2272 |
| ASSYGGYEQY | SEQ ID NO: 2273 |
| ASSEGYGYT | SEQ ID NO: 2274 |
| ASSQGDYGYT | SEQ ID NO: 2275 |
| ASSPTGSGNTIY | SEQ ID NO: 2276 |
| ASSRDQETQY | SEQ ID NO: 2277 |
| ASSLGGPTDTQY | SEQ ID NO: 2278 |
| ASSPLGTDTQY | SEQ ID NO: 2279 |
| ASSLGGVTEAF | SEQ ID NO: 2280 |
| ASSADSNQPQH | SEQ ID NO: 2281 |
| ASSLEGGNTEAF | SEQ ID NO: 2282 |
| ASSPGTDYEQY | SEQ ID NO: 2283 |
| ASSLGRNTGELF | SEQ ID NO: 2284 |
| ASSYGGSYEQY | SEQ ID NO: 2285 |
| ASSLGNYEQY | SEQ ID NO: 2286 |
| ASSLTGANVLT | SEQ ID NO: 2287 |
| ASSSTGYGYT | SEQ ID NO: 2288 |
| ASSPGTGSYNEQF | SEQ ID NO: 2289 |
| ASGTYEQY | SEQ ID NO: 2290 |
| ASSLVNTGELF | SEQ ID NO: 2291 |
| ASSFGQQETQY | SEQ ID NO: 2292 |
| ASSLAGSQETQY | SEQ ID NO: 2293 |
| ASSPTGGNTEAF | SEQ ID NO: 2294 |
| ASSLVGLNTEAF | SEQ ID NO: 2295 |
| ASRGQETQY | SEQ ID NO: 2296 |
| ASSFPSTDTQY | SEQ ID NO: 2297 |
| ASSSDRGYEQY | SEQ ID NO: 2298 |
| ASSPTGTYEQY | SEQ ID NO: 2299 |
| ASSAGNTEAF | SEQ ID NO: 2300 |
| ASSRDGYEQY | SEQ ID NO: 2301 |
| ASSLGRADTQY | SEQ ID NO: 2302 |
| ASSLEGADTQY | SEQ ID NO: 2303 |
| ASSPTSGTDTQY | SEQ ID NO: 2304 |
| ASSFGTANTEAF | SEQ ID NO: 2305 |
| ASSLKGYEQY | SEQ ID NO: 2306 |
| ASSLYRNTEAF | SEQ ID NO: 2307 |
| ASSLAGPDTQY | SEQ ID NO: 2308 |
| ASSPRRNTEAF | SEQ ID NO: 2309 |
| ASSLTGGNEQF | SEQ ID NO: 2310 |
| ASRKNTEAF | SEQ ID NO: 2311 |
| ASSQDSTDTQY | SEQ ID NO: 2312 |
| ASSLVGNTIY | SEQ ID NO: 2313 |
| ASSPGLNQPQH | SEQ ID NO: 2314 |
| ASSSGTSYEQY | SEQ ID NO: 2315 |
| ASSLQGRTEAF | SEQ ID NO: 2316 |
| ASSLDRADTQY | SEQ ID NO: 2317 |
| ASSPQGSYEQY | SEQ ID NO: 2318 |
| ASSPTGSSYNEQF | SEQ ID NO: 2319 |
| ASRDYNEQF | SEQ ID NO: 2320 |
| ASSSGPYNEQF | SEQ ID NO: 2321 |
| ASSIQGNTEAF | SEQ ID NO: 2322 |
| ASSRGGSYNEQF | SEQ ID NO: 2323 |
| ASSYSGGNTEAF | SEQ ID NO: 2324 |
| ASSRNYEQY | SEQ ID NO: 2325 |
| ASSVDRNTEAF | SEQ ID NO: 2326 |
| ASSHSTDTQY | SEQ ID NO: 2327 |
| ASSFGTGGYEQY | SEQ ID NO: 2328 |
| ASSPGTAGNTIY | SEQ ID NO: 2329 |
| ASSLGHQETQY | SEQ ID NO: 2330 |
| ASSLGGAGNTIY | SEQ ID NO: 2331 |
| ASSLARNEQF | SEQ ID NO: 2332 |
| ASSLEGYSNQPQH | SEQ ID NO: 2333 |
| ASSSLNEQF | SEQ ID NO: 2334 |
| ASSFPDTQY | SEQ ID NO: 2335 |
| ASSQGENTEAF | SEQ ID NO: 2336 |
| ASSPQGSGNTIY | SEQ ID NO: 2337 |
| ASSPGDTEAF | SEQ ID NO: 2338 |
| ASSQDRGNEQF | SEQ ID NO: 2339 |
| ASSPTGDQPQH | SEQ ID NO: 2340 |
| ASSYSRGYEQY | SEQ ID NO: 2341 |
| ASSLLGDTEAF | SEQ ID NO: 2342 |

TABLE I-continued

| Sequence | Sequence ID No |
|---|---|
| ASRRTGNTEAF | SEQ ID NO: 2343 |
| ASSLLAGYNEQF | SEQ ID NO: 2344 |
| ASSLAGASTDTQY | SEQ ID NO: 2345 |
| ASSLTGPNTEAF | SEQ ID NO: 2346 |
| ASSFSGTEAF | SEQ ID NO: 2347 |
| ASSLQGAGNTIY | SEQ ID NO: 2348 |
| ASSLGGSQPQH | SEQ ID NO: 2349 |
| ASSDRGTDTQY | SEQ ID NO: 2350 |
| ASSLAGAQETQY | SEQ ID NO: 2351 |
| ASSLSYGYT | SEQ ID NO: 2352 |
| ASSLEGNTIY | SEQ ID NO: 2353 |
| ASSLAGGTGELF | SEQ ID NO: 2354 |
| ASSPGQGGNQPQH | SEQ ID NO: 2355 |
| ASSLGLAGVNEQF | SEQ ID NO: 2356 |
| ASSLLGSYEQY | SEQ ID NO: 2357 |
| ASSSGGNEQF | SEQ ID NO: 2358 |
| ASSPSSNQPQH | SEQ ID NO: 2359 |
| ASSGTSGTDTQY | SEQ ID NO: 2360 |
| ASRSSTDTQY | SEQ ID NO: 2361 |
| ASSPGRNQPQH | SEQ ID NO: 2362 |
| ASSYSGSYEQY | SEQ ID NO: 2363 |
| ASSFNYEQY | SEQ ID NO: 2364 |
| ASSVGSNQPQH | SEQ ID NO: 2365 |
| ASSTDRNTEAF | SEQ ID NO: 2366 |
| SARGSNQPQH | SEQ ID NO: 2367 |
| ASSLGQSNTEAF | SEQ ID NO: 2368 |
| ASSPGEETQY | SEQ ID NO: 2369 |
| ASSLAPTDTQY | SEQ ID NO: 2370 |
| ASSQDRYEQY | SEQ ID NO: 2371 |
| ASSRYSNQPQH | SEQ ID NO: 2372 |
| ASSLAGGTYNEQF | SEQ ID NO: 2373 |
| ASSYSVNTEAF | SEQ ID NO: 2374 |
| ASRGQMNTEAF | SEQ ID NO: 2375 |
| ASSYRGTDTQY | SEQ ID NO: 2376 |
| ASSLGGGSNQPQH | SEQ ID NO: 2377 |
| ASSPRSYEQY | SEQ ID NO: 2378 |
| ASSLGTASYEQY | SEQ ID NO: 2379 |
| ASSPRQGNQPQH | SEQ ID NO: 2380 |
| ASSSQGYGYT | SEQ ID NO: 2381 |
| ASSLDLTDTQY | SEQ ID NO: 2382 |
| ASSLDRGEQY | SEQ ID NO: 2383 |
| ASSYSNTEAF | SEQ ID NO: 2384 |
| ASSPRGGNQPQH | SEQ ID NO: 2385 |
| ASSLGVSGNTIY | SEQ ID NO: 2386 |
| ASSSGQAYEQY | SEQ ID NO: 2387 |
| ASSYGGTDTQY | SEQ ID NO: 2388 |
| ASSPTGGSYEQY | SEQ ID NO: 2389 |
| ASSLVAGGTDTQY | SEQ ID NO: 2390 |
| ASSRGQGYEQY | SEQ ID NO: 2391 |
| ASSRDRVNTEAF | SEQ ID NO: 2392 |
| ASSYSGSSYNEQF | SEQ ID NO: 2393 |
| ASRGSYEQY | SEQ ID NO: 2394 |
| ASSQTGYEQY | SEQ ID NO: 2395 |
| ASSYGSYEQY | SEQ ID NO: 2396 |
| ASSPLADTQY | SEQ ID NO: 2397 |
| ASSLGLAGGQETQY | SEQ ID NO: 2398 |
| ASSSGSGNTIY | SEQ ID NO: 2399 |
| ASSRDLNTEAF | SEQ ID NO: 2400 |
| ASSQDSSYEQY | SEQ ID NO: 2401 |
| ASSPRTVNTEAF | SEQ ID NO: 2402 |
| ASSPTGVNTEAF | SEQ ID NO: 2403 |
| ASRGSGANVLT | SEQ ID NO: 2404 |
| ASSLNGNQPQH | SEQ ID NO: 2405 |
| ASSLGQKETQY | SEQ ID NO: 2406 |
| ASSLAASYEQY | SEQ ID NO: 2407 |
| ASSLWGNEQF | SEQ ID NO: 2408 |
| ASSLVGSGNTIY | SEQ ID NO: 2409 |
| ASSLRGYNEQF | SEQ ID NO: 2410 |
| ASSQSSYNEQF | SEQ ID NO: 2411 |
| ASSSTGLNTEAF | SEQ ID NO: 2412 |
| ASSLAGGGETQY | SEQ ID NO: 2413 |
| ASSFQENTEAF | SEQ ID NO: 2414 |
| ASSELAGGTDTQY | SEQ ID NO: 2415 |
| ASSPGTVQETQY | SEQ ID NO: 2416 |
| ASSLEGSSYNEQF | SEQ ID NO: 2417 |
| ASSLPGQPQH | SEQ ID NO: 2418 |
| ASSERETQY | SEQ ID NO: 2419 |
| ASSLGTSGSYEQY | SEQ ID NO: 2420 |

TABLE I-continued

| Sequence | Sequence ID No |
|---|---|
| ASSQGQETQY | SEQ ID NO: 2421 |
| ASSYSGGNQPQH | SEQ ID NO: 2422 |
| ASRRQGNTEAF | SEQ ID NO: 2423 |
| ASSLQGPYEQY | SEQ ID NO: 2424 |
| ASSPRDTEAF | SEQ ID NO: 2425 |
| ASSSITDTQY | SEQ ID NO: 2426 |
| ASSLRQGGTEAF | SEQ ID NO: 2427 |
| ASSLDRGNSPLH | SEQ ID NO: 2428 |
| ASSQGQGYGYT | SEQ ID NO: 2429 |
| ASSPRGSTDTQY | SEQ ID NO: 2430 |
| ASSTGSYEQY | SEQ ID NO: 2431 |
| ASSEGLNTEAF | SEQ ID NO: 2432 |
| ASSPRSSYEQY | SEQ ID NO: 2433 |
| ASSRGSGNTIY | SEQ ID NO: 2434 |
| ASSSDSYGYT | SEQ ID NO: 2435 |
| ASSLAGGRETQY | SEQ ID NO: 2436 |
| ASSQVGNEQF | SEQ ID NO: 2437 |
| ASSPGRSYEQY | SEQ ID NO: 2438 |
| ASSLAGSTEAF | SEQ ID NO: 2439 |
| ASSLQGDYGYT | SEQ ID NO: 2440 |
| ASSLGRGETQY | SEQ ID NO: 2441 |
| ASSLLAGGPDTQY | SEQ ID NO: 2442 |
| ASSYSGSSYEQY | SEQ ID NO: 2443 |
| ASSLGGNSPLH | SEQ ID NO: 2444 |
| ASSPGRQETQY | SEQ ID NO: 2445 |
| ASSPGLGTDTQY | SEQ ID NO: 2446 |
| ASSFGSQETQY | SEQ ID NO: 2447 |
| ASSLDTQY | SEQ ID NO: 2448 |
| ASSPPGGTEAF | SEQ ID NO: 2449 |
| ASSQSDTQY | SEQ ID NO: 2450 |
| ASSPAETQY | SEQ ID NO: 2451 |
| ASSEEETQY | SEQ ID NO: 2452 |
| ASSSPYNEQF | SEQ ID NO: 2453 |
| ASSLQGTYEQY | SEQ ID NO: 2454 |
| ASSSTGTDTQY | SEQ ID NO: 2455 |
| ASSAGTDTQY | SEQ ID NO: 2456 |
| ASSSYTGELF | SEQ ID NO: 2457 |
| ASSLSGEQF | SEQ ID NO: 2458 |
| ASSLGPMNTEAF | SEQ ID NO: 2459 |
| SASGSTDTQY | SEQ ID NO: 2460 |
| ASSLAATDTQY | SEQ ID NO: 2461 |
| ASSPTGYNEQF | SEQ ID NO: 2462 |
| ASSFSTEAF | SEQ ID NO: 2463 |
| ASSRQGTEAF | SEQ ID NO: 2464 |
| ASSLGGPEAF | SEQ ID NO: 2465 |
| ASRDRGTDTQY | SEQ ID NO: 2466 |
| ASSLADSYEQY | SEQ ID NO: 2467 |
| ASSLGTDYEQY | SEQ ID NO: 2468 |
| ASSPITDTQY | SEQ ID NO: 2469 |
| ASSLGQGSTDTQY | SEQ ID NO: 2470 |
| ASSSSGSSYEQY | SEQ ID NO: 2471 |
| ASSLGTAYGYT | SEQ ID NO: 2472 |
| ASSLLSSYNEQF | SEQ ID NO: 2473 |
| ASSPHNEQF | SEQ ID NO: 2474 |
| ASSLARGTDTQY | SEQ ID NO: 2475 |
| ASSLGDSTDTQY | SEQ ID NO: 2476 |
| ASSLEGSSYEQY | SEQ ID NO: 2477 |
| ASSVGGTDTQY | SEQ ID NO: 2478 |
| ASSPGTENTEAF | SEQ ID NO: 2479 |
| ASSLVRTDTQY | SEQ ID NO: 2480 |
| ASSYSGNEQF | SEQ ID NO: 2481 |
| ASSFGGGNQPQH | SEQ ID NO: 2482 |
| ASSQGRNQPQH | SEQ ID NO: 2483 |
| ASSPGLYEQY | SEQ ID NO: 2484 |
| ASSRTGGSYEQY | SEQ ID NO: 2485 |
| ASSLGATEAF | SEQ ID NO: 2486 |
| ASSLSSNTEAF | SEQ ID NO: 2487 |
| ASSPGYQETQY | SEQ ID NO: 2488 |
| ASSPGVQETQY | SEQ ID NO: 2489 |
| ASSLGAGTEAF | SEQ ID NO: 2490 |
| ASSGGSYNEQF | SEQ ID NO: 2491 |
| ASSLSNSPLH | SEQ ID NO: 2492 |
| ASSLGGTNTEAF | SEQ ID NO: 2493 |
| ASSLSTYEQY | SEQ ID NO: 2494 |
| ASSRRNTEAF | SEQ ID NO: 2495 |
| ASSTGETQY | SEQ ID NO: 2496 |
| ASSLAGTSYEQY | SEQ ID NO: 2497 |
| ASSPGQTNTEAF | SEQ ID NO: 2498 |

TABLE I-continued

| Sequence | Sequence ID No |
|---|---|
| ASSGGGNQPQH | SEQ ID NO: 2499 |
| ASSYTGNTEAF | SEQ ID NO: 2500 |
| ASSPSSGANVLT | SEQ ID NO: 2501 |
| ASSLTGAGNTIY | SEQ ID NO: 2502 |
| ASSYGQGYEQY | SEQ ID NO: 2503 |
| ASSGGETQY | SEQ ID NO: 2504 |
| ASSQVLNTEAF | SEQ ID NO: 2505 |
| ASSLSGPYEQY | SEQ ID NO: 2506 |
| ASSQGTYEQY | SEQ ID NO: 2507 |
| ASSRNTDTQY | SEQ ID NO: 2508 |
| ASSLTGSYGYT | SEQ ID NO: 2509 |
| ASSQGLNQPQH | SEQ ID NO: 2510 |
| ASSQGGSYEQY | SEQ ID NO: 2511 |
| ASSYGGTEAF | SEQ ID NO: 2512 |
| ASSPDRGSYEQY | SEQ ID NO: 2513 |
| ASSSGTGYEQY | SEQ ID NO: 2514 |
| ASSLDRSNQPQH | SEQ ID NO: 2515 |
| ASSLVAYEQY | SEQ ID NO: 2516 |
| SARRETQY | SEQ ID NO: 2517 |
| ASSSRGNEQF | SEQ ID NO: 2518 |
| ASSLEGMNTEAF | SEQ ID NO: 2519 |
| ASSQQGNQPQH | SEQ ID NO: 2520 |
| ASSLGQLYEQY | SEQ ID NO: 2521 |
| ASSPGGLNTEAF | SEQ ID NO: 2522 |
| ASSPGPTDTQY | SEQ ID NO: 2523 |
| ASSLIDTQY | SEQ ID NO: 2524 |
| ASSHYNEQF | SEQ ID NO: 2525 |
| ASSSGTGPYEQY | SEQ ID NO: 2526 |
| ASSRDTGELF | SEQ ID NO: 2527 |
| ASSLALETQY | SEQ ID NO: 2528 |
| ASSPGGADTQY | SEQ ID NO: 2529 |
| ASSLGTGTEAF | SEQ ID NO: 2530 |
| ASRDRGNTEAF | SEQ ID NO: 2531 |
| ASSLGHLNTEAF | SEQ ID NO: 2532 |
| ASSGTGGTDTQY | SEQ ID NO: 2533 |
| ASSWGETQY | SEQ ID NO: 2534 |
| ASSLAGYTEAF | SEQ ID NO: 2535 |
| ASSLTGRNTEAF | SEQ ID NO: 2536 |
| ASSLGTGSNQPQH | SEQ ID NO: 2537 |
| ASSPSADTQY | SEQ ID NO: 2538 |
| ASRASTDTQY | SEQ ID NO: 2539 |
| ASSLNSPLH | SEQ ID NO: 2540 |
| ASSLGGDEQY | SEQ ID NO: 2541 |
| ASSLGLADYNEQF | SEQ ID NO: 2542 |
| ASSDRNTEAF | SEQ ID NO: 2543 |
| ASSRGVNTEAF | SEQ ID NO: 2544 |
| ASSQLNTEAF | SEQ ID NO: 2545 |
| ASSLASQETQY | SEQ ID NO: 2546 |
| ASSFGGNTIY | SEQ ID NO: 2547 |
| ASSLTGDEQY | SEQ ID NO: 2548 |
| ASRDRGYEQY | SEQ ID NO: 2549 |
| ASSLPGGTEAF | SEQ ID NO: 2550 |
| ASSPQGGNTEAF | SEQ ID NO: 2551 |
| ASSLGTGGTDTQY | SEQ ID NO: 2552 |
| ASSGQPNTEAF | SEQ ID NO: 2553 |
| ASSSGQETQY | SEQ ID NO: 2554 |
| ASSLDQPQH | SEQ ID NO: 2555 |
| ASSGGYGYT | SEQ ID NO: 2556 |
| ASSPSGNEQF | SEQ ID NO: 2557 |
| ASSRGPNTEAF | SEQ ID NO: 2558 |
| ASSLRQSTDTQY | SEQ ID NO: 2559 |
| ASSLGQGYTEAF | SEQ ID NO: 2560 |
| ASSRDRGQETQY | SEQ ID NO: 2561 |
| ASSYGVNTEAF | SEQ ID NO: 2562 |
| ASSANTEAF | SEQ ID NO: 2563 |
| ASRRDSTDTQY | SEQ ID NO: 2564 |
| ASSISYEQY | SEQ ID NO: 2565 |
| ASSLGQDTEAF | SEQ ID NO: 2566 |
| ASSRGSSYEQY | SEQ ID NO: 2567 |
| ASSLGLETQY | SEQ ID NO: 2568 |
| ASSLRGPYEQY | SEQ ID NO: 2569 |
| ASSSQGTEAF | SEQ ID NO: 2570 |
| ASSLDGQPQH | SEQ ID NO: 2571 |
| ASSSGGQETQY | SEQ ID NO: 2572 |
| ASSPGTVYGYT | SEQ ID NO: 2573 |
| ASSTTYEQY | SEQ ID NO: 2574 |
| ASSLGRGSYEQY | SEQ ID NO: 2575 |
| ASSSGGGTDTQY | SEQ ID NO: 2576 |

TABLE I-continued

| Sequence | Sequence ID No |
|---|---|
| ASSRTNTEAF | SEQ ID NO: 2577 |
| SARGNTEAF | SEQ ID NO: 2578 |
| ASSQAGYEQY | SEQ ID NO: 2579 |
| ASSLGLAGNNEQF | SEQ ID NO: 2580 |
| ASSWGGTEAF | SEQ ID NO: 2581 |
| ASSLGANQPQH | SEQ ID NO: 2582 |
| ASSPGATNEKLF | SEQ ID NO: 2583 |
| ASSLSAYEQY | SEQ ID NO: 2584 |
| ASSPHYEQY | SEQ ID NO: 2585 |
| ASSPSGNQPQH | SEQ ID NO: 2586 |
| ASSLKGGTEAF | SEQ ID NO: 2587 |
| ASSPSGGSYNEQF | SEQ ID NO: 2588 |
| ASSPTRNTEAF | SEQ ID NO: 2589 |
| ASSPRGGNTEAF | SEQ ID NO: 2590 |
| ASSPGYTEAF | SEQ ID NO: 2591 |
| ASSRTDSNQPQH | SEQ ID NO: 2592 |
| ASSPQENTEAF | SEQ ID NO: 2593 |
| ASSFLGTEAF | SEQ ID NO: 2594 |
| ASSPRDSNQPQH | SEQ ID NO: 2595 |
| ASSQYQETQY | SEQ ID NO: 2596 |
| ASSLDWNTEAF | SEQ ID NO: 2597 |
| ASSLGGTSTDTQY | SEQ ID NO: 2598 |
| ASSLGLAETQY | SEQ ID NO: 2599 |
| ASSLNGNTEAF | SEQ ID NO: 2600 |
| ASSLDNSPLH | SEQ ID NO: 2601 |
| ASSPRGSSYNEQF | SEQ ID NO: 2602 |
| ASSLVRDTQY | SEQ ID NO: 2603 |
| ASSLVQGNTEAF | SEQ ID NO: 2604 |
| ASSPSNTEAF | SEQ ID NO: 2605 |
| SARTSGSYEQY | SEQ ID NO: 2606 |
| ASSLWNTEAF | SEQ ID NO: 2607 |
| ASSLAGVYNEQF | SEQ ID NO: 2608 |
| ASSYGGNEQF | SEQ ID NO: 2609 |
| ASSSTGGSYEQY | SEQ ID NO: 2610 |
| ASSLTGGEQY | SEQ ID NO: 2611 |
| ASSLGSGTDTQY | SEQ ID NO: 2612 |
| ASSLAGAETQY | SEQ ID NO: 2613 |
| ASSPRGSYNEQF | SEQ ID NO: 2614 |
| SARTGDTEAF | SEQ ID NO: 2615 |
| ASSLESSYNEQF | SEQ ID NO: 2616 |
| ASSRGRNTEAF | SEQ ID NO: 2617 |
| ASSPGLAGADTQY | SEQ ID NO: 2618 |
| ASRTGSYEQY | SEQ ID NO: 2619 |
| ASSYSGGTDTQY | SEQ ID NO: 2620 |
| ASSSVTDTQY | SEQ ID NO: 2621 |
| ASSPLGNTEAF | SEQ ID NO: 2622 |
| ASSFQNTEAF | SEQ ID NO: 2623 |
| ASSPRGYNEQF | SEQ ID NO: 2624 |
| ASSLTASTDTQY | SEQ ID NO: 2625 |
| ASSPPGGYEQY | SEQ ID NO: 2626 |
| ASRANTEAF | SEQ ID NO: 2627 |
| ASSLEGRNTEAF | SEQ ID NO: 2628 |
| ASSFLGNTEAF | SEQ ID NO: 2629 |
| ASSLDPNQPQH | SEQ ID NO: 2630 |
| ASSLGSPLH | SEQ ID NO: 2631 |
| ASSLEGSGNTIY | SEQ ID NO: 2632 |
| ASSYRGETQY | SEQ ID NO: 2633 |
| ASSFSGSYNEQF | SEQ ID NO: 2634 |
| ASSLYSTDTQY | SEQ ID NO: 2635 |
| ASSLGNETQY | SEQ ID NO: 2636 |
| ASSPGYSNQPQH | SEQ ID NO: 2637 |
| ASSLSSYNSPLH | SEQ ID NO: 2638 |
| ASSLNRDTEAF | SEQ ID NO: 2639 |
| ASSLQGPDTQY | SEQ ID NO: 2640 |
| ASSPNYNEQF | SEQ ID NO: 2641 |
| ASSLDTYNEQF | SEQ ID NO: 2642 |
| ASSRDSSGNTIY | SEQ ID NO: 2643 |
| ASSQGQQETQY | SEQ ID NO: 2644 |
| ASSLGGGPYEQY | SEQ ID NO: 2645 |
| ASSFRRNTEAF | SEQ ID NO: 2646 |
| ASSYRYEQY | SEQ ID NO: 2647 |
| ASSQGDTEAF | SEQ ID NO: 2648 |
| ASSLGRVNTEAF | SEQ ID NO: 2649 |
| ASSLVGDQPQH | SEQ ID NO: 2650 |
| ASSRDRGYGYT | SEQ ID NO: 2651 |
| ASSLGGATEAF | SEQ ID NO: 2652 |
| ASSLGGAQETQY | SEQ ID NO: 2653 |
| ASSLTTYEQY | SEQ ID NO: 2654 |

TABLE I-continued

| Sequence | Sequence ID No |
|---|---|
| ASSQGTGELF | SEQ ID NO: 2655 |
| ASSLLDEQF | SEQ ID NO: 2656 |
| ASSLQGGYGYT | SEQ ID NO: 2657 |
| ASSLGQGGETQY | SEQ ID NO: 2658 |
| ASTRNTEAF | SEQ ID NO: 2659 |
| ASSSGGYNEQF | SEQ ID NO: 2660 |
| ASSLGLAAYEQY | SEQ ID NO: 2661 |
| ASSLGAANTEAF | SEQ ID NO: 2662 |
| ASSLGSSGANVLT | SEQ ID NO: 2663 |
| ASSPGQDYGYT | SEQ ID NO: 2664 |
| ASSQDLETQY | SEQ ID NO: 2665 |
| ASSSRGNQPQH | SEQ ID NO: 2666 |
| ASSYSTGELF | SEQ ID NO: 2667 |
| ASSFSGSNQPQH | SEQ ID NO: 2668 |
| ASSLLTGELF | SEQ ID NO: 2669 |
| ASSLVSNTEAF | SEQ ID NO: 2670 |
| ASSRSDTQY | SEQ ID NO: 2671 |
| ASSLGSEQF | SEQ ID NO: 2672 |
| SARDRDTEAF | SEQ ID NO: 2673 |
| ASSRDRDYGYT | SEQ ID NO: 2674 |
| ASSLAGSDTQY | SEQ ID NO: 2675 |
| ASSGADTQY | SEQ ID NO: 2676 |
| ASSLAGGSNQPQH | SEQ ID NO: 2677 |
| ASSQTTDTQY | SEQ ID NO: 2678 |
| ASSLGQGRTEAF | SEQ ID NO: 2679 |
| ASSPASTDTQY | SEQ ID NO: 2680 |
| ASSPGLAADTQY | SEQ ID NO: 2681 |
| ASSQVETQY | SEQ ID NO: 2682 |
| ASSLPDTQY | SEQ ID NO: 2683 |
| ASSLVEETQY | SEQ ID NO: 2684 |
| ASSPGENTEAF | SEQ ID NO: 2685 |
| ASSTTVNTEAF | SEQ ID NO: 2686 |
| ASSLRGGYEQY | SEQ ID NO: 2687 |
| ASSIGGNTEAF | SEQ ID NO: 2688 |
| ASSLGAGNTIY | SEQ ID NO: 2689 |
| ASRDSSYNEQF | SEQ ID NO: 2690 |
| ASSSGTGYGYT | SEQ ID NO: 2691 |
| ASSGTGGTEAF | SEQ ID NO: 2692 |
| ASSSDRNQPQH | SEQ ID NO: 2693 |
| ASSRQGYGYT | SEQ ID NO: 2694 |
| ASSRNSNQPQH | SEQ ID NO: 2695 |
| ASSLTVNQPQH | SEQ ID NO: 2696 |
| ASRGTGNTEAF | SEQ ID NO: 2697 |
| ASSYLNTEAF | SEQ ID NO: 2698 |
| ASSLLAGSYEQY | SEQ ID NO: 2699 |
| ASSENSNQPQH | SEQ ID NO: 2700 |
| ASSRSGANVLT | SEQ ID NO: 2701 |
| ASSLAGDEQY | SEQ ID NO: 2702 |
| ASSYNTGELF | SEQ ID NO: 2703 |
| ASSFTTDTQY | SEQ ID NO: 2704 |
| ASSLAGVETQY | SEQ ID NO: 2705 |
| ASSSSGSYNEQF | SEQ ID NO: 2706 |
| ASRGGSYEQY | SEQ ID NO: 2707 |
| ASSLGDTDTQY | SEQ ID NO: 2708 |
| ASSPQGDQPQH | SEQ ID NO: 2709 |
| ASSFGGEQY | SEQ ID NO: 2710 |
| ASSLGQDYEQY | SEQ ID NO: 2711 |
| ASSRRTDTQY | SEQ ID NO: 2712 |
| ASSYRGYEQY | SEQ ID NO: 2713 |
| ASSPPGTEAF | SEQ ID NO: 2714 |
| ASSPGRLNTEAF | SEQ ID NO: 2715 |
| ASSLGDSYNEQF | SEQ ID NO: 2716 |
| ASSFRGDTEAF | SEQ ID NO: 2717 |
| ASSLDGMNTEAF | SEQ ID NO: 2718 |
| ASSQGPNQPQH | SEQ ID NO: 2719 |
| ASSRGGSYEQY | SEQ ID NO: 2720 |
| ASSLGLSSYNEQF | SEQ ID NO: 2721 |
| ASSLSGNTGELF | SEQ ID NO: 2722 |
| ASSPSGQETQY | SEQ ID NO: 2723 |
| ASSLGTGSTDTQY | SEQ ID NO: 2724 |
| ASSFVNTEAF | SEQ ID NO: 2725 |
| ASSPTGETQY | SEQ ID NO: 2726 |
| SVGGNTEAF | SEQ ID NO: 2727 |
| ASSLGGTGNTIY | SEQ ID NO: 2728 |
| ASSPGTGGTDTQY | SEQ ID NO: 2729 |
| ASSEGGYEQY | SEQ ID NO: 2730 |
| ASSPRTEAF | SEQ ID NO: 2731 |
| ASSPTGAYEQY | SEQ ID NO: 2732 |

TABLE I-continued

| Sequence | Sequence ID No |
|---|---|
| ASSLGTGYNEQF | SEQ ID NO: 2733 |
| ASSQDRDTQY | SEQ ID NO: 2734 |
| ASSEGRNTEAF | SEQ ID NO: 2735 |
| ASSPPADTQY | SEQ ID NO: 2736 |
| ASSPGTVNQPQH | SEQ ID NO: 2737 |
| ASSLARDTEAF | SEQ ID NO: 2738 |
| ASSSTGGNTEAF | SEQ ID NO: 2739 |
| ASSGGNEQF | SEQ ID NO: 2740 |
| ASSLDGTYEQY | SEQ ID NO: 2741 |
| ASSLGAGNQPQH | SEQ ID NO: 2742 |
| ASSLVSNEQF | SEQ ID NO: 2743 |
| ASSLGLAGQETQY | SEQ ID NO: 2744 |
| ASSLGPGNTEAF | SEQ ID NO: 2745 |
| ASSRTLNTEAF | SEQ ID NO: 2746 |
| ASSQDSYGYT | SEQ ID NO: 2747 |
| ASSLRGGETQY | SEQ ID NO: 2748 |
| ASSSGQGNYGYT | SEQ ID NO: 2749 |
| ASSSSMNTEAF | SEQ ID NO: 2750 |
| ASSLDRDYEQY | SEQ ID NO: 2751 |
| ASSQGQGSYEQY | SEQ ID NO: 2752 |
| ASSGTGDQPQH | SEQ ID NO: 2753 |
| ASSLDSDTQY | SEQ ID NO: 2754 |
| ASSRDTYEQY | SEQ ID NO: 2755 |
| ASSFTGTDTQY | SEQ ID NO: 2756 |
| ASSLDGSSYEQY | SEQ ID NO: 2757 |
| ASRTNTEAF | SEQ ID NO: 2758 |
| ASSRDSSNQPQH | SEQ ID NO: 2759 |
| ASSRLAGTDTQY | SEQ ID NO: 2760 |
| ASSPGTNYGYT | SEQ ID NO: 2761 |
| ASSPTSYNEQF | SEQ ID NO: 2762 |
| ASSRQGSTDTQY | SEQ ID NO: 2763 |
| ASSEADTQY | SEQ ID NO: 2764 |
| ASSLAGTNTEAF | SEQ ID NO: 2765 |
| ASSFRADTQY | SEQ ID NO: 2766 |
| ASSGNEQF | SEQ ID NO: 2767 |
| ASSLAAYEQY | SEQ ID NO: 2768 |
| ASSLQGGETQY | SEQ ID NO: 2769 |
| ASSLSPNQPQH | SEQ ID NO: 2770 |
| ASSRLAGGYNEQF | SEQ ID NO: 2771 |
| ASSPTGGSYNEQF | SEQ ID NO: 2772 |
| ASSPGTVSYEQY | SEQ ID NO: 2773 |
| ASSLASSTDTQY | SEQ ID NO: 2774 |
| ASSPRQETQY | SEQ ID NO: 2775 |
| ASSYQGNTEAF | SEQ ID NO: 2776 |
| ASSPDRSSYNEQF | SEQ ID NO: 2777 |
| ASSPDRAYGYT | SEQ ID NO: 2778 |
| ASSLGLTYEQY | SEQ ID NO: 2779 |
| ASSLGTSYNEQF | SEQ ID NO: 2780 |
| ASSSSSGNTIY | SEQ ID NO: 2781 |
| ASSLERTDTQY | SEQ ID NO: 2782 |
| ASSPRGGTDTQY | SEQ ID NO: 2783 |
| ASSPRTGGYEQY | SEQ ID NO: 2784 |
| ASSFLGTDTQY | SEQ ID NO: 2785 |
| ASSVGVNTEAF | SEQ ID NO: 2786 |
| ASSDRENTEAF | SEQ ID NO: 2787 |
| ASSLDGLNTEAF | SEQ ID NO: 2788 |
| ASSPRDRGYEQY | SEQ ID NO: 2789 |
| ASSFGTGNQPQH | SEQ ID NO: 2790 |
| ASSRTGLNTEAF | SEQ ID NO: 2791 |
| ASSLARQETQY | SEQ ID NO: 2792 |
| ASSLQPNTEAF | SEQ ID NO: 2793 |
| ASSPGQGSNQPQH | SEQ ID NO: 2794 |
| ASRRGTEAF | SEQ ID NO: 2795 |
| ASSPRQGGTEAF | SEQ ID NO: 2796 |
| ASSPGQGDQPQH | SEQ ID NO: 2797 |
| ASSQEGNQPQH | SEQ ID NO: 2798 |
| ASSFGQGSYEQY | SEQ ID NO: 2799 |
| ASSLGQGPDTQY | SEQ ID NO: 2800 |
| ASSFGTSTDTQY | SEQ ID NO: 2801 |
| ASSPGPNYGYT | SEQ ID NO: 2802 |
| ASSPGRYEQY | SEQ ID NO: 2803 |
| ASSLDLYEQY | SEQ ID NO: 2804 |
| ASSLAGGRTDTQY | SEQ ID NO: 2805 |
| ASSEGGTDTQY | SEQ ID NO: 2806 |
| ASSLEGTQY | SEQ ID NO: 2807 |
| ASSSGNTGELF | SEQ ID NO: 2808 |
| ASSLGGDGYT | SEQ ID NO: 2809 |
| ASSFGQSYEQY | SEQ ID NO: 2810 |

TABLE I-continued

| Sequence | Sequence ID No |
|---|---|
| ASSFRGDTQY | SEQ ID NO: 2811 |
| ASSFTGNQPQH | SEQ ID NO: 2812 |
| ASSRTSGQETQY | SEQ ID NO: 2813 |
| ASSLTGDGYT | SEQ ID NO: 2814 |
| ASSLHYEQY | SEQ ID NO: 2815 |
| ASSLGDGYT | SEQ ID NO: 2816 |
| ASRGGNTEAF | SEQ ID NO: 2817 |
| ASSLGREAF | SEQ ID NO: 2818 |
| ASSEDSNQPQH | SEQ ID NO: 2819 |
| ASSLGLAGSYEQY | SEQ ID NO: 2820 |
| ASRTSGSYEQY | SEQ ID NO: 2821 |
| ASSLRASTDTQY | SEQ ID NO: 2822 |
| ASSLDPYEQY | SEQ ID NO: 2823 |
| ASSLERNQPQH | SEQ ID NO: 2824 |
| ASSLVSSYNEQF | SEQ ID NO: 2825 |
| ASSGGLNTEAF | SEQ ID NO: 2826 |
| ASSETYEQY | SEQ ID NO: 2827 |
| SARRGNTEAF | SEQ ID NO: 2828 |
| ASSLGTSGSTDTQY | SEQ ID NO: 2829 |
| ASSLSGEETQY | SEQ ID NO: 2830 |
| ASSSTLNTEAF | SEQ ID NO: 2831 |
| ASSFAGTDTQY | SEQ ID NO: 2832 |
| ASSPTSGQETQY | SEQ ID NO: 2833 |
| ASSLSQPQH | SEQ ID NO: 2834 |
| ASGYEQY | SEQ ID NO: 2835 |
| ASSSGQPQH | SEQ ID NO: 2836 |
| ASSLRGSGANVLT | SEQ ID NO: 2837 |
| ASGSYNEQF | SEQ ID NO: 2838 |
| ASSLPGQETQY | SEQ ID NO: 2839 |
| ASSSNEQF | SEQ ID NO: 2840 |
| ASRGDSYEQY | SEQ ID NO: 2841 |
| ASSLQGTNTEAF | SEQ ID NO: 2842 |
| ASSLTGPDTQY | SEQ ID NO: 2843 |
| ASSLVAGNTEAF | SEQ ID NO: 2844 |
| ASSLQSTDTQY | SEQ ID NO: 2845 |
| ASSLISTDTQY | SEQ ID NO: 2846 |
| ASSYTYEQY | SEQ ID NO: 2847 |
| ASSAGLNTEAF | SEQ ID NO: 2848 |
| ASSATVNTEAF | SEQ ID NO: 2849 |
| ASSLLGGNQPQH | SEQ ID NO: 2850 |
| ASSLGRANTEAF | SEQ ID NO: 2851 |
| ASSFSGGTEAF | SEQ ID NO: 2852 |
| ASSLDRATDTQY | SEQ ID NO: 2853 |
| ASSRGYGYT | SEQ ID NO: 2854 |
| ASSIGDTQY | SEQ ID NO: 2855 |
| ASSLGPGNTIY | SEQ ID NO: 2856 |
| ASSLWGNQPQH | SEQ ID NO: 2857 |
| ASSWGNEQF | SEQ ID NO: 2858 |
| ASSLGGASYEQY | SEQ ID NO: 2859 |
| ASSLTASYEQY | SEQ ID NO: 2860 |
| ASSPSGGYNEQF | SEQ ID NO: 2861 |
| ASSFPGTEAF | SEQ ID NO: 2862 |
| ASSLGANTGELF | SEQ ID NO: 2863 |
| ASSLVAGTDTQY | SEQ ID NO: 2864 |
| ASSRENTEAF | SEQ ID NO: 2865 |
| ASSPTNTGELF | SEQ ID NO: 2866 |
| ASSLTTEAF | SEQ ID NO: 2867 |
| ASSLSGVNTEAF | SEQ ID NO: 2868 |
| ASSPGLTDTQY | SEQ ID NO: 2869 |
| ASSFGQGYGYT | SEQ ID NO: 2870 |
| ASSPRTGGTEAF | SEQ ID NO: 2871 |
| ASSSGPSYEQY | SEQ ID NO: 2872 |
| ASSYSGTDTQY | SEQ ID NO: 2873 |
| ASSSRSTDTQY | SEQ ID NO: 2874 |
| ASSLRGSTEAF | SEQ ID NO: 2875 |
| ASSLTSGYEQY | SEQ ID NO: 2876 |
| ASSLVGGGTEAF | SEQ ID NO: 2877 |
| ASSWGDTQY | SEQ ID NO: 2878 |
| ASSWDSTDTQY | SEQ ID NO: 2879 |
| ASSLSGTYNEQF | SEQ ID NO: 2880 |
| ASSPSVNTEAF | SEQ ID NO: 2881 |
| ASSLGTGSYNEQF | SEQ ID NO: 2882 |
| ASSFGTNTEAF | SEQ ID NO: 2883 |
| ASSSRTGNTEAF | SEQ ID NO: 2884 |
| ASRGDSNQPQH | SEQ ID NO: 2885 |
| ASSQVSYEQY | SEQ ID NO: 2886 |
| ASSGGGTEAF | SEQ ID NO: 2887 |
| ASSLEGSTEAF | SEQ ID NO: 2888 |

TABLE I-continued

| Sequence | Sequence ID No |
|---|---|
| ASSLSGGNEQF | SEQ ID NO: 2889 |
| ASSFQGSYEQY | SEQ ID NO: 2890 |
| ASSLQSNQPQH | SEQ ID NO: 2891 |
| ASSLAGPNTEAF | SEQ ID NO: 2892 |
| ASSLVDQPQH | SEQ ID NO: 2893 |
| ASSSSLNTEAF | SEQ ID NO: 2894 |
| ASSWTSGTDTQY | SEQ ID NO: 2895 |
| ASSSDGNTEAF | SEQ ID NO: 2896 |
| ASSFSMNTEAF | SEQ ID NO: 2897 |
| ASSLDRAGNTIY | SEQ ID NO: 2898 |
| ASSLSSSTDTQY | SEQ ID NO: 2899 |
| ASSLGDSPLH | SEQ ID NO: 2900 |
| ASSFRSNQPQH | SEQ ID NO: 2901 |
| ASSEGGNTEAF | SEQ ID NO: 2902 |
| ASSLERGTEAF | SEQ ID NO: 2903 |
| ASSLSRNEQF | SEQ ID NO: 2904 |
| ASSRQGSTEAF | SEQ ID NO: 2905 |
| ASSFRTEAF | SEQ ID NO: 2906 |
| ASSLFSNQPQH | SEQ ID NO: 2907 |
| ASSPDTGELF | SEQ ID NO: 2908 |
| ASSSRSYEQY | SEQ ID NO: 2909 |
| ASSSTGGYGYT | SEQ ID NO: 2910 |
| SARTGGTEAF | SEQ ID NO: 2911 |
| ASSRDSSTDTQY | SEQ ID NO: 2912 |
| ASSLGQENTEAF | SEQ ID NO: 2913 |
| ASSPGGPYEQY | SEQ ID NO: 2914 |
| ASSPTNTEAF | SEQ ID NO: 2915 |
| ASSLEGGYEQY | SEQ ID NO: 2916 |
| ASSLGGNSNQPQH | SEQ ID NO: 2917 |
| ASRTTDTQY | SEQ ID NO: 2918 |
| ASRSSGANVLT | SEQ ID NO: 2919 |
| ASSFGYGYT | SEQ ID NO: 2920 |
| ASSDRVNTEAF | SEQ ID NO: 2921 |
| ASSPGGGQPQH | SEQ ID NO: 2922 |
| ASSEGQPQH | SEQ ID NO: 2923 |
| ASSWTGGTEAF | SEQ ID NO: 2924 |
| ASSRTGAYEQY | SEQ ID NO: 2925 |
| ASSYSSSYEQY | SEQ ID NO: 2926 |
| ASSPGTGVYEQY | SEQ ID NO: 2927 |
| ASSLGPSSYNEQF | SEQ ID NO: 2928 |
| ASSRGGETQY | SEQ ID NO: 2929 |
| ASSLEGEQY | SEQ ID NO: 2930 |
| ASSLSRGNTEAF | SEQ ID NO: 2931 |
| ASSDRGYGYT | SEQ ID NO: 2932 |
| ASSQGRGTEAF | SEQ ID NO: 2933 |
| SARGGNQPQH | SEQ ID NO: 2934 |
| ASSLGIQETQY | SEQ ID NO: 2935 |
| ASSGDTQY | SEQ ID NO: 2936 |
| ASSLADEQF | SEQ ID NO: 2937 |
| ASRGSSYEQY | SEQ ID NO: 2938 |
| ASSLRQGSYEQY | SEQ ID NO: 2939 |
| ASSLAGDEQF | SEQ ID NO: 2940 |
| ASSGLAGGPDTQY | SEQ ID NO: 2941 |
| ASSFRGSTDTQY | SEQ ID NO: 2942 |
| ASSPDTYEQY | SEQ ID NO: 2943 |
| ASSLAGTSTDTQY | SEQ ID NO: 2944 |
| ASSFRGSGNTIY | SEQ ID NO: 2945 |
| ASSSHNEQF | SEQ ID NO: 2946 |
| ASSLTVSYEQY | SEQ ID NO: 2947 |
| ASRGDTQY | SEQ ID NO: 2948 |
| SARGDSNQPQH | SEQ ID NO: 2949 |
| ASSWTGNQPQH | SEQ ID NO: 2950 |
| ASSLGVNYGYT | SEQ ID NO: 2951 |
| ASSAGGTEAF | SEQ ID NO: 2952 |
| ASRGNEQF | SEQ ID NO: 2953 |
| ASSQGRETQY | SEQ ID NO: 2954 |
| ASSPGDQPQH | SEQ ID NO: 2955 |
| ASSLSRGTDTQY | SEQ ID NO: 2956 |
| ASSEGGTEAF | SEQ ID NO: 2957 |
| ASSSGLATDTQY | SEQ ID NO: 2958 |
| ASSLTGVTEAF | SEQ ID NO: 2959 |
| ASSSPGQYEQY | SEQ ID NO: 2960 |
| ASSQVGGTEAF | SEQ ID NO: 2961 |
| ASSDGNQPQH | SEQ ID NO: 2962 |
| ASSLVGGSTDTQY | SEQ ID NO: 2963 |
| ASSSGDQPQH | SEQ ID NO: 2964 |
| ASSSRNEQF | SEQ ID NO: 2965 |
| ASRGTGELF | SEQ ID NO: 2966 |

TABLE I-continued

| Sequence | Sequence ID No |
|---|---|
| ASSFDSYNEQF | SEQ ID NO: 2967 |
| ASSGQVNTEAF | SEQ ID NO: 2968 |
| ASSSSNEQF | SEQ ID NO: 2969 |
| ASSFGGYNEQF | SEQ ID NO: 2970 |
| ASSLGGQGYEQY | SEQ ID NO: 2971 |
| ASSLGGYTDTQY | SEQ ID NO: 2972 |
| ASSLPGNTIY | SEQ ID NO: 2973 |
| ASSDSYNEQF | SEQ ID NO: 2974 |
| ASSIGNQPQH | SEQ ID NO: 2975 |
| ASSLGQGATEAF | SEQ ID NO: 2976 |
| ASSPGTGDYEQY | SEQ ID NO: 2977 |
| ASRDSTDTQY | SEQ ID NO: 2978 |
| ASSFGTAYEQY | SEQ ID NO: 2979 |
| ASSPSRNTEAF | SEQ ID NO: 2980 |
| ASSPRDRAYEQY | SEQ ID NO: 2981 |
| ASSLDYTDTQY | SEQ ID NO: 2982 |
| ASSRTGMNTEAF | SEQ ID NO: 2983 |
| ASSPSGGTEAF | SEQ ID NO: 2984 |
| ASSPSGYNEQF | SEQ ID NO: 2985 |
| ASSLGLGETQY | SEQ ID NO: 2986 |
| ASSPDRQETQY | SEQ ID NO: 2987 |
| ASSSRYNEQF | SEQ ID NO: 2988 |
| ASSFRGSNQPQH | SEQ ID NO: 2989 |
| ASSQDRNYGYT | SEQ ID NO: 2990 |
| ASSLALTDTQY | SEQ ID NO: 2991 |
| ASSLREETQY | SEQ ID NO: 2992 |
| ASSPRYNEQF | SEQ ID NO: 2993 |
| ASSQDRSYEQY | SEQ ID NO: 2994 |
| ASSGGYNEQF | SEQ ID NO: 2995 |
| ASSPDMNTEAF | SEQ ID NO: 2996 |
| ASSLTGTGELF | SEQ ID NO: 2997 |
| ASSLIETQY | SEQ ID NO: 2998 |
| ASSFLGQPQH | SEQ ID NO: 2999 |
| ASSSDTEAF | SEQ ID NO: 3000 |
| ASSLARGNTEAF | SEQ ID NO: 3001 |
| ASSTGGNQPQH | SEQ ID NO: 3002 |
| ASSFSTGELF | SEQ ID NO: 3003 |
| ASSQDRYNEQF | SEQ ID NO: 3004 |
| ASSLGANEQF | SEQ ID NO: 3005 |
| ASSPGTVYEQY | SEQ ID NO: 3006 |
| ASSQYSNQPQH | SEQ ID NO: 3007 |
| ASSYRDTQY | SEQ ID NO: 3008 |
| ASRSNTEAF | SEQ ID NO: 3009 |
| ASRQGLNTEAF | SEQ ID NO: 3010 |
| ASSLLAGGYEQY | SEQ ID NO: 3011 |
| ASRTSGSTDTQY | SEQ ID NO: 3012 |
| ASSRQGDQPQH | SEQ ID NO: 3013 |
| ASSLGGTNEKLF | SEQ ID NO: 3014 |
| ASSPQGQETQY | SEQ ID NO: 3015 |
| ASSPTGTEAF | SEQ ID NO: 3016 |
| ASSLGRGQPQH | SEQ ID NO: 3017 |
| ASSLGLMNTEAF | SEQ ID NO: 3018 |
| ASSQAGTDTQY | SEQ ID NO: 3019 |
| ASSLQSSYNEQF | SEQ ID NO: 3020 |
| ASSVTVNTEAF | SEQ ID NO: 3021 |
| ASSLGTAYNEQF | SEQ ID NO: 3022 |
| ASSPGTGELF | SEQ ID NO: 3023 |
| ASSFGEKLF | SEQ ID NO: 3024 |
| ASSLTRTDTQY | SEQ ID NO: 3025 |
| ASSLAGGGYEQY | SEQ ID NO: 3026 |
| ASSLWGTDTQY | SEQ ID NO: 3027 |
| ASSSTGSGNTIY | SEQ ID NO: 3028 |
| ASSYGGSNQPQH | SEQ ID NO: 3029 |
| ASSRDGSYEQY | SEQ ID NO: 3030 |
| ASSLGGGNQPQH | SEQ ID NO: 3031 |
| ASGTDTQY | SEQ ID NO: 3032 |
| ASSRGQLNTEAF | SEQ ID NO: 3033 |
| ASSQGAEAF | SEQ ID NO: 3034 |
| ASRQETQY | SEQ ID NO: 3035 |
| ASSRPQETQY | SEQ ID NO: 3036 |
| ASSLVRGNTEAF | SEQ ID NO: 3037 |
| ASSGQGSNQPQH | SEQ ID NO: 3038 |
| ASSLTVQETQY | SEQ ID NO: 3039 |
| ASSSQGGNQPQH | SEQ ID NO: 3040 |
| ASSRQGSYNEQF | SEQ ID NO: 3041 |
| ASSSDSSYEQY | SEQ ID NO: 3042 |
| ASSPGRDTQY | SEQ ID NO: 3043 |
| ASSYGSTDTQY | SEQ ID NO: 3044 |

TABLE I-continued

| Sequence | Sequence ID No |
|---|---|
| ASSYNEQF | SEQ ID NO: 3045 |
| ASSQEGGTEAF | SEQ ID NO: 3046 |
| ASSRGQGNPQH | SEQ ID NO: 3047 |
| ASSLQYEQY | SEQ ID NO: 3048 |
| ASSYLDTQY | SEQ ID NO: 3049 |
| ASSPQGYNEQF | SEQ ID NO: 3050 |
| ASSSGTSGYEQY | SEQ ID NO: 3051 |
| ASSFGGYGYT | SEQ ID NO: 3052 |
| ASSPRGLNTEAF | SEQ ID NO: 3053 |
| ASSGTENTEAF | SEQ ID NO: 3054 |
| ASSQDRGETQY | SEQ ID NO: 3055 |
| ASSQVQETQY | SEQ ID NO: 3056 |
| ASSLGSMNTEAF | SEQ ID NO: 3057 |
| ASSLLRETQY | SEQ ID NO: 3058 |
| ASSLADNEQF | SEQ ID NO: 3059 |
| ASSLQGSYGYT | SEQ ID NO: 3060 |
| ASSLLTEAF | SEQ ID NO: 3061 |
| ASSLAGASYEQY | SEQ ID NO: 3062 |
| ASSPDREETQY | SEQ ID NO: 3063 |
| ASSPGQSSYEQY | SEQ ID NO: 3064 |
| ASSLRGEAF | SEQ ID NO: 3065 |
| ASSLTSGAYNEQF | SEQ ID NO: 3066 |
| ASSLVGDEQF | SEQ ID NO: 3067 |
| ASSFGSGNTIY | SEQ ID NO: 3068 |
| ASSWGQGNTEAF | SEQ ID NO: 3069 |
| ASSPRQGAYEQY | SEQ ID NO: 3070 |
| ASSPYYEQY | SEQ ID NO: 3071 |
| ASSLVASTDTQY | SEQ ID NO: 3072 |
| ASSVGNQPQH | SEQ ID NO: 3073 |
| ASSLNNSPLH | SEQ ID NO: 3074 |
| ASSISGSSYNEQF | SEQ ID NO: 3075 |
| ASSPGTGSNQPQH | SEQ ID NO: 3076 |
| ASSLGLAGTYEQY | SEQ ID NO: 3077 |
| ASSLAVSYEQY | SEQ ID NO: 3078 |
| ASSPRQGTDTQY | SEQ ID NO: 3079 |
| ASSYRGNEQF | SEQ ID NO: 3080 |
| ASSFSGDTQY | SEQ ID NO: 3081 |
| ASSPGRTDTQY | SEQ ID NO: 3082 |
| ASSLDRDNEQF | SEQ ID NO: 3083 |
| ASSPGGNTIY | SEQ ID NO: 3084 |
| ASSENTGELF | SEQ ID NO: 3085 |
| ASSLLAGAYEQY | SEQ ID NO: 3086 |
| ASSSSGSYEQY | SEQ ID NO: 3087 |
| ASSLPGTEAF | SEQ ID NO: 3088 |
| ASSLNSQETQY | SEQ ID NO: 3089 |
| ASSPRGSNQPQH | SEQ ID NO: 3090 |
| ASSLIGNTEAF | SEQ ID NO: 3091 |
| ASSSLSTDTQY | SEQ ID NO: 3092 |
| ASSLRTGQETQY | SEQ ID NO: 3093 |
| ASSQGGSYNEQF | SEQ ID NO: 3094 |
| ASSLGQGGEKLF | SEQ ID NO: 3095 |
| ASRPSTDTQY | SEQ ID NO: 3096 |
| ASSESNQPQH | SEQ ID NO: 3097 |
| ASSPTMNTEAF | SEQ ID NO: 3098 |
| ASSSRVNTEAF | SEQ ID NO: 3099 |
| ASSRTGTYEQY | SEQ ID NO: 3100 |
| ASSEQGNQPQH | SEQ ID NO: 3101 |
| ASSLYSYEQY | SEQ ID NO: 3102 |
| ASSLAGGGNEQF | SEQ ID NO: 3103 |
| ASSLLAGADTQY | SEQ ID NO: 3104 |
| ASSQGTGNQPQH | SEQ ID NO: 3105 |
| ASSETGNTEAF | SEQ ID NO: 3106 |
| ASSPLAGAYNEQF | SEQ ID NO: 3107 |
| ASSEGGNQPQH | SEQ ID NO: 3108 |
| ASSSRGETQY | SEQ ID NO: 3109 |
| ASSYSGGSYEQY | SEQ ID NO: 3110 |
| ASSLENEQF | SEQ ID NO: 3111 |
| ASSFRQNTEAF | SEQ ID NO: 3112 |
| ASSLRGTYEQY | SEQ ID NO: 3113 |
| ASSLAGTTDTQY | SEQ ID NO: 3114 |
| ASSPGTSYNEQF | SEQ ID NO: 3115 |
| ASSLDRNTGELF | SEQ ID NO: 3116 |
| ASSFGGDTEAF | SEQ ID NO: 3117 |
| ASSSGQSTDTQY | SEQ ID NO: 3118 |
| ASSLADQPQH | SEQ ID NO: 3119 |
| ASSLTSGSSYEQY | SEQ ID NO: 3120 |
| ASSLHTDTQY | SEQ ID NO: 3121 |
| ASSQALNTEAF | SEQ ID NO: 3122 |

TABLE I-continued

| Sequence | Sequence ID No |
|---|---|
| ASSFNEQF | SEQ ID NO: 3123 |
| ASSLVAGGYNEQF | SEQ ID NO: 3124 |
| ASSAGQNTEAF | SEQ ID NO: 3125 |
| ASSLGPLNTEAF | SEQ ID NO: 3126 |
| ASSSTGYNEQF | SEQ ID NO: 3127 |
| ASSWGSNQPQH | SEQ ID NO: 3128 |
| ASSLAVTDTQY | SEQ ID NO: 3129 |
| ASSQGQLNTEAF | SEQ ID NO: 3130 |
| ASSQVRETQY | SEQ ID NO: 3131 |
| ASSSGLSYEQY | SEQ ID NO: 3132 |
| ASSPENTEAF | SEQ ID NO: 3133 |
| ASSLDSTYEQY | SEQ ID NO: 3134 |
| ASSSLYNEQF | SEQ ID NO: 3135 |
| ASSPQDTQY | SEQ ID NO: 3136 |
| ASSPGLEETQY | SEQ ID NO: 3137 |
| ASSRQGNEQF | SEQ ID NO: 3138 |
| ASSSPNTEAF | SEQ ID NO: 3139 |
| ASSLGGYQPQH | SEQ ID NO: 3140 |
| ASSLALQETQY | SEQ ID NO: 3141 |
| ASSLSPTDTQY | SEQ ID NO: 3142 |
| ASSPPGGNQPQH | SEQ ID NO: 3143 |
| ASRGSYNEQF | SEQ ID NO: 3144 |
| ASSRDSGNTIY | SEQ ID NO: 3145 |
| ASSDSYGYT | SEQ ID NO: 3146 |
| SASGSSYNEQF | SEQ ID NO: 3147 |
| ASSLINQPQH | SEQ ID NO: 3148 |
| ASSSGGSSYNEQF | SEQ ID NO: 3149 |
| ASSPLSYEQY | SEQ ID NO: 3150 |
| ASSLTDNQPQH | SEQ ID NO: 3151 |
| ASSLGGLETQY | SEQ ID NO: 3152 |
| ASSPVTDTQY | SEQ ID NO: 3153 |
| ASSLGLSNQPQH | SEQ ID NO: 3154 |
| SASRETQY | SEQ ID NO: 3155 |
| ASSPGLAAYNEQF | SEQ ID NO: 3156 |
| ASSRGGSNQPQH | SEQ ID NO: 3157 |
| ASSPRTGTDTQY | SEQ ID NO: 3158 |
| ASSSQGNYGYT | SEQ ID NO: 3159 |
| ASSPRGGETQY | SEQ ID NO: 3160 |
| ASSQGGSTDTQY | SEQ ID NO: 3161 |
| ASSLAGQNTEAF | SEQ ID NO: 3162 |
| ASRDRGNQPQH | SEQ ID NO: 3163 |
| ASSDRLNTEAF | SEQ ID NO: 3164 |
| ASSLDRGDTQY | SEQ ID NO: 3165 |
| ASSLSTNTEAF | SEQ ID NO: 3166 |
| ASSLNRGTEAF | SEQ ID NO: 3167 |
| ASSLGGYQETQY | SEQ ID NO: 3168 |
| ASSLAGAGNTIY | SEQ ID NO: 3169 |
| ASSLRGDEQF | SEQ ID NO: 3170 |
| ASSFGPDTQY | SEQ ID NO: 3171 |
| ASRRDTEAF | SEQ ID NO: 3172 |
| ASSYSQETQY | SEQ ID NO: 3173 |
| ASSMNTEAF | SEQ ID NO: 3174 |
| ASSLAGNNEQF | SEQ ID NO: 3175 |
| ASSFSGETQY | SEQ ID NO: 3176 |
| ASSLGQYEQY | SEQ ID NO: 3177 |
| ASSLGLAKNIQY | SEQ ID NO: 3178 |
| ASSYADTQY | SEQ ID NO: 3179 |
| ASSYSMNTEAF | SEQ ID NO: 3180 |
| ASSSDRAYEQY | SEQ ID NO: 3181 |
| ASSEGSTDTQY | SEQ ID NO: 3182 |
| ASSLVSSTDTQY | SEQ ID NO: 3183 |
| ASSFGTSYEQY | SEQ ID NO: 3184 |
| ASSSSGGSYNEQF | SEQ ID NO: 3185 |
| ASSGPYEQY | SEQ ID NO: 3186 |
| ASSLAGTQETQY | SEQ ID NO: 3187 |
| ASSHGETQY | SEQ ID NO: 3188 |
| ASSPRDEQF | SEQ ID NO: 3189 |
| ASSLDRTEAF | SEQ ID NO: 3190 |
| ASSSGGSGNTIY | SEQ ID NO: 3191 |
| ASSQVGTDTQY | SEQ ID NO: 3192 |
| ASRLAGGNEQF | SEQ ID NO: 3193 |
| ASSSQNTEAF | SEQ ID NO: 3194 |
| ASSLGTAGNTIY | SEQ ID NO: 3195 |
| ASSLVSQETQY | SEQ ID NO: 3196 |
| ASSLYNQPQH | SEQ ID NO: 3197 |
| ASSRDFTDTQY | SEQ ID NO: 3198 |
| ASSLAGVYEQY | SEQ ID NO: 3199 |
| ASSGDRNTEAF | SEQ ID NO: 3200 |

TABLE I-continued

| Sequence | Sequence ID No |
|---|---|
| ASSYRGGTEAF | SEQ ID NO: 3201 |
| ASSLGLADNEQF | SEQ ID NO: 3202 |
| ASSLTTNTEAF | SEQ ID NO: 3203 |
| ASSPGQNYEQY | SEQ ID NO: 3204 |
| ASSLGQGNTGELF | SEQ ID NO: 3205 |
| ASSPGLAQETQY | SEQ ID NO: 3206 |
| ASSLDPSTDTQY | SEQ ID NO: 3207 |
| ASSTAYEQY | SEQ ID NO: 3208 |
| ASSLAAYNEQF | SEQ ID NO: 3209 |
| ASSLTGGDTEAF | SEQ ID NO: 3210 |
| ASSLGTVYEQY | SEQ ID NO: 3211 |
| ASSGLAGYNEQF | SEQ ID NO: 3212 |
| ASSLGRDYGYT | SEQ ID NO: 3213 |
| ASSRQGGQPQH | SEQ ID NO: 3214 |
| ASSWDRGYEQY | SEQ ID NO: 3215 |
| ASSRSGSSYNEQF | SEQ ID NO: 3216 |
| ASSRGPQETQY | SEQ ID NO: 3217 |
| ASSYGNQPQH | SEQ ID NO: 3218 |
| ASSLTNYGYT | SEQ ID NO: 3219 |
| ASSFTANTEAF | SEQ ID NO: 3220 |
| ASSRGNTIY | SEQ ID NO: 3221 |
| ASSPLAGSYNEQF | SEQ ID NO: 3222 |
| ASSLGQGVYEQY | SEQ ID NO: 3223 |
| ASSPGGGNTEAF | SEQ ID NO: 3224 |
| ASSPQLNTEAF | SEQ ID NO: 3225 |
| ASSTRTDTQY | SEQ ID NO: 3226 |
| ASSSGQPNTEAF | SEQ ID NO: 3227 |
| ASSLGHSYEQY | SEQ ID NO: 3228 |
| ASSSTSGSYEQY | SEQ ID NO: 3229 |
| ASSFGTGAYEQY | SEQ ID NO: 3230 |
| ASSGLNTEAF | SEQ ID NO: 3231 |
| ASSLDRATEAF | SEQ ID NO: 3232 |
| ASSPGSNTEAF | SEQ ID NO: 3233 |
| ASSLADTEAF | SEQ ID NO: 3234 |
| ASSLGLAGAYEQY | SEQ ID NO: 3235 |
| ASSLVPTDTQY | SEQ ID NO: 3236 |
| ASSTGGYEQY | SEQ ID NO: 3237 |
| ASSRTANYGYT | SEQ ID NO: 3238 |
| ASSRNYGYT | SEQ ID NO: 3239 |
| ASSPGTGDQPQH | SEQ ID NO: 3240 |
| ASSLGQGQPQH | SEQ ID NO: 3241 |
| ASSPGTANQPQH | SEQ ID NO: 3242 |
| ASSRNEQF | SEQ ID NO: 3243 |
| ASSIRETQY | SEQ ID NO: 3244 |
| ASSLRQGAYEQY | SEQ ID NO: 3245 |
| ASSLGGPQETQY | SEQ ID NO: 3246 |
| ASSLSSQETQY | SEQ ID NO: 3247 |
| ASSLAGDYEQY | SEQ ID NO: 3248 |
| ASSLTSGTYNEQF | SEQ ID NO: 3249 |
| ASSLRDNEQF | SEQ ID NO: 3250 |
| ASSQEGTDTQY | SEQ ID NO: 3251 |
| ASRTGLNTEAF | SEQ ID NO: 3252 |
| ASSLGFQETQY | SEQ ID NO: 3253 |
| ASSSGQGGTEAF | SEQ ID NO: 3254 |
| ASSLAGDYGYT | SEQ ID NO: 3255 |
| ASSFGQTYEQY | SEQ ID NO: 3256 |
| ASSLIGYEQY | SEQ ID NO: 3257 |
| ASSQGGGTDTQY | SEQ ID NO: 3258 |
| ASSFGNSPLH | SEQ ID NO: 3259 |
| ASSTSGSTDTQY | SEQ ID NO: 3260 |
| ASSYRLNTEAF | SEQ ID NO: 3261 |
| ASSPAGNTEAF | SEQ ID NO: 3262 |
| ASRYTDTQY | SEQ ID NO: 3263 |
| ASSTGMNTEAF | SEQ ID NO: 3264 |
| ASSGTGGYEQY | SEQ ID NO: 3265 |
| ASSLGQGGTDTQY | SEQ ID NO: 3266 |
| ASSYGSSYNEQF | SEQ ID NO: 3267 |
| ASSPTGELF | SEQ ID NO: 3268 |
| ASSSGTSSYNEQF | SEQ ID NO: 3269 |
| ASSGQSNQPQH | SEQ ID NO: 3270 |
| ASSRDYQETQY | SEQ ID NO: 3271 |
| ASSPRTGTYEQY | SEQ ID NO: 3272 |
| ASSLGENQPQH | SEQ ID NO: 3273 |
| ASSFSSGANVLT | SEQ ID NO: 3274 |
| ASSRYTDTQY | SEQ ID NO: 3275 |
| ASSWDSYNEQF | SEQ ID NO: 3276 |
| ASSPGAQETQY | SEQ ID NO: 3277 |
| ASSPGGTYEQY | SEQ ID NO: 3278 |

TABLE I-continued

| Sequence | Sequence ID No |
|---|---|
| ASSLTEETQY | SEQ ID NO: 3279 |
| ASSQGYTEAF | SEQ ID NO: 3280 |
| ASSVGGTEAF | SEQ ID NO: 3281 |
| ASSPGQGGYGYT | SEQ ID NO: 3282 |
| ASSLGGGNTIY | SEQ ID NO: 3283 |
| ASSFGTGNTEAF | SEQ ID NO: 3284 |
| ASSPDSSGNTIY | SEQ ID NO: 3285 |
| ASSLTGQPQH | SEQ ID NO: 3286 |
| ASSPRGQPQH | SEQ ID NO: 3287 |
| ASSPGGGYGYT | SEQ ID NO: 3288 |
| ASSLIQETQY | SEQ ID NO: 3289 |
| ASSWGGNTEAF | SEQ ID NO: 3290 |
| ASSSTGSTDTQY | SEQ ID NO: 3291 |
| ASSLTDSYEQY | SEQ ID NO: 3292 |
| ASSLGGGTYEQY | SEQ ID NO: 3293 |
| ASSLGGGGTDTQY | SEQ ID NO: 3294 |
| ASSSTSGSTDTQY | SEQ ID NO: 3295 |
| ASSLGVEQY | SEQ ID NO: 3296 |
| ASSEAGGTDTQY | SEQ ID NO: 3297 |
| ASSPDRGSYNEQF | SEQ ID NO: 3298 |
| ASSSDLNTEAF | SEQ ID NO: 3299 |
| ASSFSQETQY | SEQ ID NO: 3300 |
| ASSPPGYNEQF | SEQ ID NO: 3301 |
| ASSPGRDQPQH | SEQ ID NO: 3302 |
| ASSLTATNEKLF | SEQ ID NO: 3303 |
| ASSPGGEQF | SEQ ID NO: 3304 |
| ASSLGPEQY | SEQ ID NO: 3305 |
| ASRQGGTEAF | SEQ ID NO: 3306 |
| ASSLGGQNTEAF | SEQ ID NO: 3307 |
| ASSLDRNNEQF | SEQ ID NO: 3308 |
| ASSSNSPLH | SEQ ID NO: 3309 |
| ASSFHNEQF | SEQ ID NO: 3310 |
| ASSLGPGTEAF | SEQ ID NO: 3311 |
| ASSLSYQETQY | SEQ ID NO: 3312 |
| ASSLGGGAYEQY | SEQ ID NO: 3313 |
| SARDRGYEQY | SEQ ID NO: 3314 |
| ASSPGQSSYNEQF | SEQ ID NO: 3315 |
| ASSIQGNQPQH | SEQ ID NO: 3316 |
| ASSNYEQY | SEQ ID NO: 3317 |
| ASSYGTGGYEQY | SEQ ID NO: 3318 |
| ASSLRGNTIY | SEQ ID NO: 3319 |
| ASSLDSGANVLT | SEQ ID NO: 3320 |
| ASSFPGQPQH | SEQ ID NO: 3321 |
| ASSWTSGSYEQY | SEQ ID NO: 3322 |
| ASSRTSGTYEQY | SEQ ID NO: 3323 |
| ASSPLAGSTDTQY | SEQ ID NO: 3324 |
| ASSGTGYEQY | SEQ ID NO: 3325 |
| ASSFRGEQY | SEQ ID NO: 3326 |
| ASSLDLNQPQH | SEQ ID NO: 3327 |
| ASSSPGQGSYEQY | SEQ ID NO: 3328 |
| ASSGQGGQPQH | SEQ ID NO: 3329 |
| AISESTDTQY | SEQ ID NO: 3330 |
| ASSLLGQETQY | SEQ ID NO: 3331 |
| ASSAGNQPQH | SEQ ID NO: 3332 |
| ASSYGGSSYEQY | SEQ ID NO: 3333 |
| ASSLSASTDTQY | SEQ ID NO: 3334 |
| ASSSDRGTEAF | SEQ ID NO: 3335 |
| ASSLTSSTDTQY | SEQ ID NO: 3336 |
| ASSQGLAGTDTQY | SEQ ID NO: 3337 |
| ASRLAGTDTQY | SEQ ID NO: 3338 |
| ASSSDRGYGYT | SEQ ID NO: 3339 |
| ASSDSSGSTDTQY | SEQ ID NO: 3340 |
| ASRQGSYEQY | SEQ ID NO: 3341 |
| ASSLGGANYGYT | SEQ ID NO: 3342 |
| ASSSRGDTQY | SEQ ID NO: 3343 |
| ASSPGLAGSTDTQY | SEQ ID NO: 3344 |
| ASSLTGATEAF | SEQ ID NO: 3345 |
| ASSSNNQPQH | SEQ ID NO: 3346 |
| ASSLASGSTDTQY | SEQ ID NO: 3347 |
| ASSLQGSSYNEQF | SEQ ID NO: 3348 |
| ASSSDRDTEAF | SEQ ID NO: 3349 |
| ASSSETQY | SEQ ID NO: 3350 |
| ASSVTYEQY | SEQ ID NO: 3351 |
| ASSRDFQETQY | SEQ ID NO: 3352 |
| ASSLASNTEAF | SEQ ID NO: 3353 |
| ASSQVRNTEAF | SEQ ID NO: 3354 |
| ASSWDSYEQY | SEQ ID NO: 3355 |
| ASSSTGSSYEQY | SEQ ID NO: 3356 |

TABLE I-continued

| Sequence | Sequence ID No |
|---|---|
| ASSLGGAGANVLT | SEQ ID NO: 3357 |
| ASSIGGSSYNEQF | SEQ ID NO: 3358 |
| ASSLAPNQPQH | SEQ ID NO: 3359 |
| ASSLGGSSTDTQY | SEQ ID NO: 3360 |
| ASSLGSGELF | SEQ ID NO: 3361 |
| ASSRGGNEQF | SEQ ID NO: 3362 |
| ASSQEGETQY | SEQ ID NO: 3363 |
| ASSRDMNTEAF | SEQ ID NO: 3364 |
| ASRLYNEQF | SEQ ID NO: 3365 |
| ASSLGRGYGYT | SEQ ID NO: 3366 |
| ASSLRDRGYEQY | SEQ ID NO: 3367 |
| SARGGTEAF | SEQ ID NO: 3368 |
| ASSLGVETQY | SEQ ID NO: 3369 |
| ASRGDTEAF | SEQ ID NO: 3370 |
| ASSLTGGYNEQF | SEQ ID NO: 3371 |
| ASSLGSGTEAF | SEQ ID NO: 3372 |
| ASSLATYEQY | SEQ ID NO: 3373 |
| ASSPRQGPYEQY | SEQ ID NO: 3374 |
| ASSFGSSGNTIY | SEQ ID NO: 3375 |
| ASSQKETQY | SEQ ID NO: 3376 |
| ASSLSSGTDTQY | SEQ ID NO: 3377 |
| ASSLGQVYEQY | SEQ ID NO: 3378 |
| ASSQGGNYGYT | SEQ ID NO: 3379 |
| ASSLGGAGTEAF | SEQ ID NO: 3380 |
| ASSQVGQPQH | SEQ ID NO: 3381 |
| ASSRDRLNTEAF | SEQ ID NO: 3382 |
| ASSTGGNTEAF | SEQ ID NO: 3383 |
| ASSLGLASTDTQY | SEQ ID NO: 3384 |
| ASSLEVNQPQH | SEQ ID NO: 3385 |
| ASSQGSSYNEQF | SEQ ID NO: 3386 |
| ASSELAGGYNEQF | SEQ ID NO: 3387 |
| ASSSSGDTQY | SEQ ID NO: 3388 |
| ASSYRGSYEQY | SEQ ID NO: 3389 |
| ASSLEGSYNEQF | SEQ ID NO: 3390 |
| ASSPSTEAF | SEQ ID NO: 3391 |
| ASRLQETQY | SEQ ID NO: 3392 |
| ASSSTGDTEAF | SEQ ID NO: 3393 |
| ASGSSYEQY | SEQ ID NO: 3394 |
| ASSGTSGSYEQY | SEQ ID NO: 3395 |
| ASSQGLAGSYEQY | SEQ ID NO: 3396 |
| ASSLGPSNQPQH | SEQ ID NO: 3397 |
| ASSLRTSTDTQY | SEQ ID NO: 3398 |
| ASSLRGRNTEAF | SEQ ID NO: 3399 |
| ASSLKGDTEAF | SEQ ID NO: 3400 |
| ASSFEGNTEAF | SEQ ID NO: 3401 |
| ASSLYGNTEAF | SEQ ID NO: 3402 |
| ASSFSGQPQH | SEQ ID NO: 3403 |
| ASSFLAGTDTQY | SEQ ID NO: 3404 |
| ASSLPGANVLT | SEQ ID NO: 3405 |
| ASSLTGYSNQPQH | SEQ ID NO: 3406 |
| ASSLGQLYGYT | SEQ ID NO: 3407 |
| ASSGDTDTQY | SEQ ID NO: 3408 |
| ASSLGSTYEQY | SEQ ID NO: 3409 |
| ASSLGGKETQY | SEQ ID NO: 3410 |
| ASSLGLEETQY | SEQ ID NO: 3411 |
| ASSSDNEQF | SEQ ID NO: 3412 |
| ASSLVGGSYNEQF | SEQ ID NO: 3413 |
| ASSSNQETQY | SEQ ID NO: 3414 |
| ASSLGQQNTEAF | SEQ ID NO: 3415 |
| ASSQGPQETQY | SEQ ID NO: 3416 |
| ASSLWENTEAF | SEQ ID NO: 3417 |
| ASSLGPGTDTQY | SEQ ID NO: 3418 |
| ASSPRTSGYNEQF | SEQ ID NO: 3419 |
| ASSLTGGADTQY | SEQ ID NO: 3420 |
| ASSVGMNTEAF | SEQ ID NO: 3421 |
| ASSQMNTEAF | SEQ ID NO: 3422 |
| ASSFGTVNTEAF | SEQ ID NO: 3423 |
| ASSLSYSNQPQH | SEQ ID NO: 3424 |
| ASSFLGETQY | SEQ ID NO: 3425 |
| ASSLDGGTEAF | SEQ ID NO: 3426 |
| ASSPGQSYGYT | SEQ ID NO: 3427 |
| ASSLVSGNTIY | SEQ ID NO: 3428 |
| ASTNTDTQY | SEQ ID NO: 3429 |
| ASSLAQGNTEAF | SEQ ID NO: 3430 |
| ASSRRDTQY | SEQ ID NO: 3431 |
| ASSYGGSTDTQY | SEQ ID NO: 3432 |
| ASSTGSNQPQH | SEQ ID NO: 3433 |
| ASRVTDTQY | SEQ ID NO: 3434 |

TABLE I-continued

| Sequence | Sequence ID No |
|---|---|
| ASSLSGGGTEAF | SEQ ID NO: 3435 |
| ASSSGTGTDTQY | SEQ ID NO: 3436 |
| ASSQVGDTQY | SEQ ID NO: 3437 |
| ASSVGPNTEAF | SEQ ID NO: 3438 |
| ASSDSNTGELF | SEQ ID NO: 3439 |
| ASSLSDQPQH | SEQ ID NO: 3440 |
| ASSPGLTYEQY | SEQ ID NO: 3441 |
| ASSLDGTEAF | SEQ ID NO: 3442 |
| ASSQGYSNQPQH | SEQ ID NO: 3443 |
| ASSLGGSEAF | SEQ ID NO: 3444 |
| ASSLGLASYEQY | SEQ ID NO: 3445 |
| ASSYSSGNTIY | SEQ ID NO: 3446 |
| ASRGLNTEAF | SEQ ID NO: 3447 |
| ASSFRDQPQH | SEQ ID NO: 3448 |
| ASSLVSETQY | SEQ ID NO: 3449 |
| ASSPGDEQY | SEQ ID NO: 3450 |
| ASSLAQGYEQY | SEQ ID NO: 3451 |
| ASSLGLGTEAF | SEQ ID NO: 3452 |
| ASSLAGDTDTQY | SEQ ID NO: 3453 |
| ASSRTGNTGELF | SEQ ID NO: 3454 |
| ASSPAGTDTQY | SEQ ID NO: 3455 |
| ASSLRGDYGYT | SEQ ID NO: 3456 |
| ASSQQGGTEAF | SEQ ID NO: 3457 |
| ASSLGGRNQPQH | SEQ ID NO: 3458 |
| ASSLVRDTEAF | SEQ ID NO: 3459 |
| ASSLLDTEAF | SEQ ID NO: 3460 |
| ASSQAGNTEAF | SEQ ID NO: 3461 |
| ASSLGLNYGYT | SEQ ID NO: 3462 |
| ASSWTSGSTDTQY | SEQ ID NO: 3463 |
| ASSLGEQF | SEQ ID NO: 3464 |
| ASSLLRDTQY | SEQ ID NO: 3465 |
| ASSPSGGSYEQY | SEQ ID NO: 3466 |
| ASRGGGTDTQY | SEQ ID NO: 3467 |
| ASSLGPSSYEQY | SEQ ID NO: 3468 |
| ASSGQANTEAF | SEQ ID NO: 3469 |
| ASSQDTEAF | SEQ ID NO: 3470 |
| ASSPGANYGYT | SEQ ID NO: 3471 |
| SARDSSYEQY | SEQ ID NO: 3472 |
| ASSQGSYGYT | SEQ ID NO: 3473 |
| ASSLRPDTQY | SEQ ID NO: 3474 |
| ASSQGTNTEAF | SEQ ID NO: 3475 |
| ASSQDYNEQF | SEQ ID NO: 3476 |
| ASSQRDTQY | SEQ ID NO: 3477 |
| ASSQDRGDTQY | SEQ ID NO: 3478 |
| ASSVGTEAF | SEQ ID NO: 3479 |
| ASSLRPYEQY | SEQ ID NO: 3480 |
| ASSGNYGYT | SEQ ID NO: 3481 |
| ASSQGLAGYNEQF | SEQ ID NO: 3482 |
| ASSETVNTEAF | SEQ ID NO: 3483 |
| ASSAGGTDTQY | SEQ ID NO: 3484 |
| ASSLAGLTDTQY | SEQ ID NO: 3485 |
| ASSLRENQPQH | SEQ ID NO: 3486 |
| ASSLGHTDTQY | SEQ ID NO: 3487 |
| ASSQGLYNEQF | SEQ ID NO: 3488 |
| ASSLLAGQETQY | SEQ ID NO: 3489 |
| ASSLGFYEQY | SEQ ID NO: 3490 |
| ASSLGVGQPQH | SEQ ID NO: 3491 |
| ASSLAGSYGYT | SEQ ID NO: 3492 |
| ASSSHTDTQY | SEQ ID NO: 3493 |
| ASSLSRQETQY | SEQ ID NO: 3494 |
| ASSRQGSSYEQY | SEQ ID NO: 3495 |
| ASSLGTGGYNEQF | SEQ ID NO: 3496 |
| ASSSGQGADTQY | SEQ ID NO: 3497 |
| ASSYGENTEAF | SEQ ID NO: 3498 |
| ASSLGGTTDTQY | SEQ ID NO: 3499 |
| ASSSDRNYGYT | SEQ ID NO: 3500 |
| ASSSGQGQETQY | SEQ ID NO: 3501 |
| ASSPGASTDTQY | SEQ ID NO: 3502 |
| ASSEGDTQY | SEQ ID NO: 3503 |
| ASSPDRSSYEQY | SEQ ID NO: 3504 |
| ASSPTGGQETQY | SEQ ID NO: 3505 |
| ASSYPDTQY | SEQ ID NO: 3506 |
| ASSPRLAGGTDTQY | SEQ ID NO: 3507 |
| ASSLPSSYEQY | SEQ ID NO: 3508 |
| ASSRTSYEQY | SEQ ID NO: 3509 |
| ASSLLAGGNEQF | SEQ ID NO: 3510 |
| ASSRDRNTGELF | SEQ ID NO: 3511 |
| ASSLHSNQPQH | SEQ ID NO: 3512 |

TABLE I-continued

| Sequence | Sequence ID No |
|---|---|
| ASSSGQGNSPLH | SEQ ID NO: 3513 |
| ASSVGNEQF | SEQ ID NO: 3514 |
| ASSGGDTQY | SEQ ID NO: 3515 |
| ASSFDGNTEAF | SEQ ID NO: 3516 |
| ASSLGLEQY | SEQ ID NO: 3517 |
| ASSVGRNTEAF | SEQ ID NO: 3518 |
| ASSPGRNYGYT | SEQ ID NO: 3519 |
| ASSRGPYEQY | SEQ ID NO: 3520 |
| ASSWTGGNQPQH | SEQ ID NO: 3521 |
| ASSLGRDNEQF | SEQ ID NO: 3522 |
| ASSLLGEQF | SEQ ID NO: 3523 |
| ASSPGQPNTEAF | SEQ ID NO: 3524 |
| ASSPTGYTEAF | SEQ ID NO: 3525 |
| ASSPAGYEQY | SEQ ID NO: 3526 |
| ASSLIGNEQF | SEQ ID NO: 3527 |
| ASSQDRGSYNEQF | SEQ ID NO: 3528 |
| ASSLAANYGYT | SEQ ID NO: 3529 |
| ASSLVLETQY | SEQ ID NO: 3530 |
| ASSIGLNTEAF | SEQ ID NO: 3531 |
| ASSLGEGTEAF | SEQ ID NO: 3532 |
| ASSFGDSNQPQH | SEQ ID NO: 3533 |
| ASSPDRVYGYT | SEQ ID NO: 3534 |
| SARDGNQPQH | SEQ ID NO: 3535 |
| ASSLRSYNEQF | SEQ ID NO: 3536 |
| ASSFGGTYEQY | SEQ ID NO: 3537 |
| ASSQTGGNQPQH | SEQ ID NO: 3538 |
| ASSLRGAYEQY | SEQ ID NO: 3539 |
| ASSQVGGNTEAF | SEQ ID NO: 3540 |
| ASSLDRGNYGYT | SEQ ID NO: 3541 |
| ASSAQGYEQY | SEQ ID NO: 3542 |
| ASSSSSGANVLT | SEQ ID NO: 3543 |
| ASSFGGADTQY | SEQ ID NO: 3544 |
| ASSLLDQPQH | SEQ ID NO: 3545 |
| ASSSSYGYT | SEQ ID NO: 3546 |
| ASSRGTYEQY | SEQ ID NO: 3547 |
| ASSTGQNTEAF | SEQ ID NO: 3548 |
| ASSIGNTEAF | SEQ ID NO: 3549 |
| ASSLVGVNTEAF | SEQ ID NO: 3550 |
| ASSPAGGTDTQY | SEQ ID NO: 3551 |
| ASSQRTDTQY | SEQ ID NO: 3552 |
| ASSLVRNEQF | SEQ ID NO: 3553 |
| ASSFGGEQF | SEQ ID NO: 3554 |
| ASSFQGSNQPQH | SEQ ID NO: 3555 |
| ASSLGTGGNEQF | SEQ ID NO: 3556 |
| ASSYEETQY | SEQ ID NO: 3557 |
| ASSAEETQY | SEQ ID NO: 3558 |
| SARQGGTEAF | SEQ ID NO: 3559 |
| ASSQVGTEAF | SEQ ID NO: 3560 |
| SAREGNQPQH | SEQ ID NO: 3561 |
| ASSLDGGNQPQH | SEQ ID NO: 3562 |
| ASSPSGGNQPQH | SEQ ID NO: 3563 |
| ASSFLAGGTDTQY | SEQ ID NO: 3564 |
| ASSGQNTEAF | SEQ ID NO: 3565 |
| ASSLNRGYEQY | SEQ ID NO: 3566 |
| ASSSRLNTEAF | SEQ ID NO: 3567 |
| ASSSGYSNQPQH | SEQ ID NO: 3568 |
| ASSLGSETQY | SEQ ID NO: 3569 |
| ASSLRQLNTEAF | SEQ ID NO: 3570 |
| ASSYSADTQY | SEQ ID NO: 3571 |
| ASSLRRTDTQY | SEQ ID NO: 3572 |
| ASSLGQGNEQY | SEQ ID NO: 3573 |
| ASSWNTEAF | SEQ ID NO: 3574 |
| ASSQGGSGNTIY | SEQ ID NO: 3575 |
| ASSPRTENTEAF | SEQ ID NO: 3576 |
| ASSQGRDQPQH | SEQ ID NO: 3577 |
| ASSLAGGNNEQF | SEQ ID NO: 3578 |
| ASSYRDTGELF | SEQ ID NO: 3579 |
| ASSFTGYEQY | SEQ ID NO: 3580 |
| ASSLGQGPYNEQF | SEQ ID NO: 3581 |
| ASSLARSYEQY | SEQ ID NO: 3582 |
| ASSLGQIYEQY | SEQ ID NO: 3583 |
| ASSLGLAVYNEQF | SEQ ID NO: 3584 |
| ASSFRDTEAF | SEQ ID NO: 3585 |
| ASSLARGYEQY | SEQ ID NO: 3586 |
| ASSSSGETQY | SEQ ID NO: 3587 |
| ASSLGSLNTEAF | SEQ ID NO: 3588 |
| ASSLTPYEQY | SEQ ID NO: 3589 |
| ASSPRSYNEQF | SEQ ID NO: 3590 |

TABLE I-continued

| Sequence | Sequence ID No |
|---|---|
| ASSLGGYEQF | SEQ ID NO: 3591 |
| ASSPGRTEAF | SEQ ID NO: 3592 |
| ASSLGTSSYEQY | SEQ ID NO: 3593 |
| ASSLAGGNTIY | SEQ ID NO: 3594 |
| ASSLASETQY | SEQ ID NO: 3595 |
| ASSLRVTDTQY | SEQ ID NO: 3596 |
| ASSLDPDTQY | SEQ ID NO: 3597 |
| ASSLGQSYNEQF | SEQ ID NO: 3598 |
| ASSLQNQPQH | SEQ ID NO: 3599 |
| ASSSRSSYEQY | SEQ ID NO: 3600 |
| ASSLISYEQY | SEQ ID NO: 3601 |
| ASSLQGRETQY | SEQ ID NO: 3602 |
| ASSLAPSYEQY | SEQ ID NO: 3603 |
| ASSYGGETQY | SEQ ID NO: 3604 |
| ASSSLGETQY | SEQ ID NO: 3605 |
| ASSQDLGYEQY | SEQ ID NO: 3606 |
| ASSPDRGQPQH | SEQ ID NO: 3607 |
| ASSLNGYEQY | SEQ ID NO: 3608 |
| ASSLGQGGEQY | SEQ ID NO: 3609 |
| ASSLRGGYGYT | SEQ ID NO: 3610 |
| ASSLGLDNEQF | SEQ ID NO: 3611 |
| ASSPQGDYGYT | SEQ ID NO: 3612 |
| ASSYRGDTEAF | SEQ ID NO: 3613 |
| ASSSYNSPLH | SEQ ID NO: 3614 |
| ASGNTEAF | SEQ ID NO: 3615 |
| ASSLSGGSTDTQY | SEQ ID NO: 3616 |
| ASSFSSSYEQY | SEQ ID NO: 3617 |
| ASSLGGLQETQY | SEQ ID NO: 3618 |
| ASSLESSYEQY | SEQ ID NO: 3619 |
| ASSLENTGELF | SEQ ID NO: 3620 |
| ASSTSSYEQY | SEQ ID NO: 3621 |
| ASSSTGDTQY | SEQ ID NO: 3622 |
| ASSLGGTSYEQY | SEQ ID NO: 3623 |
| ASSLSRSTDTQY | SEQ ID NO: 3624 |
| ASSPGGAYEQY | SEQ ID NO: 3625 |
| ASSVGGNQPQH | SEQ ID NO: 3626 |
| ASSLQQNTEAF | SEQ ID NO: 3627 |
| ASSTRETQY | SEQ ID NO: 3628 |
| ASSSRENTEAF | SEQ ID NO: 3629 |
| ASSPQGYTEAF | SEQ ID NO: 3630 |
| ASSLSHEQY | SEQ ID NO: 3631 |
| ASSPAGDTQY | SEQ ID NO: 3632 |
| ASSSGPQETQY | SEQ ID NO: 3633 |
| ASSYPNQPQH | SEQ ID NO: 3634 |
| ASSEGVNTEAF | SEQ ID NO: 3635 |
| ASSQDRGSYEQY | SEQ ID NO: 3636 |
| ASSQDPNQPQH | SEQ ID NO: 3637 |
| ASSPRTGAYEQY | SEQ ID NO: 3638 |
| ASSLARDQPQH | SEQ ID NO: 3639 |
| ASSSGLAYEQY | SEQ ID NO: 3640 |
| ASSSGAYNEQF | SEQ ID NO: 3641 |
| ASSKQETQY | SEQ ID NO: 3642 |
| ASSPPGNTIY | SEQ ID NO: 3643 |
| ASSQTGNQPQH | SEQ ID NO: 3644 |
| ASSSTSGSYNEQF | SEQ ID NO: 3645 |
| ASSLTSGTYEQY | SEQ ID NO: 3646 |
| ASSTYTDTQY | SEQ ID NO: 3647 |
| ASSLTGGSNQPQH | SEQ ID NO: 3648 |
| ASSTDSNQPQH | SEQ ID NO: 3649 |
| ASSLGGFTDTQY | SEQ ID NO: 3650 |
| ASSPGQPYEQY | SEQ ID NO: 3651 |
| ASSLGGEKLF | SEQ ID NO: 3652 |
| ASSPRSSYNEQF | SEQ ID NO: 3653 |
| ASSEGTEAF | SEQ ID NO: 3654 |
| ASSSDRGNQPQH | SEQ ID NO: 3655 |
| ASSVSNQPQH | SEQ ID NO: 3656 |
| ASSLRQQETQY | SEQ ID NO: 3657 |
| ASSLVGMNTEAF | SEQ ID NO: 3658 |
| ASSFTETQY | SEQ ID NO: 3659 |
| ASSENYEQY | SEQ ID NO: 3660 |
| ASSRKETQY | SEQ ID NO: 3661 |
| ASRTVNTEAF | SEQ ID NO: 3662 |
| ASSLGSGNQPQH | SEQ ID NO: 3663 |
| ASSQGGGYT | SEQ ID NO: 3664 |
| ASSLGLTEAF | SEQ ID NO: 3665 |
| ASSLPGNEQF | SEQ ID NO: 3666 |
| ASSSRMNTEAF | SEQ ID NO: 3667 |
| ASSYGQGAYEQY | SEQ ID NO: 3668 |

TABLE I-continued

| Sequence | Sequence ID No |
|---|---|
| ASSPTANYGYT | SEQ ID NO: 3669 |
| ASSSRDRGYEQY | SEQ ID NO: 3670 |
| ASSSPGQGTDTQY | SEQ ID NO: 3671 |
| ASSETSGSTDTQY | SEQ ID NO: 3672 |
| ASSSQLNTEAF | SEQ ID NO: 3673 |
| ASSPSPYEQY | SEQ ID NO: 3674 |
| ASSLGHEQF | SEQ ID NO: 3675 |
| ASSPPSQETQY | SEQ ID NO: 3676 |
| ASSSGGNQPQH | SEQ ID NO: 3677 |
| ASSSTGGYEQY | SEQ ID NO: 3678 |
| ASSFGQLNTEAF | SEQ ID NO: 3679 |
| ASSLTSNTEAF | SEQ ID NO: 3680 |
| ASSFQGDTEAF | SEQ ID NO: 3681 |
| ASSLVDEQY | SEQ ID NO: 3682 |
| ASSLGVMNTEAF | SEQ ID NO: 3683 |
| ASSFRLNTEAF | SEQ ID NO: 3684 |
| ASSYGTGSYEQY | SEQ ID NO: 3685 |
| ASSPGTSGTYEQY | SEQ ID NO: 3686 |
| ASSLRTANTEAF | SEQ ID NO: 3687 |
| ASSLGTTEAF | SEQ ID NO: 3688 |
| ASSLGGTQETQY | SEQ ID NO: 3689 |
| ASSQGPYNEQF | SEQ ID NO: 3690 |
| ASSSLGYEQY | SEQ ID NO: 3691 |
| ASRDSYNEQF | SEQ ID NO: 3692 |
| ASSLESDTQY | SEQ ID NO: 3693 |
| ASSQGSTEAF | SEQ ID NO: 3694 |
| ASSPDRGETQY | SEQ ID NO: 3695 |
| ASSLAGQGYEQY | SEQ ID NO: 3696 |
| ASRGTANTEAF | SEQ ID NO: 3697 |
| ASSSGGSSYEQY | SEQ ID NO: 3698 |
| ASSGLAGGTDTQY | SEQ ID NO: 3699 |
| ASSLVGEETQY | SEQ ID NO: 3700 |
| ASSEGSYEQY | SEQ ID NO: 3701 |
| ASSPGGDTEAF | SEQ ID NO: 3702 |
| ASSQDNEQF | SEQ ID NO: 3703 |
| ASSLAGGAYNEQF | SEQ ID NO: 3704 |
| ASSFTGGNQPQH | SEQ ID NO: 3705 |
| ASSSRGGTEAF | SEQ ID NO: 3706 |
| ASSLAGYSNQPQH | SEQ ID NO: 3707 |
| ASSSTGSSYNEQF | SEQ ID NO: 3708 |
| ASSLGSSYNSPLH | SEQ ID NO: 3709 |
| ASSLDGGTDTQY | SEQ ID NO: 3710 |
| ASSLTGSNTEAF | SEQ ID NO: 3711 |
| ASSRPNTEAF | SEQ ID NO: 3712 |
| ASSLETEAF | SEQ ID NO: 3713 |
| ASSYPGTDTQY | SEQ ID NO: 3714 |
| ASSPGTGGYNEQF | SEQ ID NO: 3715 |
| ASSPTGDEQY | SEQ ID NO: 3716 |
| ASSQGQGTDTQY | SEQ ID NO: 3717 |
| ASSQGRTDTQY | SEQ ID NO: 3718 |
| ASSPGQGRETQY | SEQ ID NO: 3719 |
| ASSGTGQETQY | SEQ ID NO: 3720 |
| ASSQDSGNTIY | SEQ ID NO: 3721 |
| ASSLRAYEQY | SEQ ID NO: 3722 |
| ASSLGTSNEQF | SEQ ID NO: 3723 |
| ASSLSRDQPQH | SEQ ID NO: 3724 |
| ASSLKVNTEAF | SEQ ID NO: 3725 |
| ASSPGANVLT | SEQ ID NO: 3726 |
| ASSLIGDTQY | SEQ ID NO: 3727 |
| ASSESGYEQY | SEQ ID NO: 3728 |
| ASSPSGTEAF | SEQ ID NO: 3729 |
| ASSRTSGGYNEQF | SEQ ID NO: 3730 |
| ASSSDYNEQF | SEQ ID NO: 3731 |
| ASSLRRDTEAF | SEQ ID NO: 3732 |
| ASSRNQETQY | SEQ ID NO: 3733 |
| ASSSGLAGSTDTQY | SEQ ID NO: 3734 |
| ASSLAGNEQY | SEQ ID NO: 3735 |
| ASSSDRDQPQH | SEQ ID NO: 3736 |
| ASSFTNTEAF | SEQ ID NO: 3737 |
| ASSLGGDYEQY | SEQ ID NO: 3738 |
| ASSPSRETQY | SEQ ID NO: 3739 |
| ASSLSSGSYEQY | SEQ ID NO: 3740 |
| ASSLVGGEQY | SEQ ID NO: 3741 |
| ASSFTGDTEAF | SEQ ID NO: 3742 |
| ASSLSDEQF | SEQ ID NO: 3743 |
| ASSPGGGETQY | SEQ ID NO: 3744 |
| ASSQGGYNEQF | SEQ ID NO: 3745 |
| ASSPGTSGSTDTQY | SEQ ID NO: 3746 |

TABLE I-continued

| Sequence | Sequence ID No |
|---|---|
| ASSQTENTEAF | SEQ ID NO: 3747 |
| ASSFGRNQPQH | SEQ ID NO: 3748 |
| ASSWGRNTEAF | SEQ ID NO: 3749 |
| ASSPRNQPQH | SEQ ID NO: 3750 |
| ASRGGYEQY | SEQ ID NO: 3751 |
| ASSQGNTIY | SEQ ID NO: 3752 |
| ASSQGSNTEAF | SEQ ID NO: 3753 |
| ASSRGDEQF | SEQ ID NO: 3754 |
| ASSPDRSYGYT | SEQ ID NO: 3755 |
| ASSLDSNEQF | SEQ ID NO: 3756 |
| ASSFSADTQY | SEQ ID NO: 3757 |
| ASSLVTNTEAF | SEQ ID NO: 3758 |
| ASSFAGELF | SEQ ID NO: 3759 |
| ASSLDSSYNEQF | SEQ ID NO: 3760 |
| ASSRDGNYGYT | SEQ ID NO: 3761 |
| ASSLSLNQPQH | SEQ ID NO: 3762 |
| ASSVAGGTDTQY | SEQ ID NO: 3763 |
| ASSLGQGDYGYT | SEQ ID NO: 3764 |
| ASSRDRVYEQY | SEQ ID NO: 3765 |
| ASSTGTGSYEQY | SEQ ID NO: 3766 |
| ASSLQSSYEQY | SEQ ID NO: 3767 |
| ASSLGTGNTIY | SEQ ID NO: 3768 |
| ASSLLGADTQY | SEQ ID NO: 3769 |
| ASSFRGQPQH | SEQ ID NO: 3770 |
| ASSRTEETQY | SEQ ID NO: 3771 |
| ASSPRQGQETQY | SEQ ID NO: 3772 |
| ASSLTDYGYT | SEQ ID NO: 3773 |
| ASSPDRMNTEAF | SEQ ID NO: 3774 |
| ASSLGTSGNTIY | SEQ ID NO: 3775 |
| ASSRQGANTEAF | SEQ ID NO: 3776 |
| ASSFFTDTQY | SEQ ID NO: 3777 |
| ASSLDKNTEAF | SEQ ID NO: 3778 |
| ASSRYEQY | SEQ ID NO: 3779 |
| ASSRTGYGYT | SEQ ID NO: 3780 |
| ASSLGLAGGYEQY | SEQ ID NO: 3781 |
| ASRQGSNQPQH | SEQ ID NO: 3782 |
| ASSFGQSTDTQY | SEQ ID NO: 3783 |
| ASSFGGGETQY | SEQ ID NO: 3784 |
| ASSPTGGETQY | SEQ ID NO: 3785 |
| ASSLAGGSDTQY | SEQ ID NO: 3786 |
| ASSFGQMNTEAF | SEQ ID NO: 3787 |
| ASSTSSYNEQF | SEQ ID NO: 3788 |
| ASSPGLANEQF | SEQ ID NO: 3789 |
| ASSLAPQETQY | SEQ ID NO: 3790 |
| ASGDYEQY | SEQ ID NO: 3791 |
| ASSSGQGTYEQY | SEQ ID NO: 3792 |
| ASSSQGDTQY | SEQ ID NO: 3793 |
| ASSLLRTDTQY | SEQ ID NO: 3794 |
| ASRRGTDTQY | SEQ ID NO: 3795 |
| ASSLVRGTEAF | SEQ ID NO: 3796 |
| ASSLASGYEQY | SEQ ID NO: 3797 |
| ASSIGRNTEAF | SEQ ID NO: 3798 |
| ASSGQGAYEQY | SEQ ID NO: 3799 |
| ASSSASTDTQY | SEQ ID NO: 3800 |
| ASSFGPYEQY | SEQ ID NO: 3801 |
| ASSLGSSSYNEQF | SEQ ID NO: 3802 |
| ASSRGQGAYEQY | SEQ ID NO: 3803 |
| ASSFGSNTEAF | SEQ ID NO: 3804 |
| ASSEQGGTEAF | SEQ ID NO: 3805 |
| ASSQGTGSYEQY | SEQ ID NO: 3806 |
| ASSLGGRDTQY | SEQ ID NO: 3807 |
| ASSYKETQY | SEQ ID NO: 3808 |
| ASSTGNYGYT | SEQ ID NO: 3809 |
| ASSLFQETQY | SEQ ID NO: 3810 |
| ASSSGQGDQPQH | SEQ ID NO: 3811 |
| ASSLYGNQPQH | SEQ ID NO: 3812 |
| ASSLSGGYGYT | SEQ ID NO: 3813 |
| ASSIGGNQPQH | SEQ ID NO: 3814 |
| ASSDPYEQY | SEQ ID NO: 3815 |
| SASQETQY | SEQ ID NO: 3816 |
| ASSLQGSNTEAF | SEQ ID NO: 3817 |
| ASSLQGNTIY | SEQ ID NO: 3818 |
| ASSPGLAAYEQY | SEQ ID NO: 3819 |
| ASRGTSTDTQY | SEQ ID NO: 3820 |
| ASSFRDSSYEQY | SEQ ID NO: 3821 |
| ASSDGSTDTQY | SEQ ID NO: 3822 |
| ASSLRTVNTEAF | SEQ ID NO: 3823 |
| ASSRDYTDTQY | SEQ ID NO: 3824 |

TABLE I-continued

| Sequence | Sequence ID No |
|---|---|
| ASSRQGPYEQY | SEQ ID NO: 3825 |
| ASSLSGTQY | SEQ ID NO: 3826 |
| ASSPGLADNEQF | SEQ ID NO: 3827 |
| ASSRDNYGYT | SEQ ID NO: 3828 |
| ASSLAGGSSYEQY | SEQ ID NO: 3829 |
| ASSSLQETQY | SEQ ID NO: 3830 |
| ASSLPGETQY | SEQ ID NO: 3831 |
| ASSVGSTDTQY | SEQ ID NO: 3832 |
| ASSLVNSPLH | SEQ ID NO: 3833 |
| ASSLNSGANVLT | SEQ ID NO: 3834 |
| ASRSQETQY | SEQ ID NO: 3835 |
| ASSLATGELF | SEQ ID NO: 3836 |
| ASSPRGYGYT | SEQ ID NO: 3837 |
| ASSYGPNTEAF | SEQ ID NO: 3838 |
| ASSPDRSYEQY | SEQ ID NO: 3839 |
| ASSRGQGTDTQY | SEQ ID NO: 3840 |
| ASRYSNQPQH | SEQ ID NO: 3841 |
| ASSSQYEQY | SEQ ID NO: 3842 |
| ASSLRSDTQY | SEQ ID NO: 3843 |
| ASRRSTDTQY | SEQ ID NO: 3844 |
| ASSLGGENTEAF | SEQ ID NO: 3845 |
| ASSSLGTDTQY | SEQ ID NO: 3846 |
| ASSPPGNQPQH | SEQ ID NO: 3847 |
| ASSLAGVQETQY | SEQ ID NO: 3848 |
| ASSLNRETQY | SEQ ID NO: 3849 |
| ASSPPMNTEAF | SEQ ID NO: 3850 |
| ASSLGQLNQPQH | SEQ ID NO: 3851 |
| ASSLRGRETQY | SEQ ID NO: 3852 |
| ASSPQRNTEAF | SEQ ID NO: 3853 |
| ASSLSRYEQY | SEQ ID NO: 3854 |
| ASSPGLAGAYEQY | SEQ ID NO: 3855 |
| ASSPGLAGVNEQF | SEQ ID NO: 3856 |
| ASSRQGGETQY | SEQ ID NO: 3857 |
| ASRGQGGTEAF | SEQ ID NO: 3858 |
| ASSYDSYNEQF | SEQ ID NO: 3859 |
| ASSRTGYNEQF | SEQ ID NO: 3860 |
| ASSPDRSTDTQY | SEQ ID NO: 3861 |
| ASSSLGDTQY | SEQ ID NO: 3862 |
| ASSLVGRNTEAF | SEQ ID NO: 3863 |
| ASSLGLSSYEQY | SEQ ID NO: 3864 |
| ASSLGFNQPQH | SEQ ID NO: 3865 |
| ASSPQGAYEQY | SEQ ID NO: 3866 |
| ASSPDRANTEAF | SEQ ID NO: 3867 |
| ASSPTPNTEAF | SEQ ID NO: 3868 |
| ASSLPGELF | SEQ ID NO: 3869 |
| ASSFPGNTIY | SEQ ID NO: 3870 |
| ASSLRDSTDTQY | SEQ ID NO: 3871 |
| ASSFYTEAF | SEQ ID NO: 3872 |
| ATSDSNQPQH | SEQ ID NO: 3873 |
| ASSLEQETQY | SEQ ID NO: 3874 |
| ASSFPGELF | SEQ ID NO: 3875 |
| ASSLVSTEAF | SEQ ID NO: 3876 |
| ASSSTGMNTEAF | SEQ ID NO: 3877 |
| ASSLAPSTDTQY | SEQ ID NO: 3878 |
| ASSLAGLQETQY | SEQ ID NO: 3879 |
| ASSLSSSGNTIY | SEQ ID NO: 3880 |
| ASSQELNTEAF | SEQ ID NO: 3881 |
| ASSLLAGGQETQY | SEQ ID NO: 3882 |
| ASSPGLASYEQY | SEQ ID NO: 3883 |
| ASSPGTGGSYEQY | SEQ ID NO: 3884 |
| ASSLTGTGNTIY | SEQ ID NO: 3885 |
| ASSLGTSGQETQY | SEQ ID NO: 3886 |
| ASSPGTGGYGYT | SEQ ID NO: 3887 |
| ASSLDRGSNQPQH | SEQ ID NO: 3888 |
| ASSLTGGGQPQH | SEQ ID NO: 3889 |
| ASSLGQPNQPQH | SEQ ID NO: 3890 |
| ASSRGQGSYEQY | SEQ ID NO: 3891 |
| ASSFEGNQPQH | SEQ ID NO: 3892 |
| ASSQNSNQPQH | SEQ ID NO: 3893 |
| ASSLQGGGTEAF | SEQ ID NO: 3894 |
| ASSPSGYEQY | SEQ ID NO: 3895 |
| ASSLTSGNTIY | SEQ ID NO: 3896 |
| ASSPRGPYEQY | SEQ ID NO: 3897 |
| ASSLGDYNEQF | SEQ ID NO: 3898 |
| ASSSRDSYEQY | SEQ ID NO: 3899 |
| ASSGQGSYEQY | SEQ ID NO: 3900 |
| ASSQATDTQY | SEQ ID NO: 3901 |
| ASSLNRGETQY | SEQ ID NO: 3902 |

TABLE I-continued

| Sequence | Sequence ID No |
|---|---|
| ASSPREETQY | SEQ ID NO: 3903 |
| ASSPAGETQY | SEQ ID NO: 3904 |
| ASSYSGNTIY | SEQ ID NO: 3905 |
| ASGRNTEAF | SEQ ID NO: 3906 |
| ASSSTGNEQF | SEQ ID NO: 3907 |
| ASSLSGGQPQH | SEQ ID NO: 3908 |
| ASSLWETQY | SEQ ID NO: 3909 |
| ASSPGSGANVLT | SEQ ID NO: 3910 |
| SARENTEAF | SEQ ID NO: 3911 |
| ASSLGGAETQY | SEQ ID NO: 3912 |
| ASSLKGTDTQY | SEQ ID NO: 3913 |
| ASSLSGGAYEQY | SEQ ID NO: 3914 |
| ASSLRGGQETQY | SEQ ID NO: 3915 |
| ASSLRGVNTEAF | SEQ ID NO: 3916 |
| ASSQGRTEAF | SEQ ID NO: 3917 |
| ASSPTGANTEAF | SEQ ID NO: 3918 |
| ASSSGDYGYT | SEQ ID NO: 3919 |
| ASSPGGDYGYT | SEQ ID NO: 3920 |
| ASSLGTSGNEQF | SEQ ID NO: 3921 |
| ASSSQGDQPQH | SEQ ID NO: 3922 |
| ASSPRTGNQPQH | SEQ ID NO: 3923 |
| ASSLGVEQF | SEQ ID NO: 3924 |
| ASSLGTGDQPQH | SEQ ID NO: 3925 |
| ASSFQGTEAF | SEQ ID NO: 3926 |
| ASSDRGTEAF | SEQ ID NO: 3927 |
| ASSLRGEETQY | SEQ ID NO: 3928 |
| ASSLGQKNTEAF | SEQ ID NO: 3929 |
| ASSLDRDEQY | SEQ ID NO: 3930 |
| ASSYSNTGELF | SEQ ID NO: 3931 |
| ASSLSDTEAF | SEQ ID NO: 3932 |
| ASSASGSTDTQY | SEQ ID NO: 3933 |
| ASSFNYGYT | SEQ ID NO: 3934 |
| ASSPTGPYEQY | SEQ ID NO: 3935 |
| ASRTGTDTQY | SEQ ID NO: 3936 |
| ASSGQNYGYT | SEQ ID NO: 3937 |
| ASSSPGYEQY | SEQ ID NO: 3938 |
| ASRTYNEQF | SEQ ID NO: 3939 |
| ASSYGDTEAF | SEQ ID NO: 3940 |
| ASSLQGTGNTIY | SEQ ID NO: 3941 |
| ASSSQGLNTEAF | SEQ ID NO: 3942 |
| ASSERGNTEAF | SEQ ID NO: 3943 |
| ASSPDRSNQPQH | SEQ ID NO: 3944 |
| SARLAGGTDTQY | SEQ ID NO: 3945 |
| ASSLSGSTEAF | SEQ ID NO: 3946 |
| ASSLGSTGELF | SEQ ID NO: 3947 |
| ASSPRDSYNEQF | SEQ ID NO: 3948 |
| ASSPGGGYT | SEQ ID NO: 3949 |
| ASSQGNEQY | SEQ ID NO: 3950 |
| ASSRTGVNTEAF | SEQ ID NO: 3951 |
| ASSLTGENTEAF | SEQ ID NO: 3952 |
| ASSLERETQY | SEQ ID NO: 3953 |
| ASSLGGVTDTQY | SEQ ID NO: 3954 |
| ASSLASGSYNEQF | SEQ ID NO: 3955 |
| ASSSGTGNYGYT | SEQ ID NO: 3956 |
| ASSFENTEAF | SEQ ID NO: 3957 |
| ASSPRQGYEQY | SEQ ID NO: 3958 |
| ASSSGLYEQY | SEQ ID NO: 3959 |
| ASSLSGAYNEQF | SEQ ID NO: 3960 |
| ASSPGAYNEQF | SEQ ID NO: 3961 |
| ASSLGGVQETQY | SEQ ID NO: 3962 |
| ASSLTDYEQY | SEQ ID NO: 3963 |
| ASSLGEDTQY | SEQ ID NO: 3964 |
| ASSPPGSSYNEQF | SEQ ID NO: 3965 |
| ASSFRGSYNEQF | SEQ ID NO: 3966 |
| ASSGTLNTEAF | SEQ ID NO: 3967 |
| ASSFDTDTQY | SEQ ID NO: 3968 |
| ASSIGYEQY | SEQ ID NO: 3969 |
| ASSLAGDGYT | SEQ ID NO: 3970 |
| ASRGQPNTEAF | SEQ ID NO: 3971 |
| ASRDRAYEQY | SEQ ID NO: 3972 |
| ASSLARNQPQH | SEQ ID NO: 3973 |
| ASSSDGYEQY | SEQ ID NO: 3974 |
| ASSTGQGNTEAF | SEQ ID NO: 3975 |
| AISESYEQY | SEQ ID NO: 3976 |
| ASSLAPYNEQF | SEQ ID NO: 3977 |
| ASSLSGGADTQY | SEQ ID NO: 3978 |
| ASSWGLNTEAF | SEQ ID NO: 3979 |
| ASSRTAQETQY | SEQ ID NO: 3980 |

TABLE I-continued

| Sequence | Sequence ID No |
|---|---|
| ASSTSNQPQH | SEQ ID NO: 3981 |
| ASSPDRYNEQF | SEQ ID NO: 3982 |
| ATSRDRGYEQY | SEQ ID NO: 3983 |
| ASSFNQPQH | SEQ ID NO: 3984 |
| ASSDSSYNEQF | SEQ ID NO: 3985 |
| ASSLTENQPQH | SEQ ID NO: 3986 |
| ASSLGQTDTQY | SEQ ID NO: 3987 |
| ASSYSRGNTEAF | SEQ ID NO: 3988 |
| ASSLGLLNTEAF | SEQ ID NO: 3989 |
| ASSLGHNEQF | SEQ ID NO: 3990 |
| ASSVSDTQY | SEQ ID NO: 3991 |
| ASSFLSTDTQY | SEQ ID NO: 3992 |
| ASRITDTQY | SEQ ID NO: 3993 |
| ASSYTGGTEAF | SEQ ID NO: 3994 |
| ASSLGGNTDTQY | SEQ ID NO: 3995 |
| ASSPGTSGQETQY | SEQ ID NO: 3996 |
| ASSLDFTDTQY | SEQ ID NO: 3997 |
| ASSLDSQPQH | SEQ ID NO: 3998 |
| ASSQDGNTEAF | SEQ ID NO: 3999 |
| ASSYSTSTDTQY | SEQ ID NO: 4000 |

TABLE I-continued

| Sequence | Sequence ID No |
|---|---|
| ASSLRNSPLH | SEQ ID NO: 4001 |
| ASSAGGNTEAF | SEQ ID NO: 4002 |
| ASSLTGRETQY | SEQ ID NO: 4003 |
| ASSAYTDTQY | SEQ ID NO: 4004 |
| ASSLGQNTDTQY | SEQ ID NO: 4005 |
| ASSLGAGSYEQY | SEQ ID NO: 4006 |
| ASSQGGGYEQY | SEQ ID NO: 4007 |
| ASSLRTNTEAF | SEQ ID NO: 4008 |
| ASSLARSTDTQY | SEQ ID NO: 4009 |
| ASSSRDSSYEQY | SEQ ID NO: 4010 |
| ASSSGTGGNQPQH | SEQ ID NO: 4011 |
| ASSLWGQETQY | SEQ ID NO: 4012 |
| ASSRQGSGNTIY | SEQ ID NO: 4013 |
| ASSPYTEAF | SEQ ID NO: 4014 |

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The methodologies and the various embodiments thereof described herein are exemplary. Various other embodiments of the methodologies described herein are possible.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11047011B2). An electronic copy of the "Sequence Listing" will also be available from the USPTO upon request and payment of the fee set forth in 37 CFR 1.19(b)(3).

Now, therefore, the following is claimed:

1. A method for determining the immunorepertoire diversity in a patient, the method comprising:

(a) amplifying polynucleotides from a population of white blood cells from a human or animal subject in a reaction mix comprising target-specific nested primers directed to variable regions of the cells, to produce a set of first amplicons, at least a portion of the target-specific nested primers comprising additional nucleotides which, during amplification, serve as a template for incorporating into the first amplicons a binding site for at least one common primer;

(b) transferring a portion of the first reaction mix containing the first amplicons to a second reaction mix comprising at least one common primer;

(c) amplifying, using the at least one common primer, the first amplicons to produce a set of second amplicons;

(d) sequencing the second amplicons to identify CDR3 sequences in the subpopulation of white blood cells;

(e) using the identified CDR3 sequences to quantify the percentage of pCDR3 represented by the sample to provide a normality index, wherein pCDR3 sequences are shared by and identified from a reference pool of individuals and wherein the pCDR3 includes 100 or more of the group consisting of SEQ ID NO:1 through SEQ ID NO: 4014; and (f) identifying whether the normality index is normal or abnormal, wherein a normal state is characterized by the normality index meeting or exceeding a minimum percentage of pCDR3 and an abnormal state is characterized by the normality index failing to meet or exceed a minimum percentage of pCDR3.

2. The method of claim 1, wherein the population of cells is selected from the group consisting of all T cells [panT], CD8+ T cells [cytotoxic T (Ta)], CD4+ T cells and their subsets [TH1, TH2, TH17, regulatory T (Treg), follicular T (TFH)], developmental subsets of T cells, such as naive T (Tn), activated T (Ta), and memory T (Tm).

3. The method of claim 1, wherein the population of white blood cells is about 100,000 randomly-selected cells.

4. The method of claim 1, wherein the method is repeated about 10 to 100 times, each time with a random selection of cells, to determine the average percentage of pCDR3 expressed by the patient.

5. The method of claim 1, wherein the minimum percentage of pCDR3 is a percentage number from about 25 to about 75.

6. The method of claim 1, wherein the minimum percentage of pCDR3 is about 25 percent.

7. The method of claim 1, wherein the pCDR3 is composed of at least the 1000 most-frequently-shared CDR3 from the reference pool of individuals.

8. The method of claim 1, wherein the pCDR3 includes SEQ ID NO:1 through SEQ ID NO: 4014.

9. The method of claim 1, wherein the pCDR3 is composed of CDR3 shared by at least 50 percent of the pool of individuals.

10. The method of claim 9, wherein the pool contains at least 100 individuals.

11. The method of claim 9, wherein the pool contains about 1000 individuals.

12. The method of claim 9, wherein the pool is composed of healthy control individuals.

13. The method of claim 9, wherein the pool is composed of individuals with one or more specific disease states.

14. The method of claim 9, wherein the pool of individuals is approximately age-matched to the patient.

15. The method of claim 9, wherein the pool of individuals is gender-matched to the patient.

* * * * *